US012383637B2

(12) United States Patent
Strand et al.

(10) Patent No.: US 12,383,637 B2
(45) Date of Patent: *Aug. 12, 2025

(54) THERAPEUTIC AGENTS AND USES THEREOF

(71) Applicant: Janssen Biotech, Inc., Horsham, PA (US)

(72) Inventors: Sven-Erik Strand, Lund (SE); Amanda Thuy Tran, Stockholm (SE); Sven-Niklas Anders Axelsson, Bjarred (SE)

(73) Assignee: Janssen Biotech, Inc., Horsham, PA (US)

( * ) Notice: Subject to any disclaimer, the term of this patent is extended or adjusted under 35 U.S.C. 154(b) by 771 days.

This patent is subject to a terminal disclaimer.

(21) Appl. No.: 17/570,933

(22) Filed: Jan. 7, 2022

(65) Prior Publication Data

US 2022/0125961 A1   Apr. 28, 2022

Related U.S. Application Data

(63) Continuation of application No. 16/679,778, filed on Nov. 11, 2019, now abandoned, which is a continuation of application No. 15/135,028, filed on Apr. 21, 2016, now abandoned, which is a continuation of application No. 14/354,617, filed as application No. PCT/GB2012/052675 on Oct. 26, 2012, now Pat. No. 9,345,782.

(60) Provisional application No. 61/552,796, filed on Oct. 28, 2011.

(51) Int. Cl.
| | |
|---|---|
| *A61K 39/00* | (2006.01) |
| *A61K 47/68* | (2017.01) |
| *A61K 49/16* | (2006.01) |
| *A61K 49/22* | (2006.01) |
| *A61K 51/10* | (2006.01) |
| *C07K 16/18* | (2006.01) |
| *C07K 16/30* | (2006.01) |
| *C07K 16/40* | (2006.01) |
| *G01N 33/574* | (2006.01) |

(52) U.S. Cl.
CPC ...... *A61K 51/1072* (2013.01); *A61K 47/6803* (2017.08); *A61K 49/16* (2013.01); *A61K 49/221* (2013.01); *A61K 51/1018* (2013.01); *A61K 51/1075* (2013.01); *A61K 51/1093* (2013.01); *A61K 51/1096* (2013.01); *C07K 16/18* (2013.01); *C07K 16/3069* (2013.01); *C07K 16/40* (2013.01); *G01N 33/57434* (2013.01); *C07K 2317/565* (2013.01); *G01N 2333/96455* (2013.01)

(58) Field of Classification Search
CPC ............ A61K 51/1072; A61K 47/6803; A61K 49/16; A61K 49/221; A61K 51/1018; A61K 51/1075; A61K 51/1093; A61K 51/1096
See application file for complete search history.

(56) References Cited

U.S. PATENT DOCUMENTS

| | | |
|---|---|---|
| 4,235,871 A | 11/1980 | Papahadjopoulos et al. |
| 4,816,567 A | 3/1989 | Cabilly et al. |
| 4,822,535 A | 4/1989 | Ekman et al. |
| 5,851,451 A | 12/1998 | Takechi et al. |
| 6,326,471 B1 | 12/2001 | Kokolus et al. |
| 7,045,605 B2 | 5/2006 | Bander et al. |
| 7,053,042 B1 | 5/2006 | Denmeade et al. |
| 7,872,104 B2 | 1/2011 | Pettersson et al. |
| 8,481,683 B2 | 7/2013 | King et al. |
| 8,663,600 B2 | 3/2014 | Ulmert |
| 9,345,782 B2 | 5/2016 | Strand et al. |
| 10,100,125 B2 | 10/2018 | Timmermand et al. |
| 2002/0001588 A1 | 1/2002 | Sinha |
| 2004/0101914 A1 | 5/2004 | Pettersson et al. |
| 2004/0219163 A1 | 11/2004 | Frelinger et al. |
| 2005/0002929 A1 | 1/2005 | Sanchez-Madrid et al. |
| 2006/0182682 A1 | 8/2006 | Ulmert |
| 2010/0292166 A1 | 11/2010 | Lee et al. |
| 2011/0020360 A1 | 1/2011 | Laing et al. |

FOREIGN PATENT DOCUMENTS

| | | |
|---|---|---|
| EP | 0213303 A2 | 3/1987 |
| WO | 98/21365 A2 | 5/1998 |
| WO | 01/12218 A1 | 2/2001 |
| WO | 02/27323 A1 | 4/2002 |
| WO | 02/98897 A2 | 12/2002 |
| WO | 2006/087374 A1 | 8/2006 |
| WO | 2008/070569 A2 | 6/2008 |
| WO | 2008/112003 A2 | 9/2008 |
| WO | 2013/061083 A2 | 5/2013 |

OTHER PUBLICATIONS

U.S. Appl. No. 14/354,617, filed Apr. 28, 2014.
U.S. Appl. No. 15/135,028, filed Apr. 21, 2016.
U.S. Appl. No. 16/679,778, filed Nov. 11, 2019.
Larsson et al., Use of Monte Carlo simulations with a realistic rat phantom for examining the correlation between hematopoietic system response and red marrow absorbed dose in Brown Norway rats undergoing radionuclide therapy with (177)Lu- and (90)Y-BR96 mAbs, Med Phys. 2012, 4434-43, 39(7).

(Continued)

*Primary Examiner* — Lei Yao
(74) *Attorney, Agent, or Firm* — BakerHostetler

(57) ABSTRACT

The present application provides an agent comprising or consisting of a binding moiety with specificity for a kallikrein protein (for example, PSA or hK2) for use in the treatment of prostate cancer, and a method for the treatment of prostate cancer in a patient, the method comprising the step of administering a therapeutically effective amount of an agent comprising or consisting of a binding moiety with specificity for a kallikrein protein to the patient.

18 Claims, 46 Drawing Sheets

Specification includes a Sequence Listing.

(56) References Cited

OTHER PUBLICATIONS

Laune, et al. "Systematic exploration of the antigen binding activity of synthetic peptides isolated from the variable regions of immunoglobulins" J. Biol. Chem. (1997) 272(49):30937-44.
Lebeau et al., "Prostate-specific antigen: an overlooked candidate for the targeted treatment and selective imaging of prostate cancer", Biological Chemistry, vol. 391, No. 4, Apr. 2010, pp. 333-343.
Leinonen et al., Epitope mapping of antibodies against prostate-specific antigen with use of peptide libraries, Clin Chem 2002, 2208-16, 48.
Leinonen et al., Reactivity of anti-PSA monoclonal antibodies with recombinant human kallikrein-2, Tumor Biology, 1999, 35-37, 20.
Lilja, et al., "Prostate-Specific Antigen in Serum Occurs Predominantly in Complex with a1-Antichymotrypsin" Clin. Chem. (1991) 37(9):1618-1625.
Linden et al., Radioimmunotherapy using 131I-labeled anti-CD22 monoclonal antibody (LL2) in patients with previously treated B-cell lymphomas, Clin Cancer Res 1999, 3287s-3291s, 5(10 Suppl).
Ljungberg et al., 3D absorbed dose calculations based on SPECT: evaluation for 111-In/90-Y therapy using Monte Carlo simulations, Cancer Biother Radiopharm 2003, 99-107, 18.
Lovgren, et al., "Production and activation of recombinant hK2 with propeptide mutations resulting in high xpression levels" Eur. J. Biochem. (1999) 266:1050-1055.
Magklara et al., Decreased concentrations of prostate-specific antigen and human glandular kallikrein 2 in malignant versus nonmalignant prostatic tissue, Urology 2000, 527-532, 56.
Martensson et al., Determining maximal tolerable dose of the monoclonal antibody BR96 labeled with 90Y or 177Lu in rats: establishment of a syngeneic tumor model to evaluate means to improve radioimmunotherapy, Clin Cancer Res 2005, 7104s-7108s, 11.
Memari et al., Human Tissue Kallikrein 9: Production of Recombinant Proteins and Specific Antibodies, Biol. Chem. 2006, 387:733-740.
Meyers et al., Development of monoclonal antibody imaging of metastatic prostatic carcinoma, Prostate 1989, 209-220, 14.
Meziere, et al., "In Vivo T Helper Cell Response to Retro-Inverso Peptidomimetics" J. Immunol. (1997) 159 (7):3230-3237.
Miederer et al., Adv Drug Deliver Rev 60:1371-82, 2008 (Year: 2008).
Minarik et al., 90Y Bremsstrahlung imaging for absorbed-dose assessment in high-dose radioimmunotherapy, J. Nucl. Med 2010, 1974-1978, 51.
Monnet, et al. "Synthetic peptides derived from the variable regions of an anti-CD4 monoclonal antibody bind to CD4 and inhibit HIV-1 promoter activation in virus-infected cells" J. Biol. Chem. (1999) 274(6):3789-96.
Nilsson et al., Antigenic determinants of prostate-specific antigen (PSA) and development of assays specific for different forms of PSA, Brit. J Cancer 1997, 789-797, 75(6).
Nurmikko et al., Production and characterization of novel anti-prostate-specific antigen (PSA) monoclonal antibodies that do not detect internally cleaved Lys145-Lys146 inactive PSA, Clin Chem 2000, 1610-1618, 46.
Orlova et al., Cellular processing of (125)I- and (111)in-labeled epidermal growth factor (EGF) bound to cultured A431 tumor cells, Nucl Med Biol., 2000, 827-835, 27.
Oyen et al., Nuclear medicine techniques for the diagnosis and therapy of prostate carcinoma, Eur Urol. 2001 294-9, 40(3).
Pajunen, et al., "Cloning, sequencing, expression and characterization of three anti-estradiol-17b Fab fragments" Biochim. Biophys. Acta (1997) 1351:192-202.
Pascalis et al., "Grafting of "Abbreviated" Complementarity-Determining Regions Containing Specificity-Determining Residues Essential for Ligand Contact to Engineer a Less Immunogentic Humanized Monoclonal Antibody", The Journal of Immunology, 2002, vol. 169, 3076-3084.

Paul, W.E., "Fundamental Immunology", 3rd Edition, Raven Press, New York (1993) pp. 292-295.
Pessi, et al. "A designed metal-binding protein with a novel fold" Nature (1993) 362(6418):367-9.
Pettersson et al., Free and complexed prostate-specific antigen (PSA): in vitro stability, epitope map, and development of immunofluorometric assays for specific and sensitive detection of free PSA and PSA-alpha 1-antichymotrypsin complex, Clin. Chem. 1995, 1480-1488, 41(10).
Piironen et al. Measurement of circulating forms of prostate-specific antigen in whole blood immediately after venipuncture: implications for point-of-care testing, Clin Chem. 2001, 703-711, 47.
Pippin, et al., "Spectrophotometric method for the determination of a bifunctional DTPA ligand in DTPA-monoclonal antibody conjugates" Bioconjug Chem. (1992) 3(4):342-5.
Qiu, et al. "Small antibody mimetics comprising two complementarity-determining regions and a framework region for tumor targeting" Nat. Biotechnol. (2007) 25(8):921-9.
Rittenhouse et al., Human Kallikrein 2 (hK2) and prostate-specific antigen (PSA): two closely related, but distinct, kallikreins in the prostate, Clin. Lab Sci. 1998, 275-368, 35.
Rudikoff, et al., "Single amino acid substitution altering antigen-binding specificity" Proc. Natl. Acad. Sci. (1982) 79 (6):1979-83.
Schettino et al., Impact of fusion of indium-111 capromab pendetide vol. data sets with those from MRI or CT in patients with recurrent prostate cancer, Am J Roentgenol, 2004, 183, 519-524.
Scott, A.M., et al., "Antibody Therapy of Cancer" Nature Rev. Cancer (2012) 12:278-287.
Segars et al., Development of a 4-D digital mouse phantom for molecular imaging research, MOL Imaging Biol 2004, 149-159, 6.
Sgouros et al., Bone marrow dosimetry for radioimmunotherapy: theoretical considerations, J. Nucl. Med., 1993, 689-694, 34.
Siivola et al., Time-resolved fluorescence imaging for specific and quantitative immunodetection of human kallikrein 2 and prostate-specific antigen in prostatic tissue sections, Urology 2000, 682-688, 56.
Sjogreen et al., The LundADose method for planar image activity quantification and absorbed-dose assessment in radionuclide therapy, Cancer Biother. Radiopharm., 2005, 92-97, 20.
Sjogreen-Gleisner et al., Dosimetry in patients with B-cell lymphoma treated with [(90)Y]ibritumomab tiuxetan or [(131)I]tositumomab, J. Nucl. Med. Mol. Imaging, 2011, 126-154, 55.
Skerra et al., Alternative non-antibody scaffolds for molecular recognition, Curr Opin Biotechnol. 2007, 295-304, 18(4).
Sklar, et al., "Flow cytometric analysis of ligand-receptor interactions and molecular assemblies" Annu Rev Biophys Biomol Struct. (2002) 31:97-119.
Smith-Jones: Radioimmunotherapy of prostate cancer, Quarterly J. Nucl. Med. & Mol. Imaging Torino, Dec. 2004; vol. 48: 297-304.
Stenman et al., Summary report of the TD-3 workshop: characterization of 83 antibodies against prostate-specific antigen, Tumour Biol. 1999, 1-12, 20.
Strand, et al., "Pharmacokinetic modeling" Med Phys. (1993) 20(2 Pt 2):515-27.
Taneja et al., Imaging in the diagnosis and management of prostate cancer, Rev. Urol. 2004, 101-113, 6.
Thompson, et al., "CLUSTAL W: improving the sensitivity of progressive multiple sequence alignment through sequence weighting, position-specific gap penalties and weight matrix choice" Nucleic Acids Research (1994) 22 (22):4673-4680.
Thorseti, et al., "Dipeptide Mimics. Conformationally Restricted Inhibitors of Angiotensin-Converting Enzyme", Biochem Biophys Res Commun., 1993, 111(1):166-71.
Timmermand, et al., "Preclinical imaging of kallikrein-related peptidase 2 (hK2) in prostate cancer with a 111In-radiolabelled monoclonal antibody, 11B6" EJNMMI Research (2014) 4:51, pp. 1-12.
Torizumi et al., Evaluation of Serum Prostate Specific Antigen in Diagnosis of Patients with Prostate Cancer, Radioisotopes 1991, 298-301, 40.
Tramontano, et al., "Framework residue 71 is a major determinant of the position and conformation of the second hypervariable region in the VH domains of immunoglobulins" J Mol Biol. (1990) 215(1):175-82.

(56) References Cited

OTHER PUBLICATIONS

Tremblay et al., Immunohistochemical study suggesting a complementary role of kallikreins hK2 and hK3 (prostate-specific antigen) in the functional analysis of human prostate tumors, Am J Pathology, 455-459, 150.
UniProtKB Accession No. P07288, Oct. 25, 2017.
UniProtKB Accession No. P20151, Oct. 25, 2017.
Väisänen et al., "Development of sensitive immunoassays for and total human glandular kallikrein 2", Clinical Chemistry, American Association For Clinical Chemistry, Washington, DC, vol. 50, No. 9, Jan. 1, 2004, pp. 1607-1617.
Väisänen et al., Abstract 374: Sensitive Two-site Immunoassays for Measurement of the Free and Total Forms of Human Glandular Kallikrein 2 (hK2), European Urology Supplements, 2002, 1(1):96.
Väisänen et al., Intact free prostate-specific antigen and free and total human glandular kallikrein 2. Elimination of assay interference by enzymatic digestion of antibodies to F(ab')2 fragments, Analytical Chemistry, 2006, 7809-15, 78 (22).
Van Oosten et al., Selecting Potential Targetable Biomarkers for Imaging Purposes in Colorectal Cancer Using TArget Selection Criteria (TASC): A Novel Target Identification Tool, Translational Oncology, 2011, 71-82, 4.
Vaughan, et al. "Of minibody, camel and bacteriophage" Comb. Chem. High Throughput Screen. (2001) 4(5):417-30.
Veber, et al., "Conformationally restricted bicyclic analogs of somatostatin" Proc. Natl. Acad. Sci. (1978) 75 (6):2636-2640.
Wenske et al., Evaluation of Molecular Forms of Prostate-Specific Antigen and Human Kallikrein 2 in Predicting Biochemical Failure After Radical Prostatectomy, International Journal Of Cancer, Feb. 1, 2009, 124:3, 659-663.
Zhu et al., Dual-label immunoassay for simultaneous measurement of prostate-specific antigen (PSA)-alpha1-antichymotrypsin complex together with free or total PSA, Clin Chem. 2003, 97-103.
Akin et al., Imaging of prostate cancer, Radiol Clin North Am. 2007, 207-22, 45(1).
Almagro, et al., "Humanization of antibodies" Frontiers in Bioscience (2008) 13:1619-1633.
Almqvist, et al., "In vitro and in vivo characterization of 177Lu-huA33 A radioimmunoconjugate against colorectal cancer" Nuclear Medicine and Biology (2006) 33:991-998.
Angov "Codon usage: Nature's roadmap to expression and folding of proteins" Biotechnol. J. (2011) 6:650-659.
Anonymous: "Doktorandplats i Medicinsk stralningsfysik", Internet citation, Oct. 5, 2010, pp. 1-2.
Armstrong et al., Biomarkers in the management and treatment of men with metastatic castration-resistant prostate cancer, Eur. Urol. 2012, 549-559, 61(3).
Axelsson et al., "Targeting Free Prostate-Specific Antigen for In Vivo Imaging of Prostate Cancer Using a Monoclonal Antibody Specific for Unique Epitopes Accessible on Free ProstateSpecific Antigen Alone", Cancer Biotherapy & Radiopharmaceuticals vol. 27, No. 4, May 1, 2012, pp. 243-251.
Bapat et al., Radioiodination of monoclonal antibody for prostate specific antigen, J. of Radioanalytical and Nuclear Chemistry, 2002, 227-230, 253.
Barbas, et al., "Assembly of combinatorial antibody libraries on phage surfaces: The gene III site" Proc. Natl. Acad. Sci. USA (1991) 88:7978-7982.
Bardies, et al., "Quantitative imaging for clinical dosimetry" Nuclear Instruments and Methods in Physics Research A (2006) 569:467-471.
Bast et al., Translational crossroads for biomarkers, Clin Cancer Res. 2005, 6103-8, 11(17).
Becker et al., Sensitive and specific immunodetection of human glandular kallikrein 2 in serum, Clin Chem, 2000, 198-206, 46.
Bianchi, et al. "High level expression and rational From an insoluble to a soluble molecule" J. Mol. Biol. (1994) 236(2):649-59.
Bolch et al., Mird Pamphlet No. 21: A generalized schema for radiopharmaceutical dosimetry-standardization of nomenclature, J. Nuclear Med. 2009, 477-484, 50.

Borgono et al., Human tissue kallikreins: physiologic roles and applications in cancer, Mol Cancer Res, 2004, 257-280, 2.
Britton et al., Prostate cancer: the contribution of nuclear medicine, BJU Int. 2000, 135-142, 86.
Bunka et al., Aptamers come of age—at last, Nature Reviews: Microbiology 2006, 588-96, 4(8).
Casi, G., et al., "Antibody-drug conjugates: Basic Concepts, Example and Future Perspectives" J. Controlled Rel. (2012) 161:422-428.
Casset et al., A Peptide Mimetic of an Anti-CD4 Monoclonal Antibody by Rational Design, BBRC, 2003, 307, 198-205.
Chengazi et al., Imaging prostate cancer with technetium-99m-7E11-C5.3 (CYT-351), Nucl. Med. 1997, 675-682, 38.
Chothia, et al., "Conformations of immunoglobulin hypervariable regions" Nature (1989) 342(6252):877-883.
Darson et al., Human glandular kallikrein 2 (hK2) expression in prostatic intraepithelial neoplasia and adenocarcinoma: a novel prostate cancer marker, Urology 1997, 857-862, 49.
David et al., "Imaging Androgen Receptor Signaling with a Radiotracer Targeting Free Prostate-Specific Antigen", Cancer Discovery, American Association For Cancer Research, US, vol. 2, Jan. 1, 2012, pp. 320-327.
Diamandis et al., Human kallikrein 11: a new biomarker of prostate and ovarian carcinoma, Cancer Research, 2002, 295-300, 62.
Drabovich et al., Selection of smart aptamers by methods of kinetic capillary electrophoresis, Anal Chem. 2006, 3171-8, 78(9).
Ensembl, Transcript: KLK2-201 (ENST00000325321), a product of gene ENSG00000167751, Dec. 2017.
Feneley et al., Imaging with prostate-specific membrane antigen (PSMA) in prostate cancer, Prostate Cancer Prostatic Dis. 2000 47-52, 3.
Finlay et al., Development of a dual monoclonal antibody immunoassay for total human kallikrein 2, Clin Chem, 2001, 1218-1224, 47.
Fisher et al., Generation of monoclonal antibodies specific for human kallikrein 2 (hK2) using hK2-expressing tumors, Prostate 2002, 153-165, 51.
Foote, et al., "Antibody Framework Residues Affecting the Conformation of the Hypervariable Loops" J. Mol. Biol. (1992) 224:487-499.
Gao, et al. "Molecular cloning of a proteolytic antibody light chain" J. Biol. Chem. (1994) 269(51):32389-93.
Garkavij et al., 177Lu-[DOTA0, Tyr3] octreotate therapy in patients with disseminated neuroendocrine tumors: Analysis of dosimetry with impact on future therapeutic strategy, Cancer 2010, 1084-1092, 116.
GenBank Accession No. AAF08275.1, Nov. 15, 1999.
GenBank Accession No. AAF08277.1, Nov. 15, 1999.
Goldenberg, D.M., "Radiolabelled monoclonal antibodies in the treatment of metastatic cancer" Current Onocology (2007) 14(1):39-42.
Hekim et al., "Novel Peptide Inhibitors of Human Kallikrein 2", Journal Of Biological Chemistry, vol. 281, No. 18, Jan. 1, 2006, pp. 12555-12560.
Holliger, P., et al., "Engineered Antibody Fragments and the Rise of Single Domains" Nature Biotech. (2005) 23:1126-1136.
Hoppe-Seyler et al., Peptide aptamers: powerful new tools for molecular medicine, J. Mol. Med., 2000, 426-30.
Hricak et al., Advances in imaging in the postoperative patient with a rising prostate-specific antigen level, Seminars in Oncology 2003, 616-634, 30.
Hsieh et al., Expression of human prostate-specific glandular kallikrein protein (hK2) in the breast cancer cell line T47-D, Cancer Res. 1997, 2651-6, 57.
Huang, et al., "A Time-Efficient, Linear-Space Local Similarity Algorithm" Adv. Appl. Math. (1991) 12:337-357.
Hudson, P.J., et al., "Engineered Antibodies" Nature Med. (2003) 9:129-134.
Kairemo et al., Radioimmunotherapy with 90Y-labeled monoclonal antibodies in a nude mouse ovarian cancer model, Acta Oncology, 1993, 801-805, 32.
Keenan, et al., "RADAR Realistic Animal Model Series for Dose Assessment" J Nucl Med (2010) 51:471-476.
Kellof et al., Challenges in clinical prostate cancer: role of imaging, AJR 2009, 1455-1470, 192.

(56) References Cited

OTHER PUBLICATIONS

Kim et al., The unfolding treatment landscape for men with castration-resistant prostate cancer, Clin. Investig., 2011, 1533-44, 1(11).

Krebber, et al., "Reliable cloning of functional antibody variable domains from hybridomas and spleen cell repertoires employing a reengineered phage display system" Journal of Immunological Methods (1997) 201:35-55.

Ladner, R.C. "Antibodies cut down to size" Nat. Biotechnol. (2007) 25(8):875-7.

Larrson et al., Monte Carlo calculations of absorbed doses in tumours using a modified MOBY mouse phantom for pre-clinical dosimetry studies, Acta Oncol. 2011, 973-80, 50(6).

Larsson et al., Mouse S-Factors Based on Monte Carlo Simulations in the Anatomical Realistic Moby Phantom for Internal Dosimetry, Cancer Biother Radiopharm 2007, 438-442, 22.

TABLE 3. TUMOR-TO-ORGAN RATIOS (n=34)

| Tissue | 4 h (n = 8) | 24 h (n = 8) | 72 h (n = 8) | 168 h (n = 5) | 312 h (n = 5) |
|---|---|---|---|---|---|
| Blood | 0.44 | 0.78 | 0.35 | 0.47 | 0.22 |
| Spleen | 2.65 | 4.21 | 1.85 | 2.27 | 1.41 |
| Lungs | 1.26 | 1.83 | 0.82 | 1.19 | 0.55 |
| Kidneys | 1.05 | 2.61 | 1.37 | 1.43 | 0.70 |
| Liver | 1.72 | 2.61 | 1.30 | 1.62 | 1.05 |
| Bone marrow | 1.94 | 3.12 | 1.06 | 2.36 | 1.37 |
| Prostate | 3.05 | 4.44 | 1.95 | 2.57 | 0.73 |
| Muscle | 13.25 | 15.52 | 4.66 | 7.25 | 2.57 |
| Brain | 11.56 | 32.83 | 16.15 | 21.40 | 8.80 |

FIGURE 3

(C) H&E Staining    (D) IHC Staining 5.7 mm

Particulate radionuclide emissions

- Long-range betas
  - Range > 1mm
    - $^{90}Y$, $^{32}P$, $^{186}Re$
- Medium-range betas
  - Range > 200 μm
    - $^{131}I$, $^{177}Lu$
- Low-energy betas
  - Range < 200 μm
    - $^{45}Ca$, $^{35}S$, $^{14}C$
- Conversion and Auger electrons
  - Range μm – nm
    - $^{51}Cr$, $^{67}Ga$, $^{99}Tc^m$, $^{111}In$, $^{123}I$, $^{125}I$, $^{201}Tl$ Tumour targeting agent

```
Peptide     CHSACSKHCFVYC (VI-21) SEQ ID NO: 6
            CHSACSKHCFVHC (VI-15) SEQ ID NO: 7
            CKS MDGGWTC (VI-14) SEQ ID NO: 8
            CPS VDGGWTC (VI-13) SEQ ID NO: 9
              1          11         21         31         41
PSA         IVGGWECEKH SQPWQVLVAS RGRAVCGGVL VHPQWVLTAA HCIRNKSVIL
                                                       CGPG IDSWVC (III-8) SEQ ID NO: 10
             51         61         71         81         91
PSA         LGRHSLFHPE DTGQVFQVSH SFPHPLYDMS LLKNRFLRPG DDSSHDLMLL
                                              CTWHWSPEE C (VI-18) SEQ ID NO: 11
                                              CPADFE FLC (VI-12) SEQ ID NO: 12
            101        111        121        131        141
PSA         RLSEPAELTD AVKVMDLPTQ EPALGTTCYA SGWGSIEPEE FLTPKKLQCV
                        CHPYKVGC (I-16) SEQ ID NO: 13   CDY MPLVDNC (III-12) SEQ ID NO: 14
            151        161        171        181        191
PSA         DLHVISNDVC AQVHPQKVTK FMLCAGRWTG GKSTCSGDSG GPLVCNGVLQ
            CKSWGSSRC (I-9) SEQ ID NO: 15
            201        211        221        231
PSA         GITSWGSEPC ALPERPSLYT KVVHYRKWIK DTIVANP SEQ ID NO: 16
```

FIGURE 14

FIGURE 15
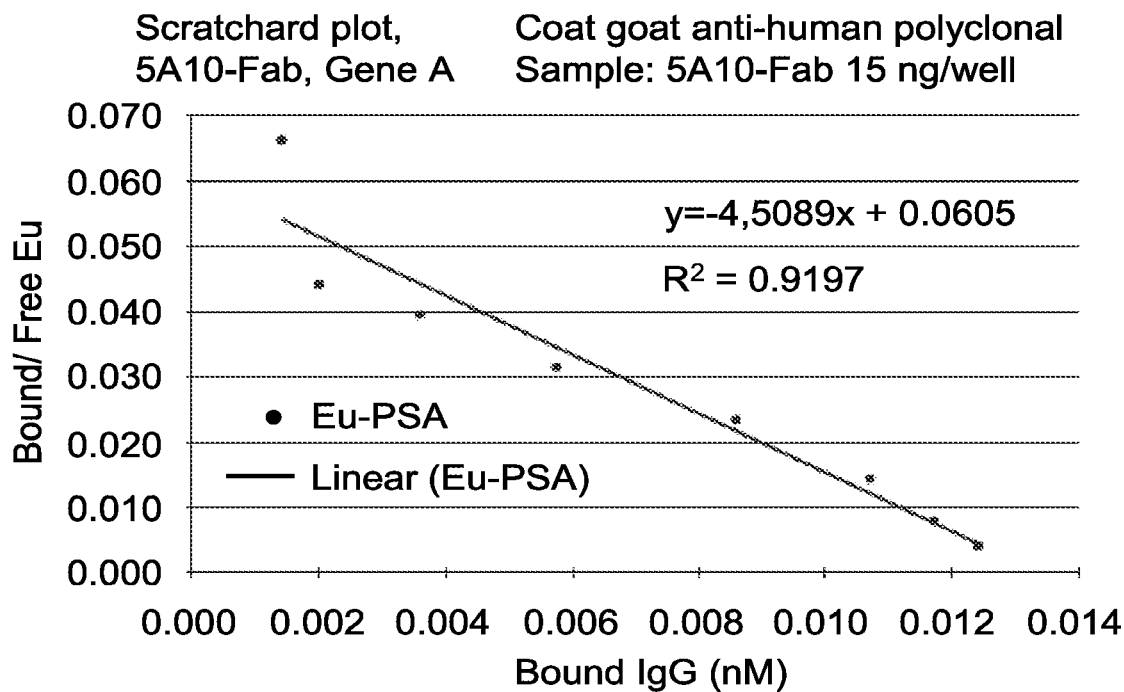
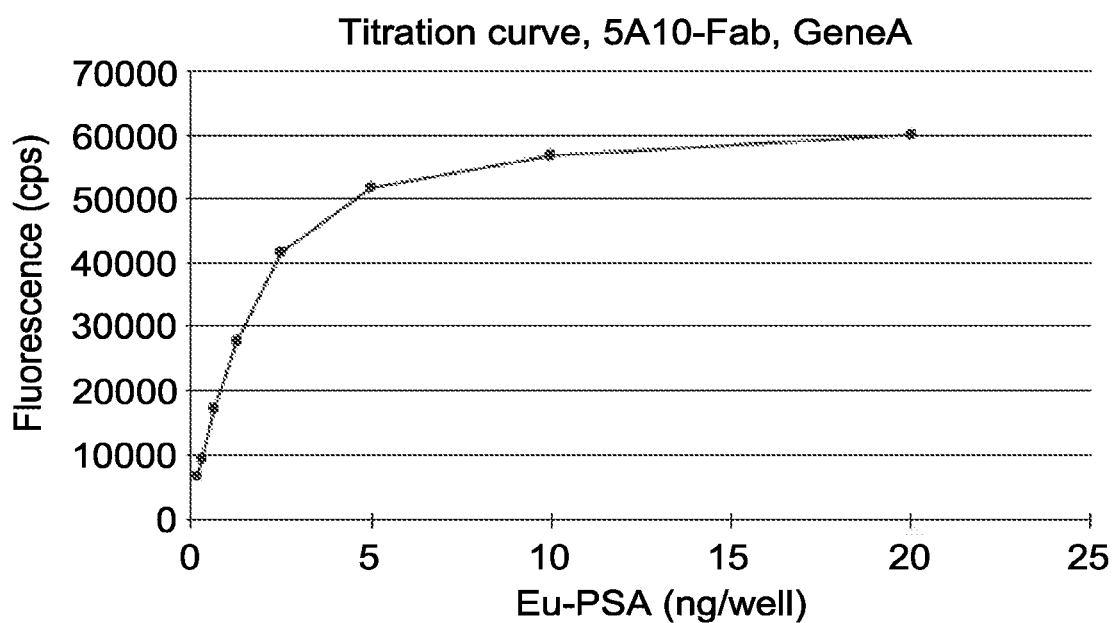

FIGURE 21 (*continued*)
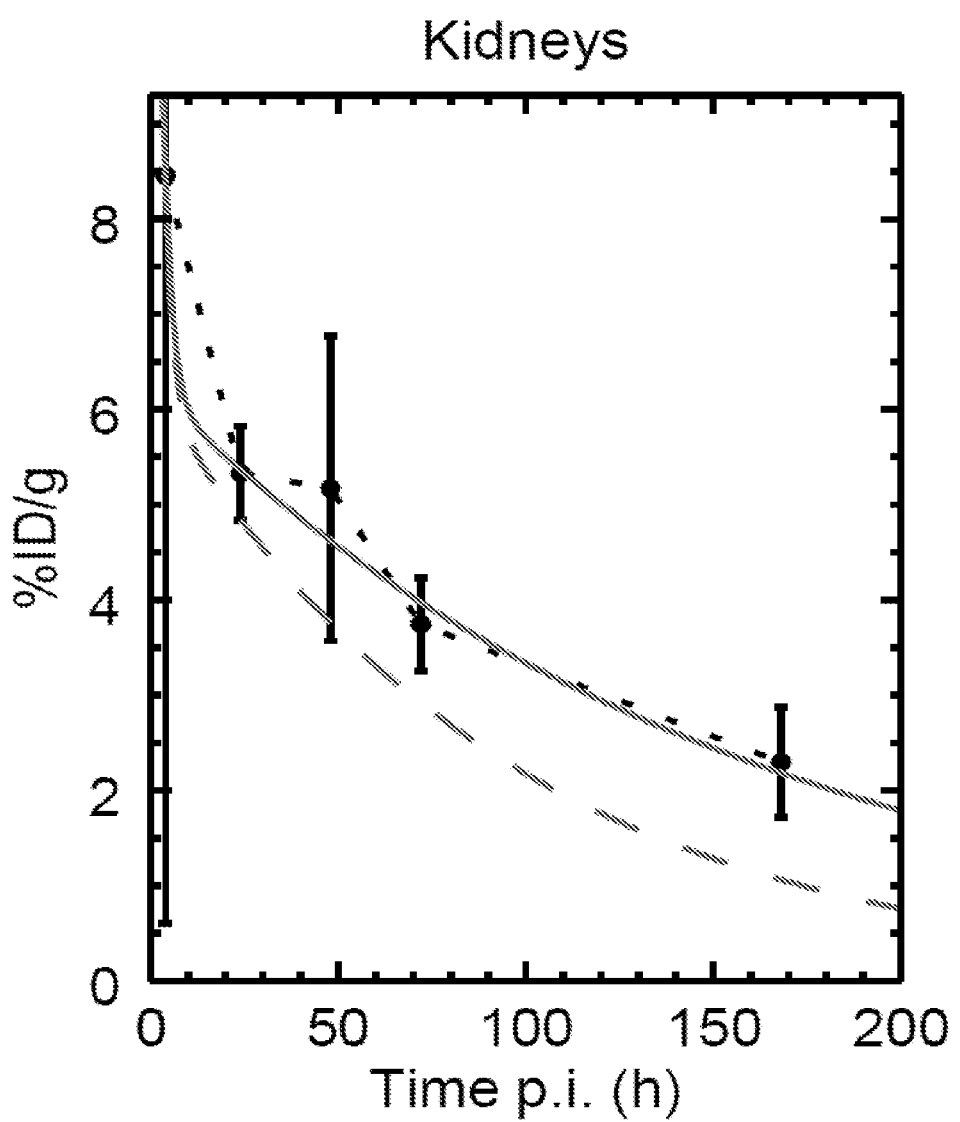

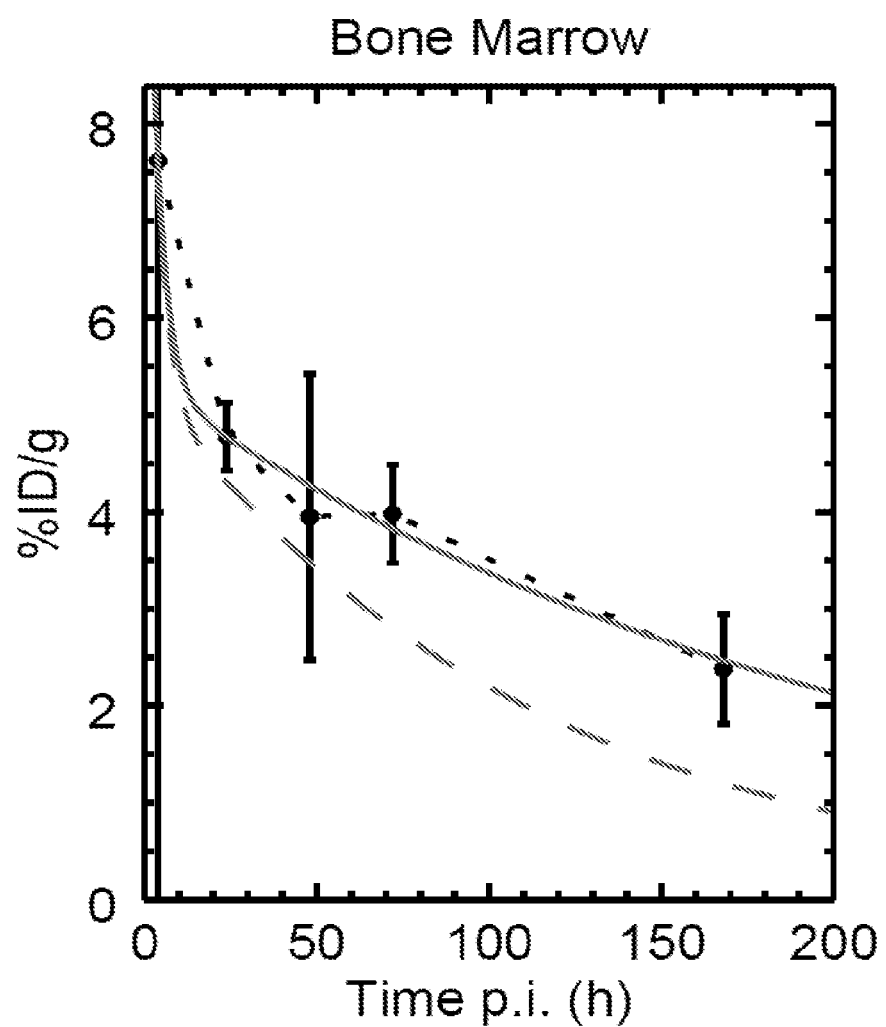
FIGURE 21 (*continued*)

FIGURE 21 (*continued*)
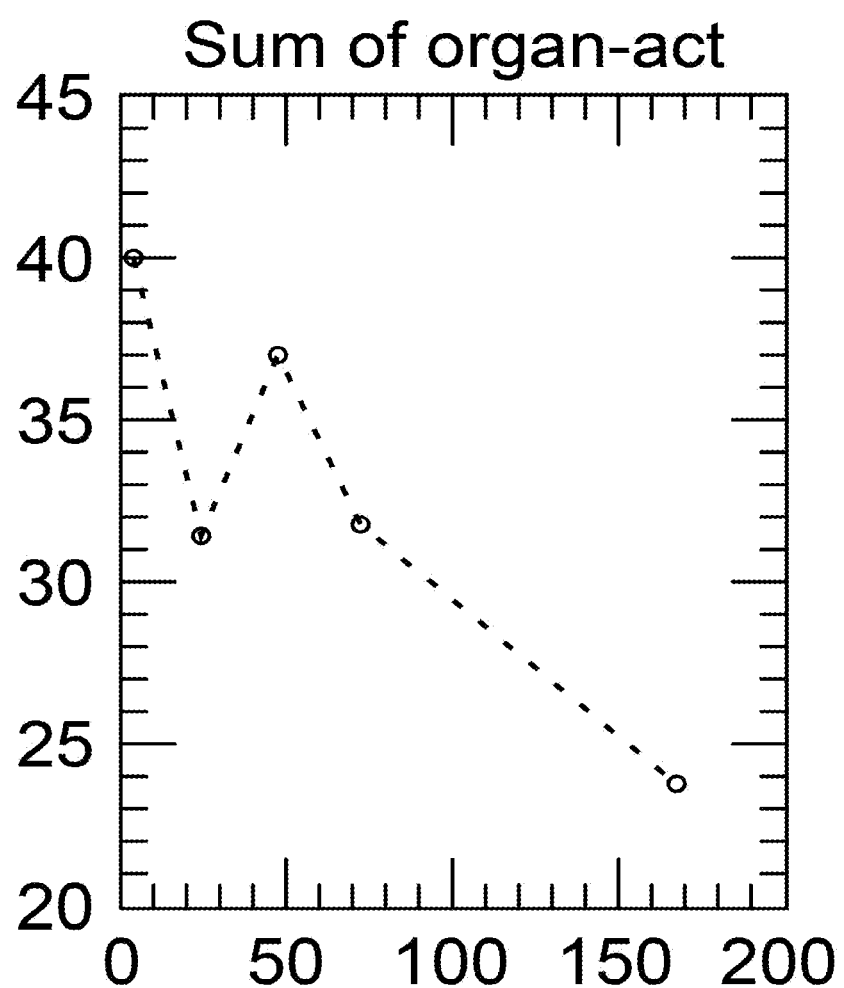

SEQUENCE LISTING

```
<160> NUMBER OF SEQ ID NOS: 16

<210> SEQ ID NO 1
<211> LENGTH: 119
<212> TYPE: PRT
<213> ORGANISM: Artificial Sequence
<220> FEATURE:
<223> OTHER INFORMATION: 5A10 Heavy chain

<400> SEQUENCE: 1

Glu Val Gln Leu Val Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Thr
            20                  25                  30

Gly Met Gly Val Ser Trp Ile Arg Gln Pro Ser Gly Lys Gly Leu Glu
        35                  40                  45

Trp Leu Ala His Leu Tyr Trp Asp Glu Asp Lys Arg Tyr Asn Pro Ser
    50                  55                  60

Leu Lys Ser Arg Leu Thr Ile Ser Glu Asp Ser Ser Arg Asn Gln Val
65                  70                  75                  80

Phe Leu Lys Ile Thr Ser Val Gly Pro Ala Asp Ser Ala Thr Tyr Tyr
                85                  90                  95

Cys Ala Arg Lys Gly Tyr Gly Tyr Phe Asp Tyr Trp Gly Gln Gly
                100                 105                 110

Thr Ala Leu Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: 5A10 Light chain
```

-continued

<400> SEQUENCE: 2

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asn Thr Asp
            20                  25                  30

Val Ala Trp Tyr Gln Gln Lys Pro Gly Gln Ser Pro Lys Ala Leu Ile
        35                  40                  45

Phe Ser Thr Ser Tyr Arg Ser Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Ser Asn Tyr Pro Leu
                85                  90                  95

Thr Phe Gly Ala Gly Thr Lys Val Asp Leu Asn
            100                 105
```

<210> SEQ ID NO 3
<211> LENGTH: 261
<212> TYPE: PRT
<213> ORGANISM: Homo sapiens

<400> SEQUENCE: 3

```
Met Trp Asp Leu Val Leu Ser Ile Ala Leu Ser Val Gly Cys Thr Gly
1               5                   10                  15

Ala Val Pro Leu Ile Gln Ser Arg Ile Val Gly Gly Trp Glu Cys Glu
            20                  25                  30

Lys His Ser Gln Pro Trp Gln Val Ala Val Tyr Ser His Gly Trp Ala
        35                  40                  45

His Cys Gly Gly Val Leu Val His Pro Gln Trp Val Leu Thr Ala Ala
    50                  55                  60

His Cys Leu Lys Lys Asn Ser Gln Val Trp Leu Gly Arg His Asn Leu
65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
        115                 120                 125

Pro Ala Lys Ile Thr Asp Val Val Lys Val Leu Gly Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
        195                 200                 205

Cys Gly Gly Asp Ser Gly Gly Pro Leu Val Cys Asn Gly Val Leu Gln
    210                 215                 220

Gly Ile Thr Ser Trp Gly Pro Glu Pro Cys Ala Leu Pro Glu Lys Pro
225                 230                 235                 240

Ala Val Tyr Thr Lys Val Val His Tyr Arg Lys Trp Ile Lys Asp Thr
                245                 250                 255
```

Ile Ala Ala Asn Pro
            260

<210> SEQ ID NO 4
<211> LENGTH: 117
<212> TYPE: PRT
<213> ORGANISM: Artificial Sequence
<220> FEATURE:
<223> OTHER INFORMATION: 11B6 Heavy chain

<400> SEQUENCE: 4

Asp Val Gln Leu Gln Glu Ser Gly Pro Gly Leu Val Lys Pro Ser Gln
1               5                   10                  15

Ser Leu Ser Leu Thr Cys Thr Val Thr Gly Asn Ser Ile Thr Ser Asp
            20                  25                  30

Tyr Ala Trp Asn Trp Ile Arg Gln Phe Pro Gly Asn Arg Leu Glu Trp
        35                  40                  45

Met Gly Tyr Ile Ser Tyr Ser Gly Ser Thr Thr Tyr Ser Pro Ser Leu
    50                  55                  60

Lys Ser Arg Phe Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Phe Cys
                85                  90                  95

Ala Thr Gly Tyr Tyr Tyr Gly Ser Gly Phe Trp Gly Gln Gly Thr Leu
            100                 105                 110

Val Thr Val Ser Ser
        115

<210> SEQ ID NO 5
<211> LENGTH: 111
<212> TYPE: PRT
<213> ORGANISM: Artificial Sequence
<220> FEATURE:
<223> OTHER INFORMATION: 11B6 Light chain

<400> SEQUENCE: 5

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Phe
            20                  25                  30

Gly Thr Ser Leu Met His Trp Tyr Arg Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile Gln
65                  70                  75                  80

Pro Val Glu Glu Asp Asp Phe Ser Met Tyr Phe Cys Gln Gln Thr Arg
                85                  90                  95

Lys Val Pro Tyr Thr Phe Gly Gly Gly Thr Lys Leu Glu Ile Lys
            100                 105                 110

<210> SEQ ID NO 6
<211> LENGTH: 13
<212> TYPE: PRT
<213> ORGANISM: Homo sapiens

<400> SEQUENCE: 6

Cys His Ser Ala Cys Ser Lys His Cys Phe Val Tyr Cys
1               5                   10

<210> SEQ ID NO 7
<211> LENGTH: 13
<212> TYPE: PRT
<213> ORGANISM: Homo sapiens

<400> SEQUENCE: 7

Cys His Ser Ala Cys Ser Lys His Cys Phe Val His Cys
1               5                   10

<210> SEQ ID NO 8
<211> LENGTH: 10
<212> TYPE: PRT
<213> ORGANISM: Homo sapiens

<400> SEQUENCE: 8

Cys Lys Ser Met Asp Gly Gly Trp Thr Cys
1               5                   10

<210> SEQ ID NO 9
<211> LENGTH: 10
<212> TYPE: PRT
<213> ORGANISM: Homo sapiens

<400> SEQUENCE: 9

Cys Pro Ser Val Asp Gly Gly Trp Thr Cys
1               5                   10

<210> SEQ ID NO 10
<211> LENGTH: 10
<212> TYPE: PRT
<213> ORGANISM: Homo sapiens

<400> SEQUENCE: 10

Cys Gly Pro Gly Ile Asp Ser Trp Val Cys
1               5                   10

<210> SEQ ID NO 11
<211> LENGTH: 10
<212> TYPE: PRT
<213> ORGANISM: Homo sapiens

<400> SEQUENCE: 11

Cys Thr Trp His Trp Ser Pro Glu Glu Cys
1               5                   10

<210> SEQ ID NO 12
<211> LENGTH: 9
<212> TYPE: PRT
<213> ORGANISM: Homo sapiens

<400> SEQUENCE: 12

Cys Pro Ala Asp Phe Glu Phe Leu Cys
1               5

<210> SEQ ID NO 13
<211> LENGTH: 8
<212> TYPE: PRT
<213> ORGANISM: Homo sapiens

<400> SEQUENCE: 13

Cys His Pro Tyr Lys Val Gly Cys
1               5

```
<210> SEQ ID NO 14
<211> LENGTH: 10
<212> TYPE: PRT
<213> ORGANISM: Homo sapiens

<400> SEQUENCE: 14

Cys Asp Tyr Met Pro Leu Val Asp Asn Cys
1               5                   10

<210> SEQ ID NO 15
<211> LENGTH: 9
<212> TYPE: PRT
<213> ORGANISM: Homo sapiens

<400> SEQUENCE: 15

Cys Lys Ser Trp Gly Ser Ser Arg Cys
1               5

<210> SEQ ID NO 16
<211> LENGTH: 237
<212> TYPE: PRT
<213> ORGANISM: Homo sapiens

<400> SEQUENCE: 16

Ile Val Gly Gly Trp Glu Cys Glu Lys His Ser Gln Pro Trp Gln Val
1               5                   10                  15

Leu Val Ala Ser Arg Gly Arg Ala Val Cys Gly Gly Val Leu Val His
            20                  25                  30

Pro Gln Trp Val Leu Thr Ala Ala His Cys Ile Arg Asn Lys Ser Val
        35                  40                  45

Ile Leu Leu Gly Arg His Ser Leu Phe His Pro Glu Asp Thr Gly Gln
    50                  55                  60

Val Phe Gln Val Ser His Ser Phe Pro His Pro Leu Tyr Asp Met Ser
65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys
        115                 120                 125

Tyr Ala Ser Gly Trp Gly Ser Ile Glu Pro Glu Glu Phe Leu Thr Pro
    130                 135                 140

Lys Lys Leu Gln Cys Val Asp Leu His Val Ile Ser Asn Asp Val Cys
145                 150                 155                 160

Ala Gln Val His Pro Gln Lys Val Thr Lys Phe Met Leu Cys Ala Gly
                165                 170                 175

Arg Trp Thr Gly Gly Lys Ser Thr Cys Ser Gly Asp Ser Gly Gly Pro
            180                 185                 190

Leu Val Cys Asn Gly Val Leu Gln Gly Ile Thr Ser Trp Gly Ser Glu
        195                 200                 205

Pro Cys Ala Leu Pro Glu Arg Pro Ser Leu Tyr Thr Lys Val Val His
    210                 215                 220

Tyr Arg Lys Trp Ile Lys Asp Thr Ile Val Ala Asn Pro
225                 230                 235
```

THERAPEUTIC AGENTS AND USES THEREOF

CROSS-REFERENCE TO RELATED APPLICATIONS

This application is a continuation of U.S. patent application Ser. No. 16/679,778, filed Nov. 11, 2019, which is a continuation of U.S. patent application Ser. No. 15/135,028, filed Apr. 21, 2016, which is a continuation of U.S. patent application Ser. No. 14/354,617, filed Apr. 28, 2014, which is a § 371 application of PCT/GB2012/052675, filed Oct. 26, 2012, which in turn claims priority to and benefit of U.S. Provisional Application 61/552,796, filed Oct. 28, 2011. The entire disclosure of each of the foregoing applications is incorporated by reference herein.

SEQUENCE LISTING

This application contains a Sequence Listing which has been submitted electronically in ASCII format and is hereby incorporated by reference in its entirety. Said ASCII copy, created Jan. 3, 2022, is named 103693_002690_sequence_listing.txt and is 10,648 bytes in size.

FIELD OF THE INVENTION

This invention pertains in general to the field of therapeutic agents and methods, particularly in field of prostate cancer.

BACKGROUND

The listing or discussion of an apparently prior-published document in this specification should not necessarily be taken as an acknowledgement that the document is part of the state of the art or is common general knowledge.

Prostate cancer is at the present time the most common form of cancer among men. The prostate is a walnut-sized gland in men that produces fluid that is a component in semen. The prostate has two, or more, lobes, or sections, enclosed by an outer layer of tissue. The prostate is located in front of the rectum and just below the urine bladder, and surrounds the urethra.

The occurrence of prostate cancer is highest in the northwestern part of Europe and in the United States. The growth of the tumor is usually a process that takes place during a long period of time. Prostate cancer is normally a mild form of cancer. In fact, the majority of men diagnosed with prostate cancer do survive, and only a minority of the men encounters a more aggressive form of prostate cancer, which metastasizes in an early stage. This form of prostate cancer may only be curable if it is diagnosed in an early stage, before the cancer has spread to extracapsular tissue.

Today diagnosis and monitoring of prostate cancer may be performed by measuring the concentration of a prostate specific antigen (PSA) in the blood of the patient. If the concentration of PSA is markedly high in several consecutive measurements, performed at different points of time, the assessment is that there is a probability of prostate cancer. At this point of time a biopsy may be performed to verify prostate cancer.

PSA (also known as kallikrein III) is a protein, constituted of a single chain of 237 amino acids, that is produced in the secretory cells of the prostate. These secretory cells may be found in the whole prostate gland. PSA is well established and thoroughly researched marker in respect of prostate cancer. By comparison with healthy cells the production of PSA is lower in malignant cells and higher in hyperplastic cells. It is therefore contradicting that in fact the concentration of PSA is higher in blood from men suffering from prostate cancer. However, one explanation may be that the malignant cells have a deteriorated cell structure, and are therefore more permeable to PSA.

Another important serine protease, which may be suitable for future therapy of prostate cancer, is human glandular kallikrein 2 (hK2). The gene coding hK2 is located on chromosome 19, together with the gene coding for PSA. hK2 is expressed mainly in the prostate tissue, just as PSA. In the prostate, PSA is present as an inactive pro-form and is activated through the peptidase action of hK2. Immunohistochemical research in respect of hK2 has shown that hK2 is expressed in relation to the level of differentiation. This means that hK2 is expressed in a higher yield in tissue of low differentiation, such as tissue subjected to prostate cancer, and in a lower yield in tissue of high differentiation, such as tissue subjected to benign prostatic hyperplasia (BPH) which is another common prostate problem.

Today's therapies of prostate cancer are surgery (e.g., radical prostatectomy), radiation therapy (including, brachytherapy and external beam radiation therapy, high-intensity focused ultrasound (HIFU), chemotherapy, oral chemotherapeutic drugs, cryosurgery (freezing the tumor), hormonal therapy (such as antiandrogen therapy), castration or combinations of the foregoing.

Most of these therapies (surgery and external radiation therapy) are, however, only (or primarily) useful for treatment of primary tumors and large metastases. Chemotherapy is used for disseminated of the cancer but for most of these patients, it is a palliative effect and/or prolonged survival. Other or complementary treatment modalities are therefore necessary to achieve considerable improvements of the disseminated malignant diseases, particular in cases of micrometastases.

Therapy, such as immunotherapy or radioimmunotherapy, using targeting molecules such as antibodies and fragments could give the possibility of therapy of disseminated disease.

Thus, there is a need for a new therapeutic agents and methods for treating prostate cancer, particular in cases of disseminated disease, metastases and micrometastases.

SUMMARY OF THE INVENTION

Accordingly, the present invention seeks to mitigate, alleviate or eliminate one or more of the above-identified deficiencies in the art and disadvantages singly or in any combination and solves at least the above-mentioned problems by providing a therapy method according to the appended patent claims.

A first aspect, present invention provides an agent comprising or consisting of a binding moiety with specificity for a kallikrein protein for use in the treatment of prostate cancer.

To put it another way, the first aspect of the present invention relates to the use of an agent comprising or consisting of a binding moiety with specificity for a kallikrein protein in the manufacture of a medicament for the treatment of prostate cancer.

Accordingly, first aspect also provides a method for the treatment of prostate cancer in a patient, the method comprising the step of administering a therapeutically effective amount of an agent comprising or consisting of a binding moiety with specificity for a kallikrein protein.

By "binding moiety" we include all types of chemical entity (for example, oligonucleotides, polynucleotide, polypeptides, peptidomimetics and small compounds) which are capable of binding specifically to a kallikrein protein. Advantageously, the binding moiety is capable of binding selectively (i.e., preferentially) to a kallikrein protein under physiological conditions.

As indicated above, the agents of the invention may comprise or consist of any suitable chemical entity constituting a binding moiety with specificity for a kallikrein protein.

Methods suitable for detecting interactions between a test chemical entity and a kallikrein protein are well known in the art. For example, ultrafiltration with ion spray mass spectroscopy/HPLC methods or other physical and analytical methods may be used. In addition, Fluorescence Energy Resonance Transfer (FRET) methods may be used, in which binding of two fluorescent labelled entities may be measured by measuring the interaction of the fluorescent labels when in close proximity to each other.

Alternative methods of detecting binding of a kallikrein protein to macromolecules, for example DNA, RNA, proteins and phospholipids, include a surface plasmon resonance assay, for example as described in Plant et al., 1995, *Analyt Biochem* 226(2), 342-348. Such methods may make use of a polypeptide that is labelled, for example with a radioactive or fluorescent label.

A further method of identifying a chemical entity that is capable of binding to a kallikrein protein is one where the kallikrein protein is exposed to the compound and any binding of the compound to the said kallikrein protein is detected and/or measured. The binding constant for the binding of the compound to the kallikrein protein may be determined. Suitable methods for detecting and/or measuring (quantifying) the binding of a compound to a kallikrein protein are well known to those skilled in the art and may be performed, for example, using a method capable of high throughput operation, for example a chip-based method. New technology, called VLSIPS™, has enabled the production of extremely small chips that contain hundreds of thousands or more of different molecular probes. These biological chips have probes arranged in arrays, each probe assigned a specific location. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location.

Another method of identifying compounds with binding affinity for a kallikrein protein is the yeast two-hybrid system, where the polypeptides of the invention can be used to "capture" proteins that bind the kallikrein protein. The yeast two-hybrid system is described in Fields & Song, *Nature* 340:245-246 (1989).

In one embodiment, the binding moiety may comprise or consist of a polypeptide.

For example, the binding moiety may comprise or consist of an antibody or an antigen-binding fragment thereof with binding specificity for a kallikrein protein, or a variant, fusion or derivative of said antibody or antigen-binding fragment, or a fusion of a said variant or derivative thereof, which retains the binding specificity for the kallikrein protein.

Thus, in one embodiment of the first aspect of the present invention, the binding moiety may be an antibody or antigen-binding fragment thereof.

By "antibody" we include substantially intact antibody molecules, as well as chimaeric antibodies, humanised antibodies, human antibodies (wherein at least one amino acid is mutated relative to the naturally occurring human antibodies), single chain antibodies, diabodies, bispecific antibodies, antibody heavy chains, antibody light chains, homodimers and heterodimers of antibody heavy and/or light chains, and antigen binding fragments and derivatives of the same.

By "antigen-binding fragment" we mean a functional fragment of an antibody that is capable of binding to a kallikrein protein. The binding affinity of the different antibody derivatives mentioned above may be determined with Scatchard's method using a fixed concentration of immobilized antibody fragment and varying concentrations of Eu-PSA tracer. Alternatively, the binding affinity may be determined using Surface Plasmon resonance (SPR) technology on a Biacore instrument. The analysis methods are further described in Example 8.

In particular, the antigen-binding fragment is selected from the group consisting of Fv fragments (e.g., single chain Fv and disulphide-bonded Fv), Fab-like fragments (e.g., Fab fragments, Fab' fragments and F(ab)$_2$ fragments), single variable domains (e.g., V$_H$ and V$_L$ domains) and domain antibodies (dAbs, including single and dual formats [i.e., dAb-linker-dAb]).

The advantages of using antibody fragments, rather than whole antibodies, are several-fold. The smaller size of the fragments may lead to improved pharmacological properties, such as better penetration of solid tissue and/or faster blood clearance which may permit higher therapeutic ratios. Moreover, antigen-binding fragments such as Fab, Fv, ScFv and dAb antibody fragments can be expressed in and secreted from microorganisms, such as *E. coli*, thus allowing the facile production of large amounts of the said fragments.

Also included within the scope of the invention are modified versions of antibodies and antigen-binding fragments thereof, e.g., modified by the covalent attachment of polyethylene glycol or other suitable polymer (see below).

Methods of generating antibodies and antibody fragments are well known in the art. For example, antibodies may be generated via any one of several methods which employ induction of in vivo production of antibody molecules, screening of immunoglobulin libraries (Orlandi. et al, 1989. *Proc. Natl. Acad. Sci. U.S.A.* 86:3833-3837; Winter et al., 1991, *Nature* 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120).

Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982).

Likewise, antibody fragments can be obtained using methods well known in the art (see, for example, Harlow & Lane, 1988, "*Antibodies: A Laboratory Manual*", Cold Spring Harbor Laboratory, New York). For example, antibody fragments according to the present invention can be prepared by proteolytic hydrolysis of the antibody or by expression in E. coli or mammalian cells (e.g., Chinese hamster ovary cell culture or other protein expression systems) of DNA encoding the fragment. Alternatively, antibody fragments can be obtained by pepsin or papain digestion of whole antibodies by conventional methods.

It will be appreciated by persons skilled in the art that for human therapy or diagnostics, human or humanised antibodies may be used. Humanised forms of non-human (e.g., murine) antibodies are genetically engineered chimaeric antibodies or antibody fragments having minimal-portions derived from non-human antibodies. Humanised antibodies include antibodies in which complementary determining regions of a human antibody (recipient antibody) are replaced by residues from a complementary determining region of a non human species (donor antibody) such as mouse, rat of rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. *Nature* 321:522-525; Riechmann et al., 1988, *Nature* 332:323-329; Presta, 1992, *Curr. Op. Struct. Biol.* 2:593-596).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, *Nature* 321:522-525; Reichmann et al., 1988. *Nature* 332:323-327; Verhoeyen et al., 1988, *Science* 239: 1534-15361; U.S. Pat. No. 4,816,567) by substituting human complementarity determining regions with corresponding rodent complementarity determining regions. Accordingly, such humanised antibodies are chimaeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Hoogenboom & Winter, 1991, *J. Mol. Biol.* 227:381; Marks et al., 1991, *J. Mol. Biol.* 222:581; Cole et al., 1985, In: *Monoclonal antibodies and Cancer Therapy*, Alan R. Liss, pp. 77; Boerner et al., 1991. *J. Immunol.* 147:86-95).

Once suitable antibodies are obtained, they may be tested for activity, for example by ELISA.

In an alternative embodiment of the first aspect of the invention, the binding moiety comprises or consists of a non-immunoglobulin binding moiety, for example as described in Skerra, *Curr Opin Biotechnol.* 2007 August; 18(4):295-304.

In a further alternative embodiment, the binding moiety comprises or consists of an aptamer. For example, the agent may comprise or consist of a peptide aptamer or a nucleic acid aptamer (see Hoppe-Seyler & Butz, 2000, *J Mol Med.* 78 (8): 426-30; Bunka D H & Stockley P G, 2006, *Nat Rev Microbiol.* 4 (8): 588-96 and Drabovich et al., 2006, *Anal Chem.* 78 (9): 3171-8).

In a still further alternative embodiment, the binding moiety comprises or consists of a small chemical entity. Such entities with kallikrein binding properties may be identified by screening commercial libraries of small compounds (for example, as available from ChemBridge Corporation, San Diego, USA).

Accordingly, the binding moiety present in the agent according to the first aspect of the present invention binds with specificity for a kallikrein protein. In this context, the phrase "binds with specificity" means that the binding moiety binds selectively to the target kallikrein protein in preference to other proteins, optionally including other kallikrein proteins. The skilled person is well aware of numerous methods for assessing the binding specificity of a binding molecule to a target. For example, where the binding molecule is, or is based on, an antibody, its ability to bind specifically to for a kallikrein protein may be assessed by an immunoassay, such as an ELISA, radioimmunoassay, or the like.

In one embodiment, the binding moiety may be said to bind with specificity for a kallikrein protein if it binds to the kallikrein protein in an immunoassay and/or under physiological conditions (such as conditions found in the prostate or other sites for treatment as discussed herein) with a binding affinity of greater than $1\times10^5$, $1\times10^6$, $1\times10^7$, $2\times10^7$, $1\times10^8$, $2\times10^8$, $1\times10^9$, $2\times10^9$, $1\times10^{10}$, $2\times10^{10}$, $3\times10^{10}$, $1\times10^{11}$ or more, such as within the range of from $1\times10^5$ to $3\times10^{10}$, or more.

The binding moiety as used in the first aspect of the present invention may have specificity for a human kallikrein protein. A human kallikrein protein is a serine protease belonging to the human tissue kallikrein gene family which was found to consist of least 15 members (Hsieh M L, *Cancer Res* 1997; 57; 2651-6). Kallikreins are heat-stable glycoproteins with a single polypeptide chain, with a Mw varying between 27-40 kDa.

The binding moiety as used in the first aspect of the present invention may have specificity for a kallikrein protein selected from the group consisting of prostate-specific antigen (PSA; hk3, human kallikrein 3) and human glandular kallikrein (hK2).

In one embodiment, the binding moiety has specificity for PSA. The term PSA is intended to include every known form of PSA, such as free PSA, precursor forms of PSA, internally nicked forms of PSA, low molecular weight free PSA, standard weight free PSA, inactive mature PSA, truncated forms of PSA, glycosylation variants of PSA, BPSA, inactive pro-PSA, and every complex of PSA, such as PSA bound to α1-antichymotrypsin (ACT), α1-protease inhibitor (API), and α2-macroglobulin (AMG). An exemplary primary amino acid of PSA is provided in FIG. 14 (see SEQ ID NO:16).

PSA, secreted from cancer cells, is in a more active state in comparison with PSA, secreted from BPH tissue. In the extracellular fluid PSA may be subjected to proteolytic degradation, thus leading to loss of activity and formation of complexes. Thus, it is also within the scope of the present invention to label compounds or entities, such as ACT, API, and AMG, bound or complexed to/with PSA.

In one preferred embodiment, the binding moiety has specificity for the free (that is, non-complexed) isoform of PSA compared to the complexed isoform of PSA. Binding moieties with specificity for the free isoform of PSA may have binding specificity for an epitope that is exposed on the free isoform of PSA, but is unexposed on the complexed isoform of PSA, such as a conformational (that is, non-linear) epitope. An example of such a conformational epitope is formed from amino acid residues that are part of the kallikrein-loop surrounding the catalytic cleft of PSA, and may include the active site triad of His41, Asn96, and Ser189). See Leinonen et al, *Clinical Chemistry* 48:12, 2208-2216 (2002) for further discussion and disclosure of numerous suitable epitopes on PSA, which are incorporated herein by reference.

Where the binding moiety as used in the first aspect of the present invention has specificity for PSA, then the binding moiety may compete for binding to PSA (such as the free isoform of PSA), or a peptide comprising the reactive epitope of PSA as bound by the binding moiety, with an antibody selected from the group consisting of PSA30, 4D4, 5C3, and 5A10, and an antigen-binding fragment thereof. Further discussion of such antibodies may be found in Pettersson et al, *Clin. Chem,* 41:10, 1480-1488 (1995); Nilsson et al, Brit. J. Cancer, 75:6, 789-797 (1997); Leinonen et al, *Clinical Chemistry* 48:12, 2208-2216 (2002); Väisänen et al, *Anal. Chem.,* 78:7809-7815 (2006); Evans-Axelsson et al., *Cancer Biother. Radiopharm.* 27:4, 243-51, EP 1 320 756 B1; and US 2004/101914, the contents of each of which are incorporated herein by reference.

The amino acid sequence of the constituent heavy and light chains of the exemplary anti-PSA antibody 5A10 is shown below (in which the CDR sequences are underlined).

5A10 Heavy chain
[SEQ ID NO: 1]
EVQLVESGPGILQPSQTLSLTCSFSGFSLS<u>TTGMGVS</u>WIRQPSGKGLEWL

AHLYWDEDKRYNPSLKSRLTISEDSSRNQVFLKITSVGPADSATYYCAR

<u>KGYYGYFDY</u>WGQGTALTVSS

5A10 Light chain
[SEQ ID NO: 2]
DIVMTQSQKFMSTSVGDRVSVTC<u>KASQNVNTDVA</u>WYQQKPGQSPKALIF <u>STSYRSS</u>GVPDRFTGSGSGTDFTLTITNVQSEDLAEYFC<u>QQYSNYPLT</u>

FGAGTKVDLN

In this context, the term "competes" includes the meaning that the presence of the agent comprising the binding moiety in a competitive assay along with an reference antibody selected from PSA30, 4D4, 5C3, and 5A10 can reduce the level of detectable binding of the reference antibody to PSA (such as free PSA) by 1%, 2%, 3%, 4%, 5%, 10%, 20%, 30%, 40%, 50%, 60%, 70%, 80%, 90%, 95%, 99% or 100% (for example, when the agent and the reference antibody are present in the test in equimolar amounts, and optionally wherein the test is performed under physiological conditions. Such analysis can be done by an immunoradiometric assay (IRMA) as described in Example 9.

Where the binding moiety as used in the first aspect of the present invention has specificity for PSA, then the binding moiety may comprises one or more complementarity determining regions (CDRs) of an antibody selected from the group consisting of PSA30, 4D4, 5C3, and 5A10 (as shown by the underlined sequences in SEQ ID NOS:1 to 8 above).

As is well established in the art, complete antibodies comprise six CDRs, three of which are present in the variable light ($V_L$) change, and the other three of which are present in the variable heavy ($V_H$) chain, It is not necessary for binding molecules to containing all six of the CDRs of any of these antibodies in order to retain the antigen binding activity, although in one embodiment the binding molecule may comprise all six CDRs from an antibody selected from the group consisting of PSA30, 4D4, 5C3, and 5A10.

Alternatively, the binding moiety may comprise less than six of the CDRs, such as:

five CDRs (i.e., 3 CDRs from the $V_H$ or $V_L$ region, 2 CDRs from the other variable region);

four CDRs (i.e., 3 CDRs from the $V_H$ or $V_L$ region, 1 CDR from the other variable region; or 2 CDRs from each of the $V_H$ and $V_L$ regions);

three CDRs (i.e., all three CDRs from one of the $V_H$ or $V_L$ regions, and none from the other; or 2 CDRs from the $V_H$ or $V_L$ region, 1 CDR from the other variable region);

two CDRs (i.e., two CDRs from one of the $V_H$ or $V_L$ regions, and none from the other; or 1 CDRs from each of the $V_H$ and $V_L$ regions); or one CDR from either of the $V_H$ or $V_L$ regions, from an antibody selected from the group consisting of PSA30, 4D4, 5C3, and 5A10.

It is well known in the art that three or fewer CDR regions (in some cases, even just a single CDR or a part thereof) are capable of retaining the antigen-binding activity of the antibody from which the CDR(s) are derived:

Laune et al. (1997), *JBC,* 272:30937-44—demonstrates that a range of hexapeptides derived from a CDR display antigen-binding activity (see abstract) and notes that synthetic peptides of a complete, single, CDR displays strong binding activity (see page 30942, right-hand column).

Monnet et al. (1999), *JBC,* 274:3789-96—shows that a range of 12-mer peptides and associated framework regions have antigen-binding activity (see abstract) and comments that a CDR3-like peptide alone is capable of binding antigen (see page 3785, left-hand column).

Qiu et al. (2007), *Nature Biotechnology,* 25:921-9—demonstrates that a molecule consisting of two linked CDRs are capable of binding antigen (see abstract and page 926, right-hand column).

Ladner et al. (2007), *Nature Biotechnology,* 25:875-7—is a review article reporting Qiu et al. (above) and commenting that molecules containing two CDRs are capable of retaining antigen-binding activity (see page 875, right-hand column).

Heap et al. (2005), *J. Gen. Virol.,* 86:1791-1800—reports that a "micro-antibody" (a molecule containing a single CDR) is capable of binding antigen (see abstract and page 1791, left-hand column) and shows that a cyclic peptide from an anti-HIV antibody has antigen-binding activity and function.

Nicaise et al. (2004) *Protein Science,* 13:1882-91—shows that a single CDR can confer antigen-binding activity and affinity for its lysozyme antigen Vaughan and Sollazzo (2001), *Combinatorial Chemistry & High Throughput Screening,* 4:417-430—is a review article describing minibodies that contain less than three CDR regions. For example, on page 418 (right column—3 Our Strategy for Design) a minibody including only the H1 and H2 CDR hypervariable regions interspersed within framework regions is described. The minibody is described as being capable of binding to a target.

Quiocho (1993), *Nature,* 362:293-4—is a further review type article that provides a summary of minibody technology (i.e., miniaturised antibodies—in this case with less than three CDRs).

Pessi et al (1993), *Nature,* 362:367-9 and Bianchi et al (1994), *J. Mol. Biol.,* 236:649-59—are papers referenced in the Vaughan and Sollazzo review and describe the H1 and H2 minibody and its properties in more detail.

Gao et al (1994), J. Biol. Chem., 269:32389-93 which describes a whole $V_L$ chain (including all three CDRs) having high affinity for its substrate, the vasoactive intestinal peptide, as evidence that it is not necessary to have both the $V_H$ and $V_L$ chains.

These documents were published before the priority date of the present application and would therefore have been available to the skilled person when implement the present invention. They provide clear evidence that molecules having fewer than all six CDRs can be capable of retaining the antigen binding properties of the antibodies for which they are derived.

In one preferred embodiment, where the binding moiety as used in the first aspect of the present invention has specificity for PSA, then the binding moiety is an antibody, or antigen-binding fragment or derivative thereof, comprising the six CDRs of exemplary anti-PSA antibody 5A10.

In an alternative embodiment, where the binding moiety as used in the first aspect of the present invention has specificity for PSA, then the binding moiety may comprise or consist of an antibody selected from the group consisting of PSA30, 4D4, 5C3, and 5A10, and antigen-binding fragments thereof.

In another embodiment of the first aspect of the present invention, the binding moiety has specificity for human glandular kallikrein (hK2).

The term hK2 is intended to include all isomeric forms of hK2, and any molecule or protein in complex with hK2. An exemplary hK2 sequence is described as Transcript: KLK2-201 (ENST00000325321), a product of gene ENSG00000167751, as given in the ensemble database which can be found at the following world-wide-web address at:

ensembl.org/*Homo_sapiens*/Transcript/Sequence_

Protein? g = ENSG00000167751;

r = 19:51376689-51383822; t = ENST00000325321 and has the following sequence:

[SEQ ID NO: 3]

```
MWDLVLSIAL  SVGCTGAVPL  IQSRIVGGWE  CEKHSQPWQV
AVYSHGWAHC  GGVLVHPQWV  LTAAHCLKKN  SQVWLGRHNL
FEPEDTGQRV  PVSHSFPHPL  YNMSLLKHQS  LRPDEDSSHD
LMLLRLSEPA  KITDVVKVLG  LPTQEPALGT  TCYASGWGSI
EPEEFLRPRS  LQCVSLHLLS  NDMCARAYSE  KVTEFMLCAG
LWTGGKDTCG  GDSGGPLVCN  GVLQGITSWG  PEPCALPEKP
AVYTKVVHYR  KWIKDTIAAN  P
```

Most of the hK2 found in seminal plasma is inactive and complexed with protein C inhibitor (PCI). It is also possible that hK2 forms complexes with other extracellular protease inhibitors. In vitro studies show that hK2 may bind to α2-antiplasmin (α2-AP), ACT, AMG, anti-thrombin III (ATIII), C1-inactivator and plasminogen activator inhibitor-1 (PAI-1).

Thus, it is also within the scope of the present invention to label compounds, molecules, proteins or any other entity, such as PCI, α2-antiplasmin (α2-AP), ACT, AMG, anti-thrombin III (ATIII), C1-inactivator and plasminogen activator inhibitor-1 (PAI-1), bound or complexed to/with hK2.

In one embodiment, the binding moiety may have specificity for the free (that is, non-complexed) isoform of hK2 compared to the complexed isoform of hK2. Binding moieties with specificity for the free isoform of hK2 may have binding specificity for an epitope that is exposed on the free isoform of hK2, but is unexposed on the complexed isoform of hK2, and this may be a linear or a conformational (that is, non-linear) epitope.

For example the binding moiety may have specificity for an epitope that includes one or more amino acid residues that are part of the catalytic cleft of hK2 that is exposed in free hK2 and unexposed in a complexed isoform, such as the form present in seminal fluid when hK2 is complexed to PCI. Epitope mapping of hK2 is described in Väisänen et al, *Clinical Chemistry* 50:9, 1607-1617 (2004), the disclosures of which are incorporated herein by reference.

Where the binding moiety as used in the first aspect of the present invention has specificity for hK2, then the binding moiety may complete for binding to hK2, or a peptide comprising the reactive epitope of h2K as bound by the binding moiety, with an antibody selected from the group consisting of 1166, and 7G1. Further discussion of such antibodies may be found in Väisänen et al, Clinical Chemistry, 50:9, 1607-1617 (2004); and Väisänen et al, *Anal. Chem.,* 78:7809-7815 (2006), the contents of each of which are incorporated herein by reference.

The amino acid sequence of the constituent heavy and light chains of the exemplary anti-hK2 antibody 11B6 is shown below (in which the CDR sequences are underlined).

11B6 Heavy chain
[SEQ ID NO: 4]
DVQLQESGPGLVKPSQSLSLTCTVTGNSIT<u>SDYAWN</u>WIRQFPGNRLEWM <u>GYISYSGSTTYSPSLKS</u>RFSITRDTSKNQFFLQLNSVTPEDTATYFCAT <u>GYYYGSGFW</u>GQGTLVTVSS 11B6 Light chain
[SEQ ID NO: 5]
DIVLTQSPASLAVSLGQRATIS<u>CRASESVEYFGTSLMH</u>WYRQKPGQPPKL LIY<u>AASNVES</u>GVPARFSGSGSGTDFSLNIQPVEEDDFSMYFC<u>QQTRKVPY</u>

TFGGGTKLEIK

In this context, the term "competes" includes the meaning that the presence of the agent comprising the binding moiety in a competitive assay along with an reference antibody selected from 11B6, and 7G1 can reduce the level of detectable binding of the reference antibody to hK2 by 1%, 2%, 3%, 4%, 5%, 10%, 20%, 30%, 40%, 50%, 60%, 70%, 80%, 90%, 95%, 99% or 100% (for example, when the agent and the reference antibody are present in the test in equimolar amounts, and optionally wherein the test is performed under physiological conditions). Such analysis can be done by an immunoradiometric assay (IRMA) as described in Example 9.

Where the binding moiety as used in the first aspect of the present invention has specificity for hK2, then the binding moiety may comprise one or more complementarity determining regions (CDRs) of an antibody selected from the group consisting of 11B6, and 7G1 (as shown by the underlined sequences in SEQ ID NOS:10 to 13 above).

It is not necessary for binding molecules to containing all six of the CDRs of any of these antibodies in order to retain the antigen binding activity, although in one embodiment the binding molecule may comprise all six CDRs from an antibody selected from the group consisting of 11B6, and 7G1.

Alternatively, the binding moiety may comprise less than six of the CDRs, such as—
- five CDRs (i.e., 3 CDRs from the $V_H$ or $V_L$ region, 2 CDRs from the other variable region);
- four CDRs (i.e., 3 CDRs from the $V_H$ or $V_L$ region, 1 CDR from the other variable region; or 2 CDRs from each of the $V_H$ and $V_L$ regions);
- three CDRs (i.e., all three CDRs from one of the $V_H$ or $V_L$ regions, and none from the other; or 2 CDRs from the $V_H$ or $V_L$ region, 1 CDR from the other variable region);
- two CDRs (i.e., two CDRs from one of the $V_H$ or $V_L$ regions, and none from the other; or 1 CDRs from each of the $V_H$ and $V_L$ regions); or
- one CDR from either of the $V_H$ or $V_L$ regions, from an antibody selected from the group consisting of 11B6, and 7G1.

In one preferred embodiment, where the binding moiety as used in the first aspect of the present invention has specificity for hK2, then the binding moiety is an antibody, or antigen-binding fragment or derivative thereof, comprising the six CDRs of exemplary anti-hK2 antibody 11B6 (see underlined sequences of SEQ ID NOs: 4 and 5).

In an alternative embodiment, where the binding moiety as used in the first aspect of the present invention has specificity for hK2, then the binding moiety may comprises or consists of an antibody selected from the group consisting of 11B6, and 7G1, and antigen-binding fragments thereof.

Optionally, the agent used in the first aspect of the present invention may further comprise a therapeutic moiety. Accordingly, the agent may comprise, or consist, of a binding moiety as described above and a therapeutic moiety. The binding moiety may be linked directly, or indirectly, to the therapeutic moiety.

In the case that the agent may comprises, or consists, of a binding moiety as described above and a therapeutic moiety then the agent may displays tumour uptake characteristics, for example as tested under the conditions used in the examples below, substantially equivalent to the tumour uptake characteristics of an agent consisting of the binding moiety alone. In this context, substantially equivalent includes the meaning of greater than 10%, 20%, 30%, 40%, 50%, 60%, 70%, 80%, 90%, 95%, 99% or substantially 100%.

Any suitable therapeutic moiety may be used. A suitable therapeutic moiety is one that is capable of reducing or inhibiting the growth, or in particular killing, a prostatic cancer cell. For example, the therapeutic agent may be a cytotoxic moiety. A cytotoxic moiety may comprise or consist of one or more radioisotopes. For example, the one or more radioisotopes may each independently selected from the group consisting of beta-emitters, Auger-emitters, conversion electron-emitters, alpha-emitters, and low photon energy-emitters. It may be desired that the one or more radioisotopes each independently has or have an emission pattern of locally absorbed energy that creates a high absorbed dose in the vicinity of the agent. Exemplary radioisotopes may include long-range beta-emitters, such as $^{90}$Y, $^{32}$P, $^{186}$Re/$^{188}$Re; $^{166}$Ho, $^{76}$As/$^{77}$As, $^{89}$Sr, $^{153}$Sm; medium range beta-emitters, such as $^{131}$I, $^{177}$Lu, $^{67}$Cu, $^{161}$Tb, $^{105}$Rh; low-energy beta-emitters, such as $^{45}$Ca or $^{35}$S; conversion or Auger-emitters, such as $^{51}$Cr, $^{67}$Ga, $^{99}$Tc$^m$, $^{111}$In, $^{114m}$In, $^{123}$I, $^{125}$I, $^{201}$Tl; and alpha-emitters, such as $^{212}$Bi, $^{213}$Bi, $^{223}$Ac, $^{225}$Ac, $^{212}$Pb, $^{255}$Fm, $^{223}$Ra, $^{149}$Tb and $^{221}$At. Further examples of therapeutic radionuclides can be seen in FIG. 9. Other radionuclides are available and will be possible to use for therapy. In another embodiment, it may be desired that the therapeutic moiety or cytotoxic moiety is not a moiety as disclosed as a "tracer" in WO 2006/087374 A1, in particular at page 11, lines 7-15 thereof.

In one preferred embodiment, the therapeutic moiety is $^{177}$Lu. For example, the agent may be an $^{111}$Lu-labelled form of anti-hK2 antibody 11B6, or of an antigen-binding fragment or derivative thereof.

Alternatively, the therapeutic moiety comprises or consists of one or more therapeutic (such as cytotoxic) drugs, for example, a cytostatic drug; an anti-androgen drug; cortisone and derivatives thereof; a phosphonate; a testosterone-5-α-reductase inhibitor; a boron addend; a cytokine; thapsigargin and its metabolites; a toxin (such as saporin or calicheamicin); a chemotherapeutic agent (such as an anti-metabolite); or any other therapeutic or cytotoxic drug useful in the treatment of prostatic carcinoma.

Exemplary therapeutic/cytotoxic drugs may, for example, include:
- Cytostatics, in particular those with dose-limiting side-effects, including but not limited to cyclophosamide, chlorambucil, ifosfamide, busulphane, lomustine, taxanes, estramustine phosphate and other nitrogen mustards, antibiotics (including doxorubicine, calicheamicines and esperamicine), *vinca* alkaloids, azaridines, platinum-containing compounds, endostatin, alkyl sulfonates, nitrosoureas, triazenes, folic acid analoges, pyrimidine analoges, purine analogs, enzymes, substituted urea, methyl-hydrazi ne derivatives, daunorubicin, amphipathic amines,
- Anti-androgens such as flutamide and bikalutamide and metabolites thereof;
- Cortisone and derivatives thereof;
- Phosphonates such as diphophonate and buphosphonate;
- Testosterone-5-α-reductaseinhibitors;
- Boron addends;
- Cytokines;
- Thapsigargin and its metabolites;
- Other agents used in the treatment of prostatic carcinoma.

Alternatively, the cytotoxic moiety comprises or consists of one or more moieties suitable for use in activation therapy, such as photon activation therapy, neutron activation therapy, neutron induced Auger electron therapy, synchrotron irradiation therapy or low energy X-ray photon activation therapy.

For example, with the tumor targeting agents according to the present invention there will be the potential of using synchrotron radiation (or low energy X-rays) for the advancement of radiotherapy, primarily focusing on so called photo-activation radiotherapy (PAT), in which the local energy deposition from external X-ray irradiation is enhanced in the cancer tissue by the interaction with a pre-administered, high-Z tumor-targeting agent, see FIG. 10.

The PAT treatment modality utilises monochromatic X-rays from a synchrotron source, such as provided by the ID17 biomedical beamline at the European Synchrotron Radiation Facility (ESRF) in Grenoble, and as anticipated to be available at other facilities in the future such as the new Swedish synchrotron facility, Max-IV.

As a further potential treatment modality, research on "induced Auger electron tumour therapy" is the coming European Spallation Source (ESS) in Lund, and hopefully a medical experimental station. Reactor-produced thermal and semi-thermal neutrons have for long been used for Boron-Neutron-Capture-Therapy, BNCT, both for pre-clinical experiments and for treatment of brain tumours with the induced alpha-particles and the recoil nucleus ($^7$L) that give a high locally absorbed energy. A similar approach is to use neutrons and suitable tumour-targeting molecules labelled with stable nuclei with high cross-section for neutrons. Antibodies or peptides can for instance be labelled with stable Gadolinium ($^{157}$Gd) and act as the target molecule for the neutrons that are captured by the Gd-nucleus, so called Gadolinium Neutron Capture Therapy (GdNCT). By Monte Carlo techniques, the dose distribution in the tumour and the surrounding tissues is calculated as it results from γ-photons, neutrons, nuclear recoils, as well as characteristic x-rays, internal conversion and Auger-electrons from gadolinium or other potential elements.

As discussed above, the therapeutic moiety (such as a radioisotope, cytotoxic moiety or the like) may be linked directly, or indirectly, to the binding moiety (such as an antibody or fragment thereof). Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tetraaza-cyclododecane-1,4,7,10,tetraacetic acid (DOTA), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA) and other chelating moieties. The use of such linkers may be particularly appropriate in circumstances wherein the agent comprises or consists of an antibody or fragment thereof as the binding moiety linked, via a linker, to a radioisotope as the therapeutic moiety.

One preferred linker is DTPA, for example as used in $^{177}$Lu-DTPA-11B6.

Optionally, the agent used in the first aspect of the present invention may (or may not) further comprise a detectable moiety. For example, a detectable moiety may comprise or consist of a radioisotope, such as a radioisotope selected from the group consisting of: Technetium-99m; Indium-111; Gallium-67; Gallium-68; Arsenic-72; Zirconium-89; Iodine-123, Iodine-124, Iodine-125; Thallium-201. Optionally, the agent may comprise a pair of detectable and cytotoxic radionuclides, such as $^{86}$Y/$^{90}$Y or $^{124}$I/$^{211}$At. Alternatively, the agent may comprise a radioisotope that is capable of simultaneously acting in a multi-modal manner as a detectable moiety and also as a cytotoxic moiety to provide so-called "Multimodality theragnostics". The binding moieties may thus be coupled to nanoparticles that have the capability of multi-imaging (for example, SPECT, PET, MRI, Optical, or Ultrasound) together with therapeutic capability using cytotoxic drugs, such as radionuclides or chemotherapy agents. Also included with the present invention is the possibility of treatment by hyperthermia using high frequency alternating magnetic fields and accompanied ultrasound imaging. For example, see FIG. 11.

Alternatively, the detectable moiety may comprise or consist of a paramagnetic isotope, such as a paramagnetic isotope is selected from the group consisting of: gadolinium-157; manganese-55, dysprosium-162, chromium-52; iron-56.

In the case that the agent used in the first aspect of the present invention comprises a detectable moiety, then the detectable moiety may be detectable by an imaging technique such as SPECT, PET, MRI, Optical or ultrasound imaging.

Therapeutic and detectable moieties may be conjugated or otherwise combined with the binding moiety using methods well known in the art (for example, the existing immunoconjugate therapy, gemtuzumab ozogamicin [tradename: Mylotarg®], comprises a monoclonal antibody linked to the cytotoxin calicheamicin).

In a further embodiment, the agent used according to the first aspect of the invention is used to treat prostate cancer in the form of a formulation comprising a population of agent molecules. In one option, all (or substantially all, such as greater than 90%, 95%, 99%, 99.9% or more, by weight) of the agent molecules in the population used for the treatment comprise the same therapeutic moiety. In another option, the population comprises a mixture of other agents with different therapeutic moieties. This option will give possibilities to enhance the effects of targeted radionuclide therapy using various agents such chemotherapy agents, hormonal therapy agents or other combination of therapies in which the targeting agent not only delivers therapeutically active radionuclides to tumor associated antigens but also simultaneously radiosensitizes the targeted tumor cells by triggering an intracellular signaling cascade. This option is also useful in treating the prostate cancer with a mixture of cytotoxic agents, for example, using a cocktail of alpha- and different ranges of beta-emitters, or a cocktail of radionuclides with different range, LET (linear energy transfer) and RBE (relative biological effect), for combined treatment of large tumors, micrometastases, and single tumor cells. In one embodiment, long-range emitters may be used for treatment of large tumors, and short-range emitters may be used for the treatment of smaller tumours such as micrometastases, and single tumor cells.

Optionally, the agent used in the first aspect of the present invention may (or may not) further comprises a moiety for increasing the in vivo half-life of the agent. Exemplary moieties for increasing the in vivo half-life of the agent may include polyethylene glycol (PEG), human serum albumin, glycosylation groups, fatty acids and dextran. PEG may be particularly contemplated.

In an embodiment of the invention, agents comprising a binding agent (e.g., antibody or fragment thereof) that are specific for a kallikrein protein, such as PSA or hK2, and a therapeutic agent are then injected/infused into the body. Then the agent binds to tissues that produce corresponding antigens, such as PSA or hK2. The biologic structures, to which the agent becomes bound, may be subsequently treated with a suitable agent and/or dosimetry and/or therapy evaluation imaging methods including PET/SPECT/CT/MR/Optical/Ultrasound may be used.

In some circumstances, variations in extent of attenuation of the prostatic cancer cells by the agent may directly correspond to production and concentration relations of the target kallikrein (such as PSA and hK2) in the prostatic cancer cells of the patient. These variations may be determined, for example, by the methods of WO 2006/08734, the methods of which are incorporated herein by reference, and used to obtain therapeutic information.

For example, pretherapy visualisations of PSA and hK2 antibody bindings, obtained from the imaging methods mentioned above, may be combined with the methods and uses of the present invention. From the measurement of attenuations it is possible to directly determine whether the investigated tissue is PSA producing, hK2 producing, or both. In light of this determination it will be possible to tailor the therapy to be most efficient. Thus individualized patient therapy can be achieved with pre-therapy dose planning. Guidance for individualized patient therapy can be taken from art-known therapies, such as those discussed in (1) Garkavij, et al. (2010) Cancer, 116:1084-1092; (2) Linden, et al. (1999) Clin. Cancer Res., 5:3287s-3291s; (3) Ljungberg, et al. (2003) Cancer Biother. Radiopharm., 18:99-107; (4) Minarik, et al, (2010) J. Nucl. Med., 51:1974-1978; (5) Sjogreen-Gleisner, et al. (2011) Q. J. Nucl. Med. Mol. Imaging, 55:126-154; and (6) Sjogreen, et al. (2005) Cancer Biother. Radiopharm., 20:92-97; the contents of each of which are incorporated herein by reference.

Accordingly, in one embodiment, the first aspect of the invention involves treating a patient determined to possess PSA-producing prostatic cancer cells with an agent according to the first aspect of the present invention that has specificity for PSA.

In another embodiment, the first aspect of the invention involves treating a patient determined to possess hK2-producing prostatic cancer cells with an agent according to the first aspect of the present invention that has specificity for human glandular kallikrein (hK2).

In another embodiment, the first aspect of the invention involves treating a patient determined to possess prostatic cancer cells that are both PSA-producing and hK2-producing, with an agent according to the first aspect of the present invention that has specificity for both PSA and human glandular kallikrein (hK2), or a combination of agents one of which possesses specificity for PSA and the other possessing specificity for hK2. In the case of combination therapy, the agents may be administered to the patient separately, sequentially, simultaneously, or formulated as a mixture in the same pharmaceutical composition.

The administration of an agent according to the first aspect of the present invention to a patent with prostate cancer may thus result in the binding of a kallikrein protein, such prostate-specific antigen (PSA; hk3, human kallikrein gene 3) and/or human glandular kallikrein (hK2), present on or in the prostatic cancer cells, and result in the inhibition of growth and/or death of prostatic cancer cells in the patient. For example, the agent may reduce the rate growth, and/or presence, of prostatic cancer cells in the patient by at least 10%, in particular at least 20%, 30%, 40%, 50%, 60%, 70%, 80% or 90%, and most particularly by 100% compared to the observed rate of growth, and/or presence, of prostatic cancer cells in the patient prior to the treatment. Methods of measuring the rate of growth, and/or presence, of prostatic cancer cells in a subject are known in the art.

Thus the invention provides methods for the treatment of prostate cancer.

By 'treatment' we include both therapeutic and prophylactic treatment of the patient. The term 'prophylactic' is used to encompass the use of an agent, or formulation thereof, as described herein which either prevents or reduces the likelihood of prostate cancer, or the spread, dissemination, or metastasis of localised prostate cancer in a patient or subject. The term 'prophylactic' also encompasses the use of an agent, or formulation thereof, as described herein to prevent recurrence of prostate cancer in a patient who has previously been treated for prostate cancer.

The prostate cancer to be treated by the first aspect of the present invention may be localised to the prostate, or may be a non-localised (that is, disseminated) prostate cancer. Prostate cancer localised to the prostate may, for example, be classified as clinical T1 or T2 cancers according to the TNM system (abbreviated from Tumor/Nodes/Metastases) whereas non-localised/disseminated prostate cancer may, for example, be classified as clinical T3 or T4 cancers.

The prostate cancer to be treated by the first aspect of the present invention may be metastatic prostate cancer. Metastasis refers to the spread of a cancer from its original location to other sites in the body. For example, the metastatic prostate cancer to be treated may be a metastases present in the lymphatic system; in bone (including spine, vertebrae, pelvis, ribs); metastasis within pelvis, rectum, bladder, or urethra. Metastases present at other less common locations can also be treated with the present invention. The metastases may be micrometastases. Micrometastase is a form of metastases in which the newly formed tumors are generally too small to be detected, or detected with difficulty. For example, the present invention provides the skilled person with means to treat single cancer cells or cell clusters, even if the presence of such cells or clusters are not possible to diagnose but exist, for example as occult disseminated disease.

Accordingly, it is anticipated that a particularly important technical advantage of the treatment provided by the present invention compared to the prior art treatments of prostate cancer is the enhanced efficacy in treatment of disseminated and/or metastatic (including micrometastatic) prostate cancer.

Thus, in one embodiment, the invention provides agents and methods for preventing or treatment metastasis of a primary prostate tumour.

Prostate cancer tends to develop in men over the age of fifty, more commonly in men over 60, 65 or 70, and although it is one of the most prevalent types of cancer in men, many never have symptoms, undergo no therapy, and eventually die of other causes. This is because cancer of the prostate is, in most cases, slow-growing, symptom-free, and since men with the condition are older they often die of causes unrelated to the prostate cancer, such as heart/circulatory disease, pneumonia, other unconnected cancers, or old age. About two-thirds of prostate cancer cases are slow growing, the other third more aggressive and fast developing.

Accordingly, the development of effective treatments of prostate cancer is particularly important for management of more aggressive and fast developing forms of the cancer, particularly in younger patient. Accordingly, in one embodiment, the first aspect of the invention relates to the treatment of prostate cancer in a patient this is less than 70, 65, 60, 55, 50, 45, 40 or less years old at the time of diagnosis of prostate cancer and/or at the time of treatment.

Men who have a first-degree relative (father or brother) with prostate cancer are thought to have twice the risk of developing prostate cancer, and those with two first-degree relatives affected are thought to have a five-fold greater risk compared with men with no family history. Accordingly, the first aspect of the invention may relates to the treatment of prostate cancer in a patient that is characterised in that one, two, or more, family members, in particular first-degree family members (such as a father or brother), has been previously been diagnosed with prostate cancer.

The first aspect of the invention also relates to the treatment of prostate cancer in a patient, wherein the prostate cancer to be treated is castration-resistant prostate cancer (CRPC). CRPC may be characterised by typically becoming refractory to hormone treatment after one to three years, and resuming growth despite hormone therapy.

The present invention also provides a pharmaceutical composition comprising a therapeutically effective amount of an agent as defined above in respect of the first aspect of the present invention and a pharmaceutically-acceptable diluent, carrier or excipient.

Additional compounds may also be included in the pharmaceutical compositions, including, chelating agents such as EDTA, citrate, EGTA or glutathione.

The pharmaceutical compositions may be prepared in a manner known in the art that is sufficiently storage stable and suitable for administration to humans and animals. For example, the pharmaceutical compositions may be lyophilised, e.g., through freeze drying, spray drying, spray cooling, or through use of particle formation from supercritical particle formation.

By "pharmaceutically acceptable" we mean a non-toxic material that does not decrease the effectiveness of the kallikrein protein-binding activity of the agent of the invention. Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000), he disclosures of which are incorporated herein by reference).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the agent in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the agent of the invention. The adjuvant may be one or more of zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition. The adjuvant may also be cationic polymers such as cationic cellulose ethers, cationic cellulose esters, deacetylated hyaluronic acid, chitosan, cationic dendrimers, cationic synthetic polymers such as poly(vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, glucose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethyl hydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The agents of the invention may be formulated into any type of pharmaceutical composition known in the art to be suitable for the delivery thereof.

In one embodiment, the pharmaceutical compositions of the invention may be in the form of a liposome, in which the agent is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871, the disclosures of which are incorporated herein by reference.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(carprolactone) (PCL), and polyanhydrides have been widely used as biodegradable polymers in the production of microspheres. Preparations of such microspheres can be found in U.S. Pat. No. 5,851,451 and in EP 0 213 303, the disclosures of which are incorporated herein by reference.

In a further embodiment, the pharmaceutical compositions of the invention are provided in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polyvinyl imidazole, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the agent. The polymers may also comprise gelatin or collagen.

Alternatively, the agents may simply be dissolved in saline, water, polyethylene glycol, propylene glycol, ethanol or oils (such as safflower oil, corn oil, peanut oil, cottonseed oil or sesame oil), tragacanth gum, and/or various buffers.

It will be appreciated that the pharmaceutical compositions of the invention may include ions and a defined pH for potentiation of action of the active agent. Additionally, the compositions may be subjected to conventional pharmaceutical operations such as sterilisation and/or may contain conventional adjuvants such as preservatives, stabilisers, wetting agents, emulsifiers, buffers, fillers, etc.

The pharmaceutical compositions according to the invention may be administered via any suitable route known to those skilled in the art. Thus, possible routes of administration include parenteral (intravenous, subcutaneous, and intramuscular), topical, ocular, nasal, pulmonar, buccal, oral, parenteral, and rectal. Also administration from implants is possible. Infusion may be a desired route because of the potentially high cytotoxicity of the administered agent.

In one embodiment, the pharmaceutical compositions are administered parenterally, for example, intravenously, intracerebroventricularly, intraarticularly, intra-arterially, intraperitoneally, intrathecally, intraventricularly, intrasternally, intracranially, intramuscularly or subcutaneously, or they may be administered by infusion techniques. They are conveniently used in the form of a sterile aqueous solution which may contain other substances, for example, enough salts or glucose to make the solution isotonic with blood. The aqueous solutions should be suitably buffered (for example, to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Thus, the pharmaceutical compositions of the invention are particularly suitable for parenteral, e.g., intravenous, administration.

Alternatively, the pharmaceutical compositions may be administered intranasally or by inhalation (for example, in the form of an aerosol spray presentation from a pressurised container, pump, spray or nebuliser with the use of a suitable propellant, such as dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas). In the case of a pressurised aerosol, the dosage unit may be determined by providing a valve to deliver a metered amount. The pressurised container, pump, spray or nebuliser may contain a solution or suspension of the active polypeptide, e.g., using a mixture of ethanol and the propellant as the solvent, which may additionally contain a lubricant, e.g., sorbitan trioleate. Capsules and cartridges (made, for example, from gelatin) for use in an inhaler or insufflator may be formulated to contain a powder mix of a compound of the invention and a suitable powder base such as lactose or starch.

The pharmaceutical compositions will be administered to a patient in a pharmaceutically effective dose. A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e., a carrier or administration vehicle. Further, it is intended to mean an amount sufficient to reduce and/or prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical worker based on patient characteristics, such as age, weight, sex, condition, complications, other diseases, etc., as is well known in the art. The administration of the pharmaceutically effective dose can be carried out both by single administration in the form of an individual dose unit or else several smaller dose units and also by multiple administrations of subdivided doses at specific intervals. Alternatively, the does may be provided as a continuous infusion over a prolonged period.

The agent defined above in respect of the first aspect of the present invention can be formulated at various concentrations, depending on the efficacy/toxicity of the compound being used. The formulation may comprises the active agent at a concentration of between 0.1 µM and 1 mM, between 1 µM and 500 µM, between 500 µM and 1 mM, between 300 µM and 700 µM, between 1 µM and 100 µM, between 100 µM and 200 µM, between 200 µM and 300 µM, between 300 µM and 400 µM, between 400 µM and 500 µM and about 500 µM.

It will be appreciated by persons skilled in the art that the pharmaceutical compositions of the invention may be administered alone or in combination with other therapeutic agents used in the treatment of a prostate cancer, or before, after or at the same time as the treatment of the patient with other therapeutic modalities for the treatment of prostate cancer, such as surgery (e.g., radical prostatectomy), radiation therapy, brachytherapy, external beam radiation therapy, high-intensity focused ultrasound (HIFU), chemotherapy, oral chemotherapeutic drugs, cryosurgery (freezing the tumour), hormonal therapy (such as antiandrogen therapy), castration or combinations of the foregoing.

The present invention also provides a kit comprising an agent as defined above in respect of the first aspect of the present invention or a pharmaceutical composition as defined above.

The present invention also provides an agent for use in medicine substantially as described herein.

The present invention also provides a pharmaceutical composition substantially as described herein.

The present invention also provides for the use of an agent substantially as described herein.

The present invention also provides a method of treatment substantially as described herein.

The present invention also provides a kit substantially as defined herein.

According to one aspect of the invention, a therapeutic method is provided, which method treat primary and disseminated prostate cancer, with an agent as defined above.

According to another aspect of the invention, a therapy method is provided, which method may be used to treat metastasis, such as lymph gland metastasis and/or bone metastases, including micrometastases.

According to yet another aspect of the invention, a therapeutic method is provided, which method may be used to together with or after external radiotherapy, cytostatic, and androgen treatments, or other treatments not coupled to tumor targeting therapeutic antibodies/fragments.

According to specific aspects of the invention, therapy-labelled antibodies, that are specific for PSA and/or hK2, are provided, which labelled antibodies are used to treat prostate cancer, i.e., PSA and/or hK2 producing tissue.

According to another aspect of the invention, uses of said methods are provided.

The therapy method according to the present invention has the advantage over the prior art that it allows for therapy of prostate cancer, and said therapy method may also be used to treat metastasis, including micrometastases, such as lymph gland metastasis, or any of the other forms of metastasis as described above, and be used together with or after post operative procedure, and during or after radiation, cytostatic, and androgen treatments.

The foregoing description focuses on embodiments of the present invention applicable to a therapeutic method of prostatic cancer. However, it will be appreciated that the invention is not limited to this application but may be applied to many other therapy combinations including for example metastasis, post operative examinations, and examinations during or after radiation, cytostatic, and androgen treatments. In respect of therapy of metastasis the metastases will be treated in lymph glands.

In another embodiment RadioGuided Surgery (RGS) or Image-Guided Surgery (IGS) may be used to identify tracer-labeled anti-kallikrein specific binding moieties as described above (such as PSA and/or hK2-antibodies) during and/or before surgery. Thus, an agent comprising a binding moiety and a detectable moiety as discussed above may be administered during and/or before surgery. In this embodiment the agent, such as a tracer labeled anti-PSA and/or anti-hK2-antibody, may be first infused. Thereafter, RGS/IGS may be used to identify PSA/hK2 producing tissue with a detection instrument sensitive to the detectable moiety, during or before surgery. The detectable moiety may, for example, be a radiation emitting or magnetic-sensitive detectable moiety; it may, for example, be an emitter of Cerenkov radiation and/or Bremsstrahlung; it may be a fluorescent label and/or a magnetic or magentizable label. Accordingly, the RGS/IGS according to the present invention may, for example, be a method that is based on the detection of optical, Cerenkov, Bremsstrahlung, or beta radiation; the detection of a radionuclide label, and/or may involve magnetometry. RGS is well known to the person skilled in the art as a surgical technique that enables the surgeon to identify tissue "marked" by the detectable moiety.

The visualisations obtained according to above may be combined with other radiological visualisation methods, such as SPECT/PET, computed tomography (CT), ultrasound (US), and magnetic resonance tomography (MRT).

Accordingly, in a second aspect, the present invention also provide an agent comprising or consisting of a binding moiety with specificity for a kallikrein protein (such as described above in respect of the first aspect of the present invention) and a detectable moiety as discussed above in respect of the first aspect of the present invention for use in medicine by administration to a patient with prostate cancer before or during the surgery, such as RadioGuided or Image-Guided Surgery.

Thus, the second aspect also provides for the use of an agent comprising or consisting of a binding moiety with specificity for a kallikrein protein and a detectable moiety in the manufacture of a medicament for administration to a patient with prostate cancer before or during the surgery, such as RadioGuided or Image-Guided Surgery.

The second aspect of the present invention also provides a method surgery, such as RadioGuided or Image-Guided Surgery, that is performed on a patient with prostate cancer, the method comprising the step of administering an effective amount of an agent comprising or consisting of a binding moiety with specificity for a kallikrein protein and a detectable moiety to the patient before or during the surgery.

It is contemplated that any method, agent or composition described herein can be implemented with respect to any other method, agent or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the above description and the accompanying drawings. It should be understood, however, that the above description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

The following drawings form part of the present specification and are included to further demonstrate certain aspects of the present invention. The invention may be better understood by reference to one or more of these drawings in combination with the detailed description of specific embodiments presented herein.

FIG. 3 shows Tumor-to-Organs ratios of $^{125}$I-PSA30 after intravenous injection in nude mice bearing LNCaP-based subcutaneous tumors at various times after injection (n=34). Higher ratio values indicate a greater specificity of uptake in tumour than in the identified tissue.

FIGS. 4A-4H shows the results of digital autoradiography: Individually normalized uptake of $^{125}$I-PSA30 (FIG. 4A) and $^{18}$F-choline (FIG. 4B), 48 h post injection of $^{125}$I-PSA30 plus 1 h post injection of labeled-choline, in the same tumor section separated by isotope. Histological analysis via H&E (FIG. 4C, FIGS. 4E-4F) and PSA expression using 2E9 total PSA antibody (FIG. 4D, FIGS. 4G-4H) were verified using adjacent sections. There is no direct association between areas of high PSA30 mAb uptake and high choline uptake. Note: this mouse was allowed free movement after injection of 18F-choline. 209×297 mm (300×300 DPI)

Figure 5:
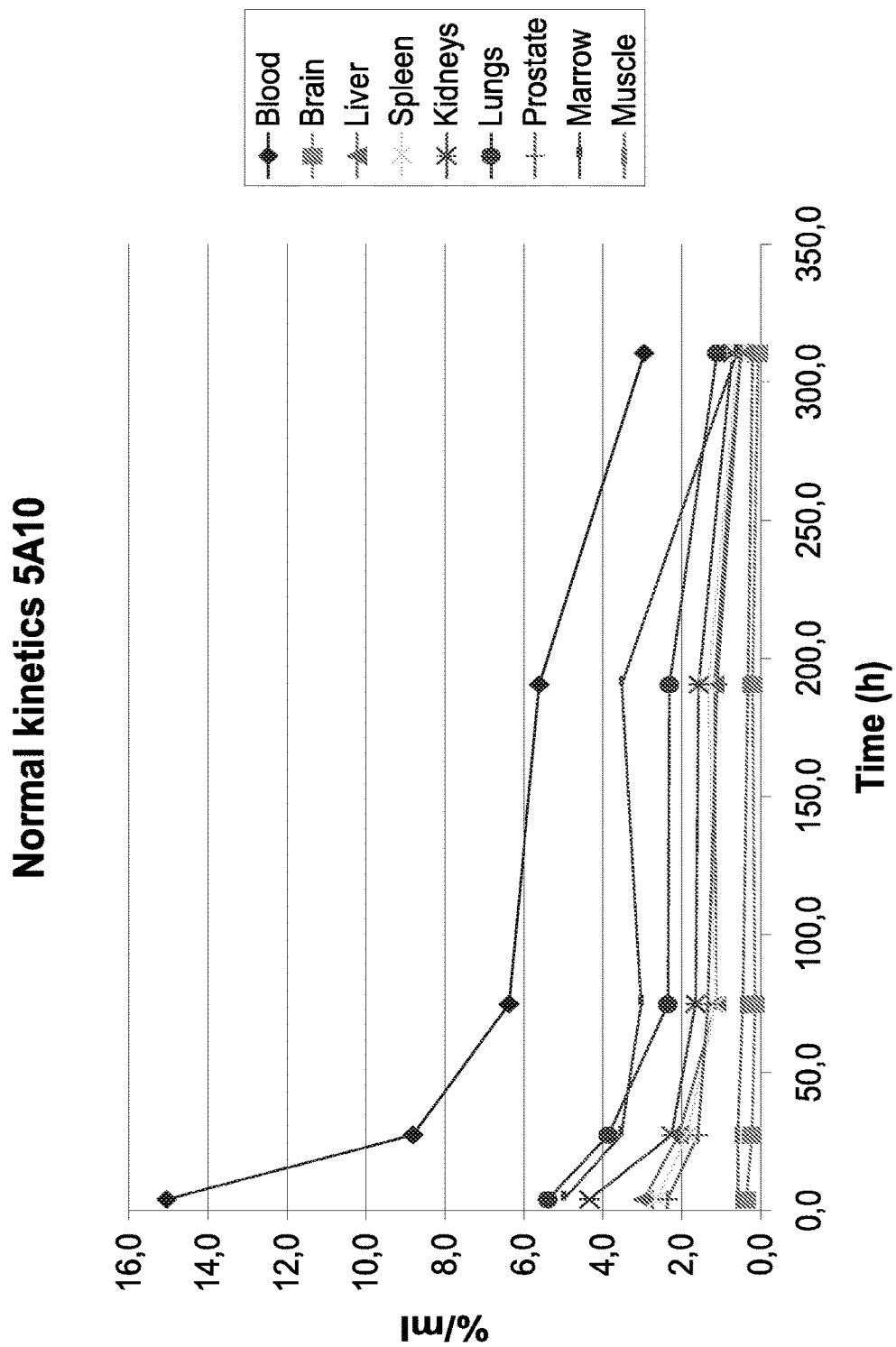

FIG. 5 shows the kinetics of $^{125}$I-labelled 5A10 antibody in various tissues following intravenous administration in normal mice.

Figure 6:
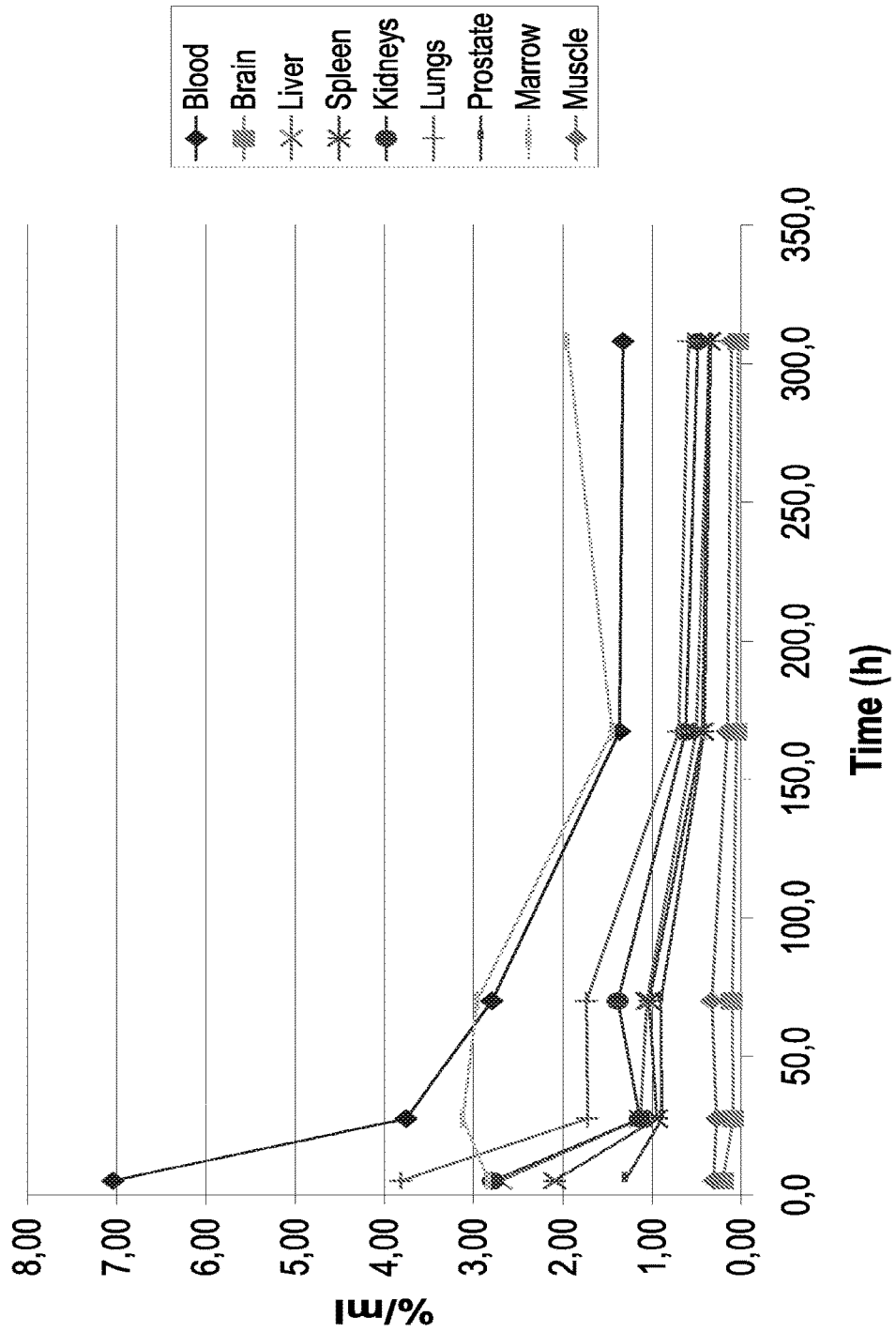

FIG. 6 shows the kinetics of $^{125}$I-labelled 11B6 antibody in various tissues following intravenous administration in normal mice.

Figure 7:
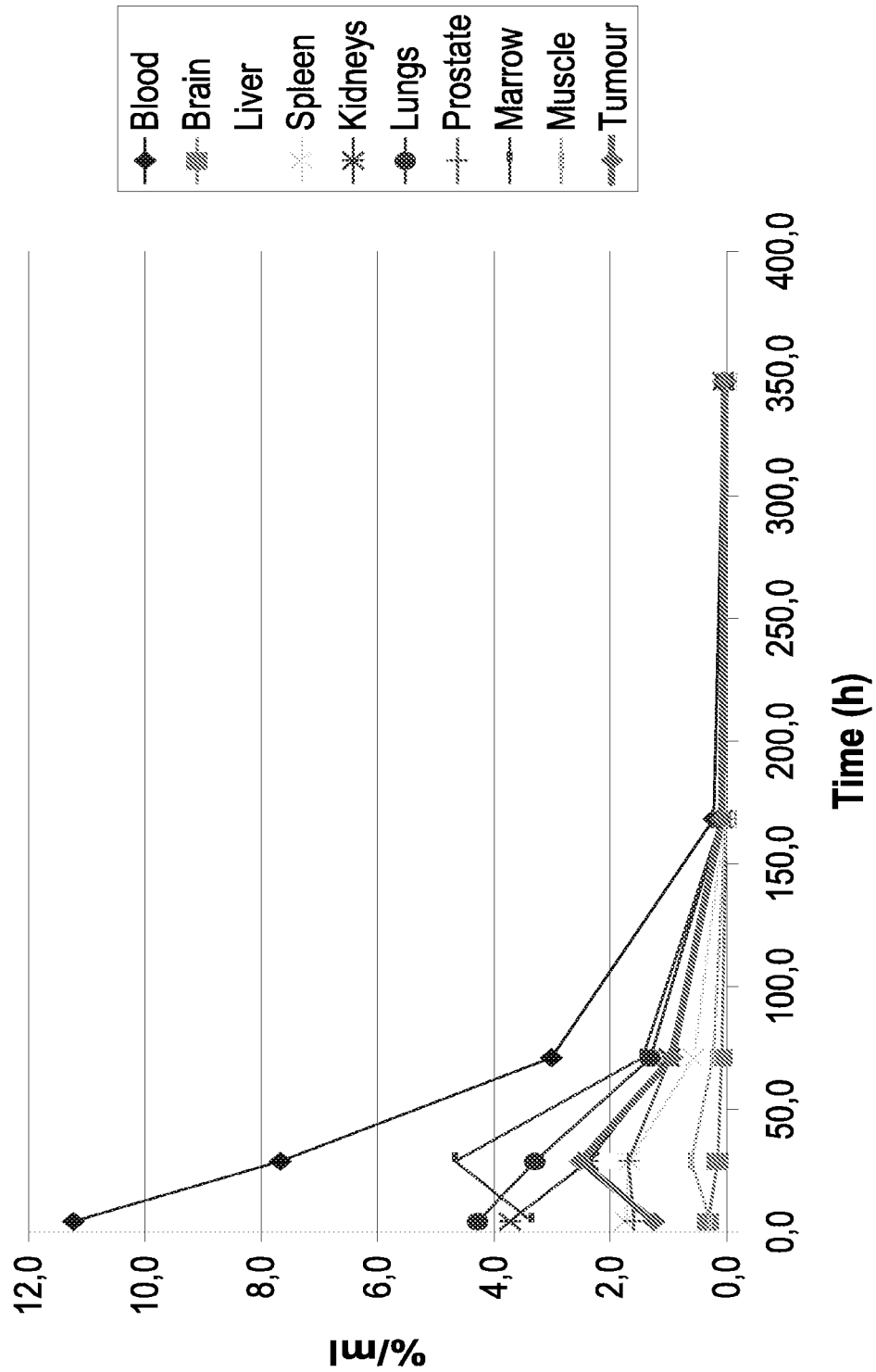

FIG. 7 shows the kinetics of $^{125}$I-labelled 11B6 antibody in various tissues following intravenous administration in mice implanted with xenograft of metastatic prostate tumour cells. Organ uptake expressed as % IA/g over time.

Figure 8:
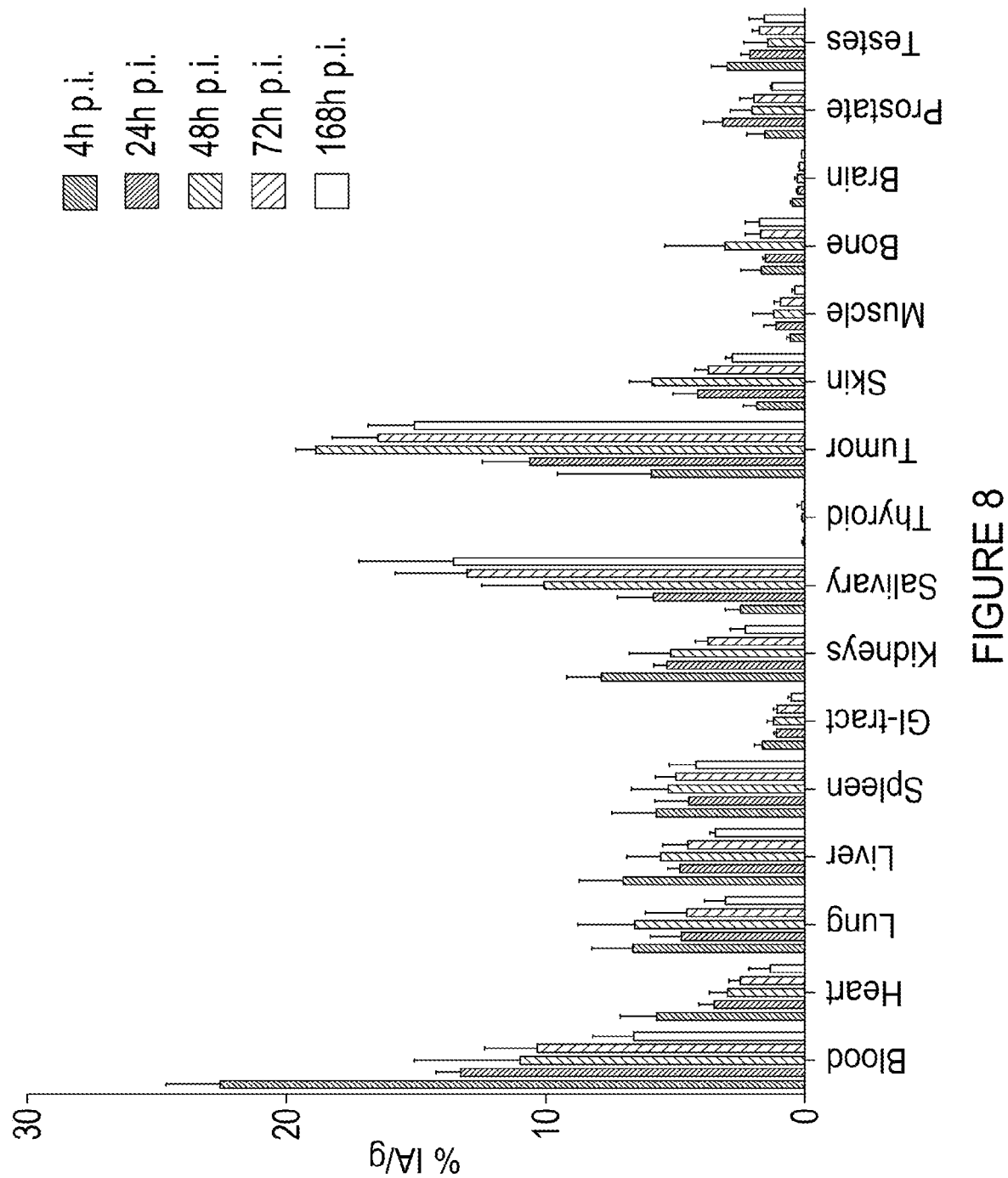

FIG. 8 shows the biodistribution of $^{111}$In-11B6 in LnCAP xenografts. Accumulation of radioactivity peaked after 48 hpi with 16.4±1.92% IA/g (percent injected activity per gram). Uptake in normal organs (liver, spleen, kidneys, bone, prostate, testes) are at a lower level. Somewhat elevated uptake was observed in the salivary glands, likely due to a certain normal expression of hK2 expression.

Figure 9:
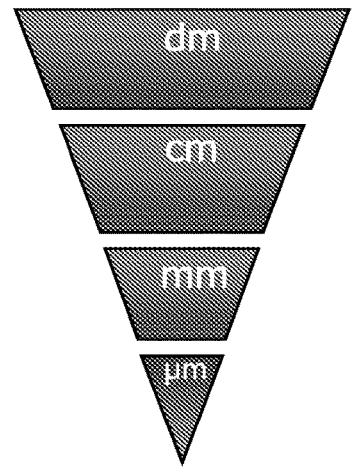

FIG. 9 shows examples of some therapeutic radionuclides.

Figure 10:
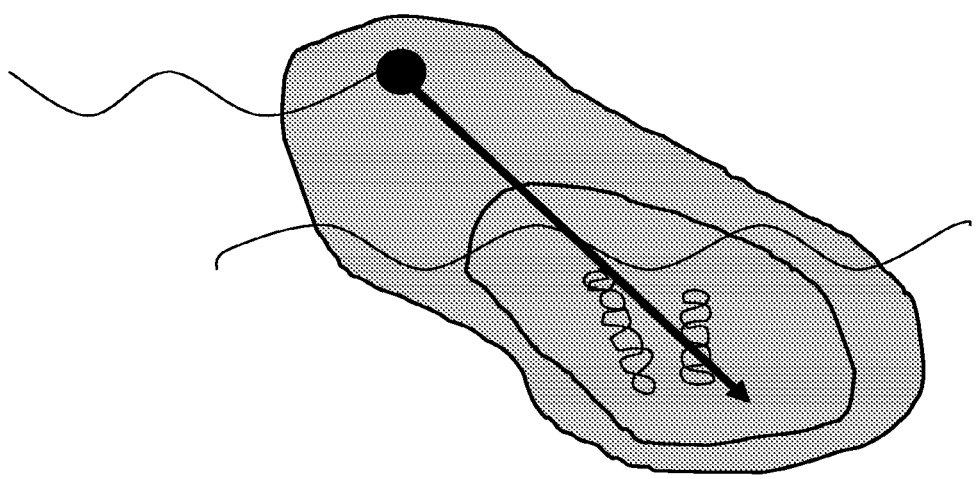

FIG. 10 shows an illustration of the principle of PAT. In the presence of low-dose external radiation, a high Z tumour-targeting agent produces a large local absorbed dose enhancement in targeted tumour cells.

Figure 11:
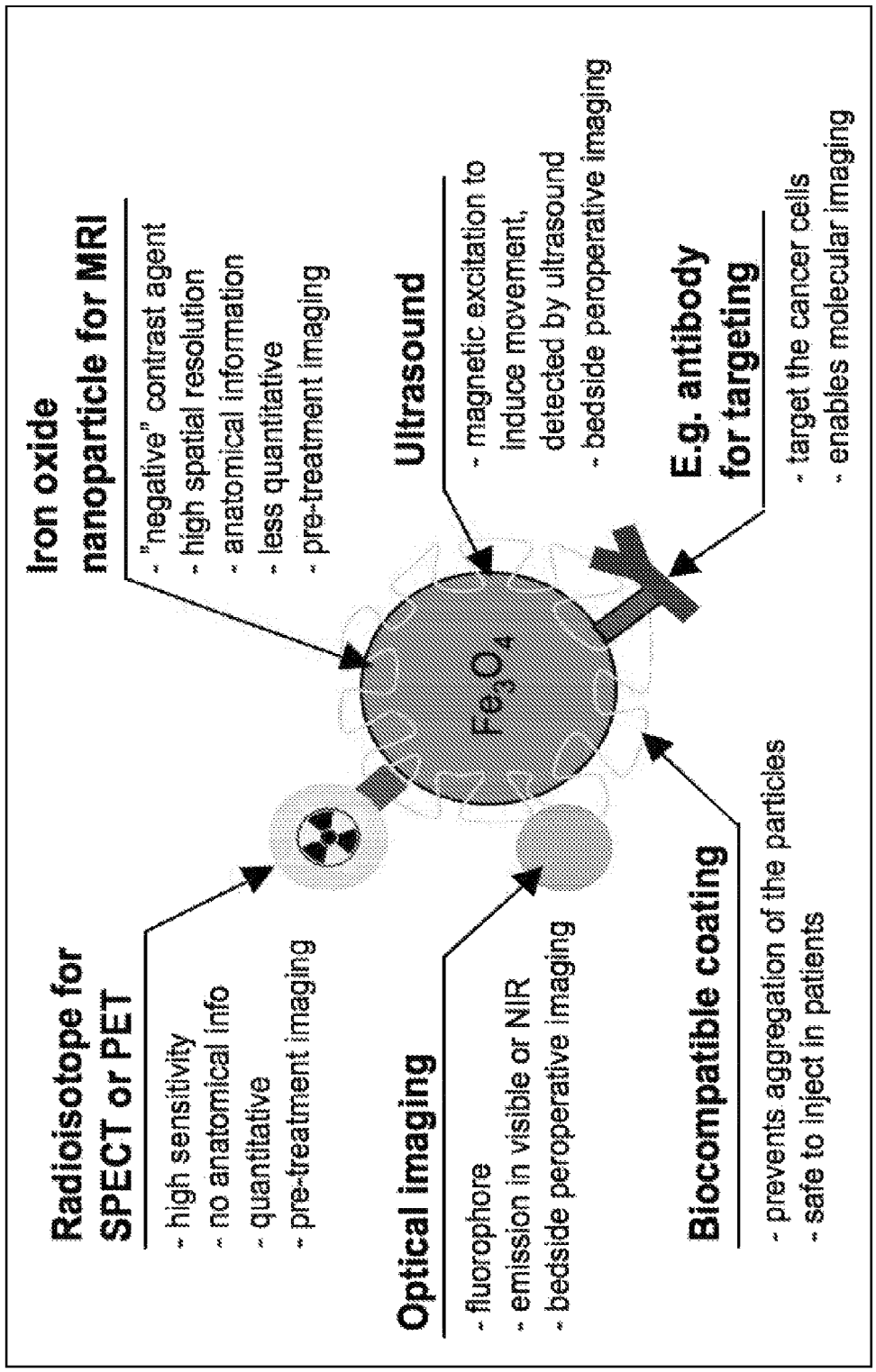

FIG. 11 shows an example of how nanoparticles can be used for multimodality imaging and therapy by attachment to tumor targeting agents as antibodies.

Figure 12:
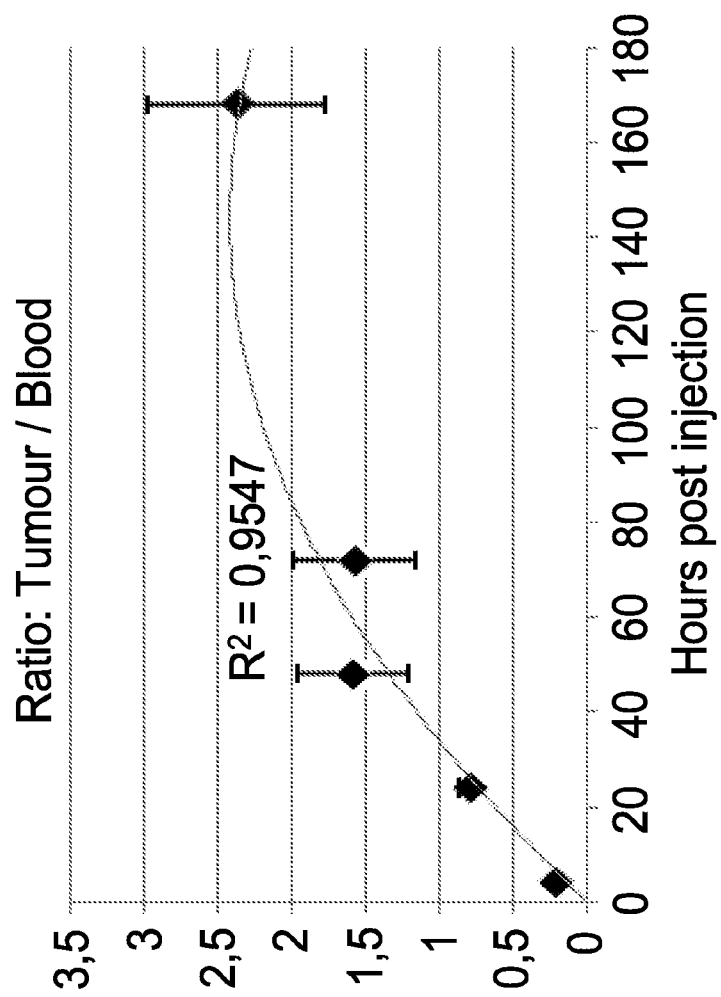

FIG. 12 shows the tumor/blood ratios. The ratio increases over time, indicating an active targeting of hK2 with $^{111}$In-11B6 in LnCAP tumors.

Figure 13:
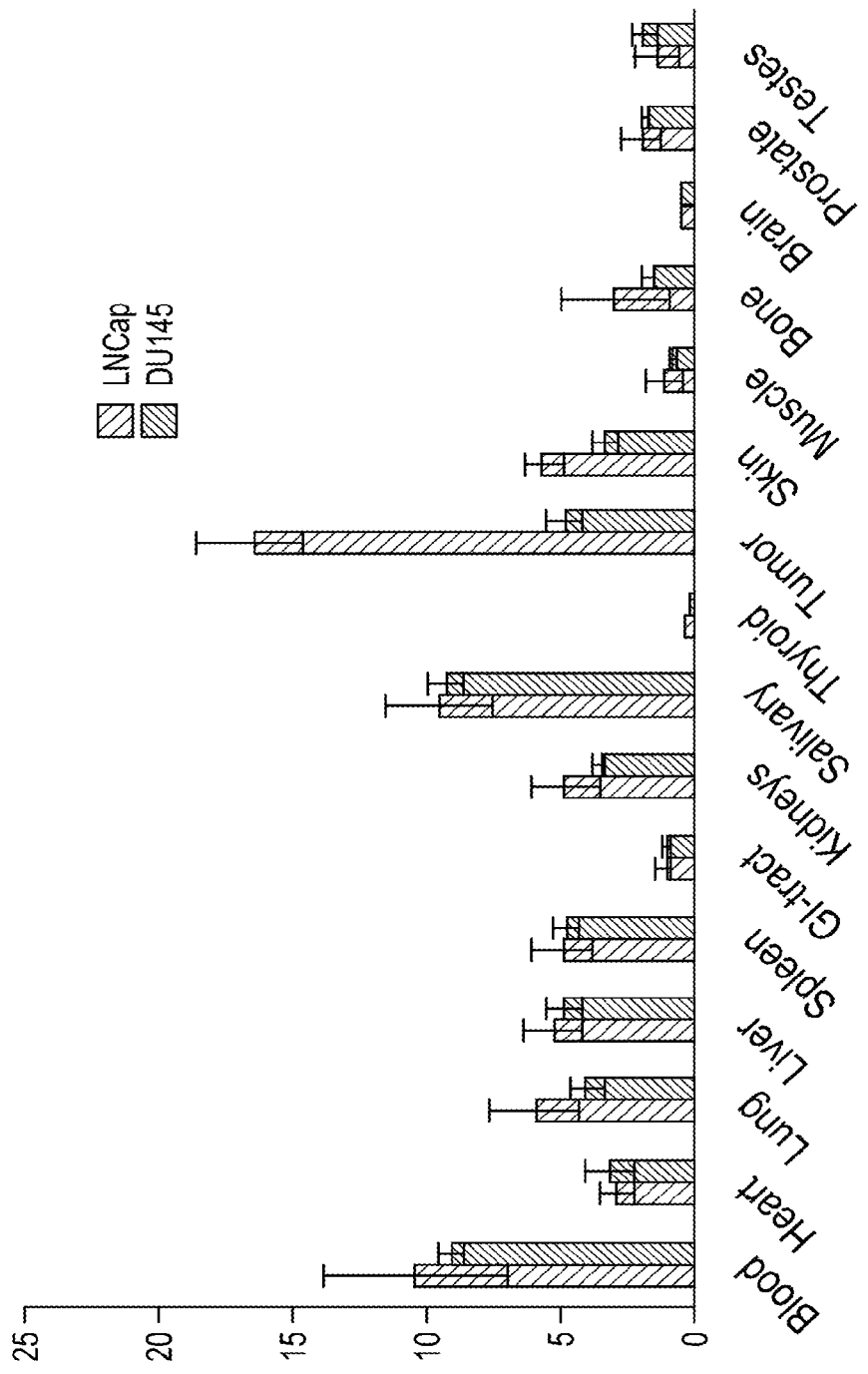

FIG. 13 shows the comparative biodistribution of $^{111}$In-11B6 in hK2-expressing xenografts (LnCAP) and hK2-negative xenografts (DU145) at 48 hpi. Results showed a statistical significant difference (p<0.005) between the two xenografts in the tumor accumulation, while the radioactivity accumulation in most normal organs remained on the same level. LnCAP had more than 3-fold higher tumor uptake than the DU145. This indicates that the $^{111}$In-11B6 is hK2-specific.

FIG. 14 shows the amino acid sequence and epitope structure of PSA, according to Leinonen, J. et al. *Clin Chem* 2002; 48:2208-2216.

FIG. 15 shows a Scatchard's plot of an exemplary 5A10-Fab.

Figure 16:
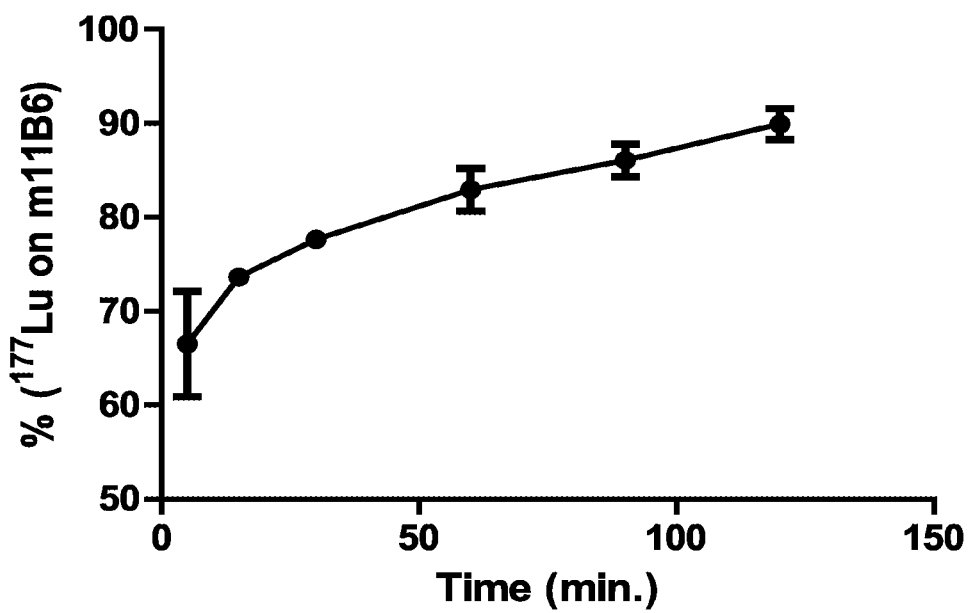

FIG. 16 shows the labelling kinetics of $^{177}$Lu-11B6.

Figure 17:
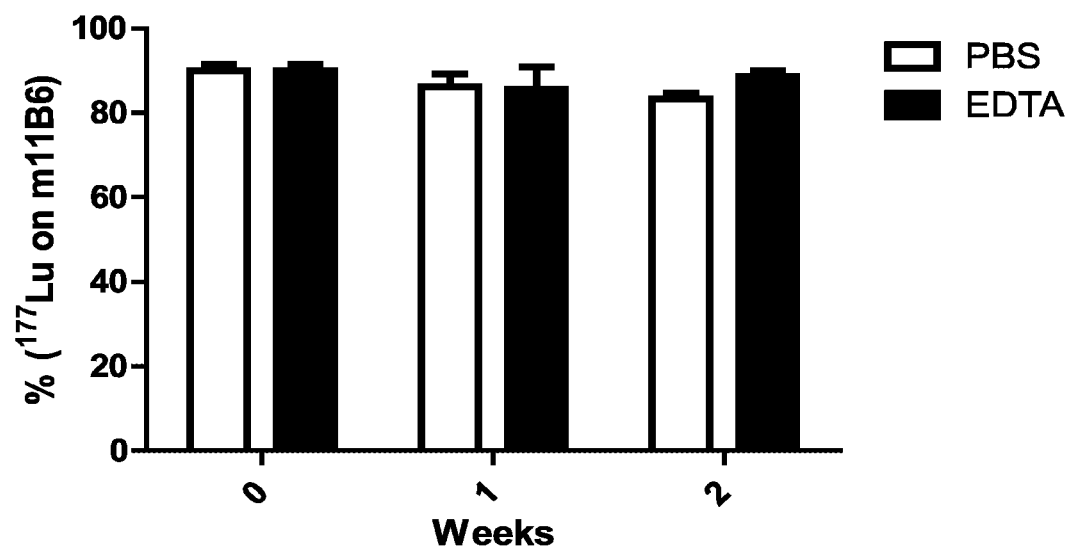

FIG. 17 shows the in vitro stability of $^{17}$Lu-11B6 in PBS and EDTA.

Figure 18:
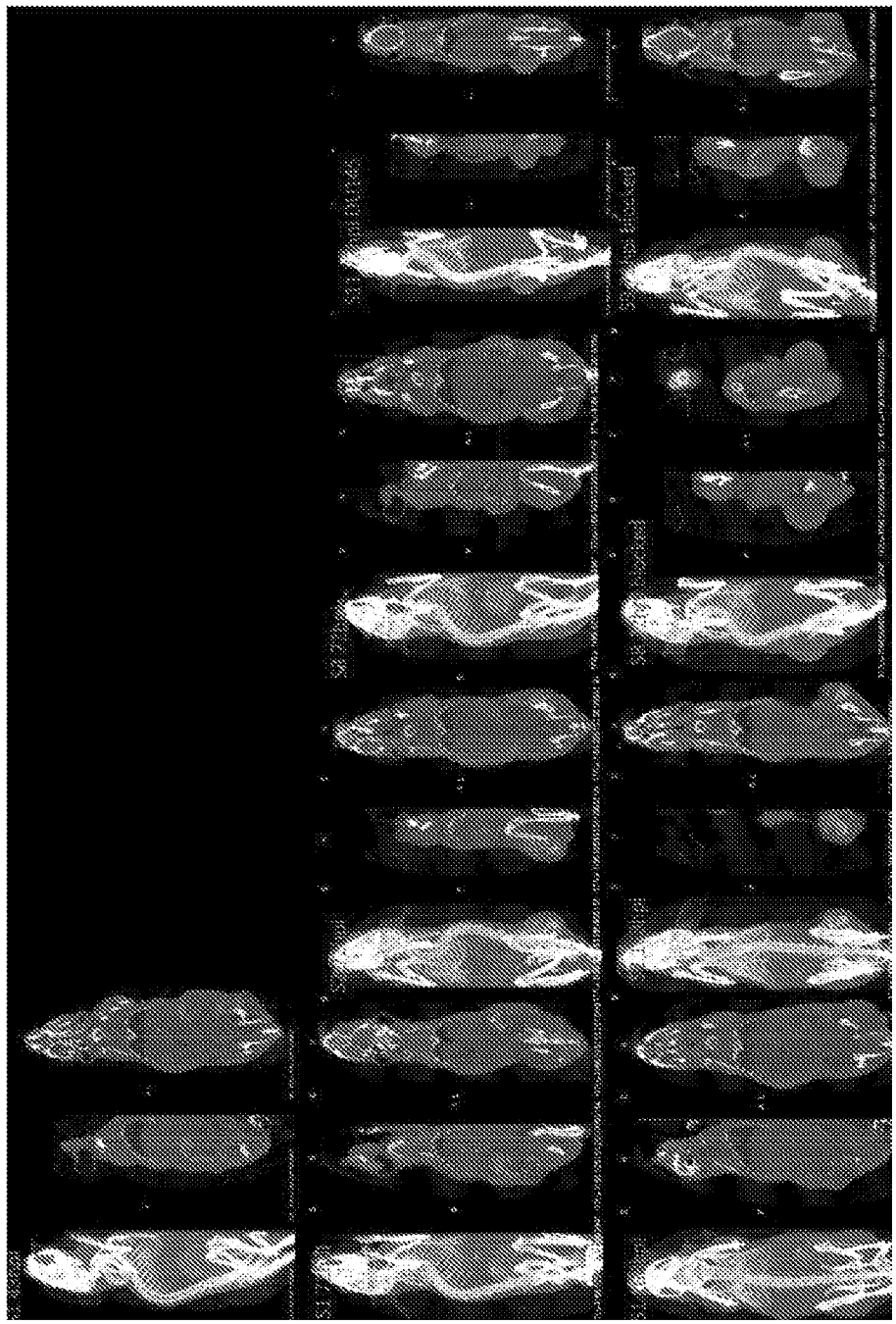

FIG. 18 shows representative SPECT images of $^{177}$Lu-11B6 in LnCAP xenografts.

Figure 19:
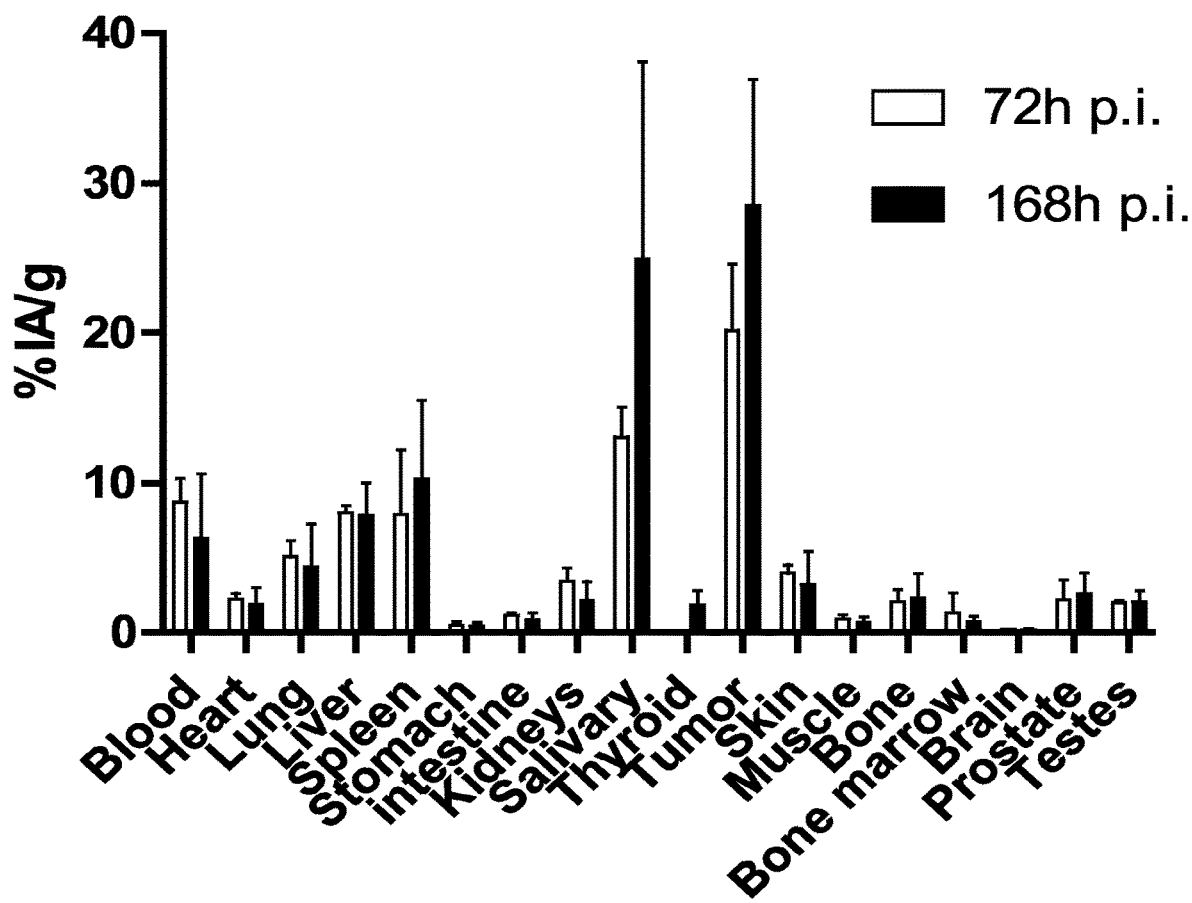

FIG. 19 shows the biodistribution of $^{177}$Lu-11B6 in LnCAP xenografts.

Figure 20:
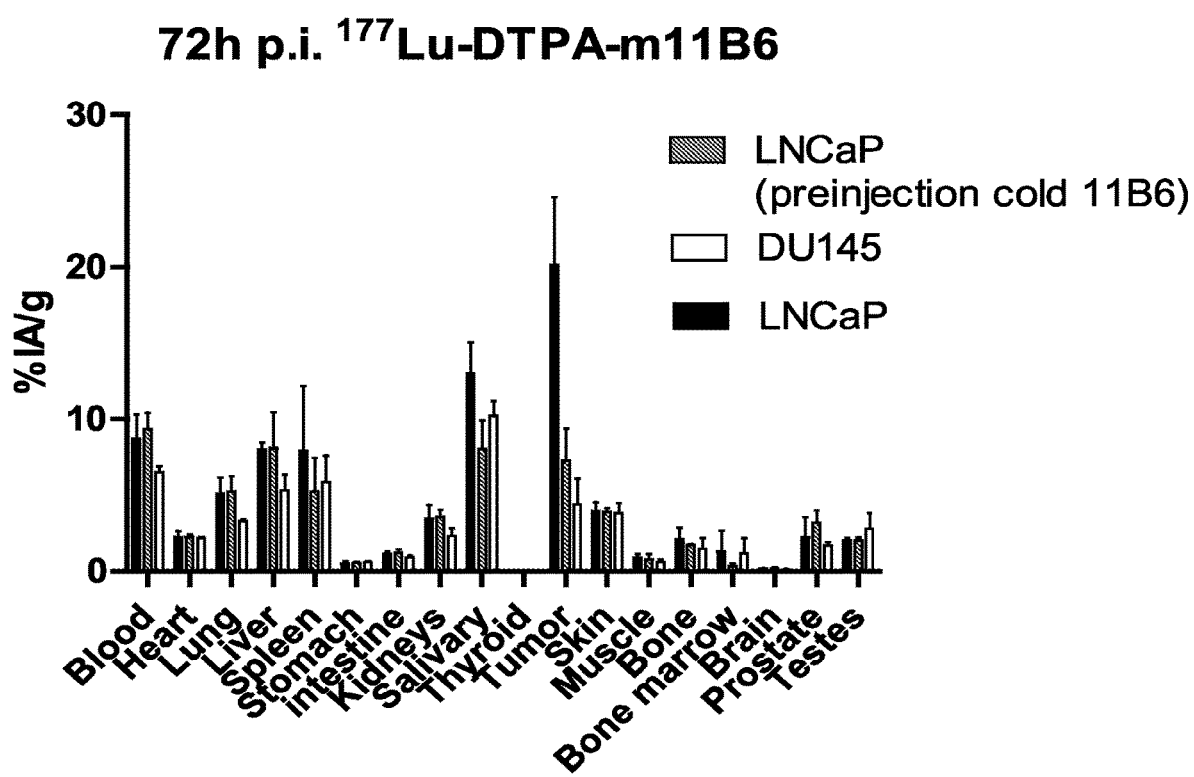
Figure 21:
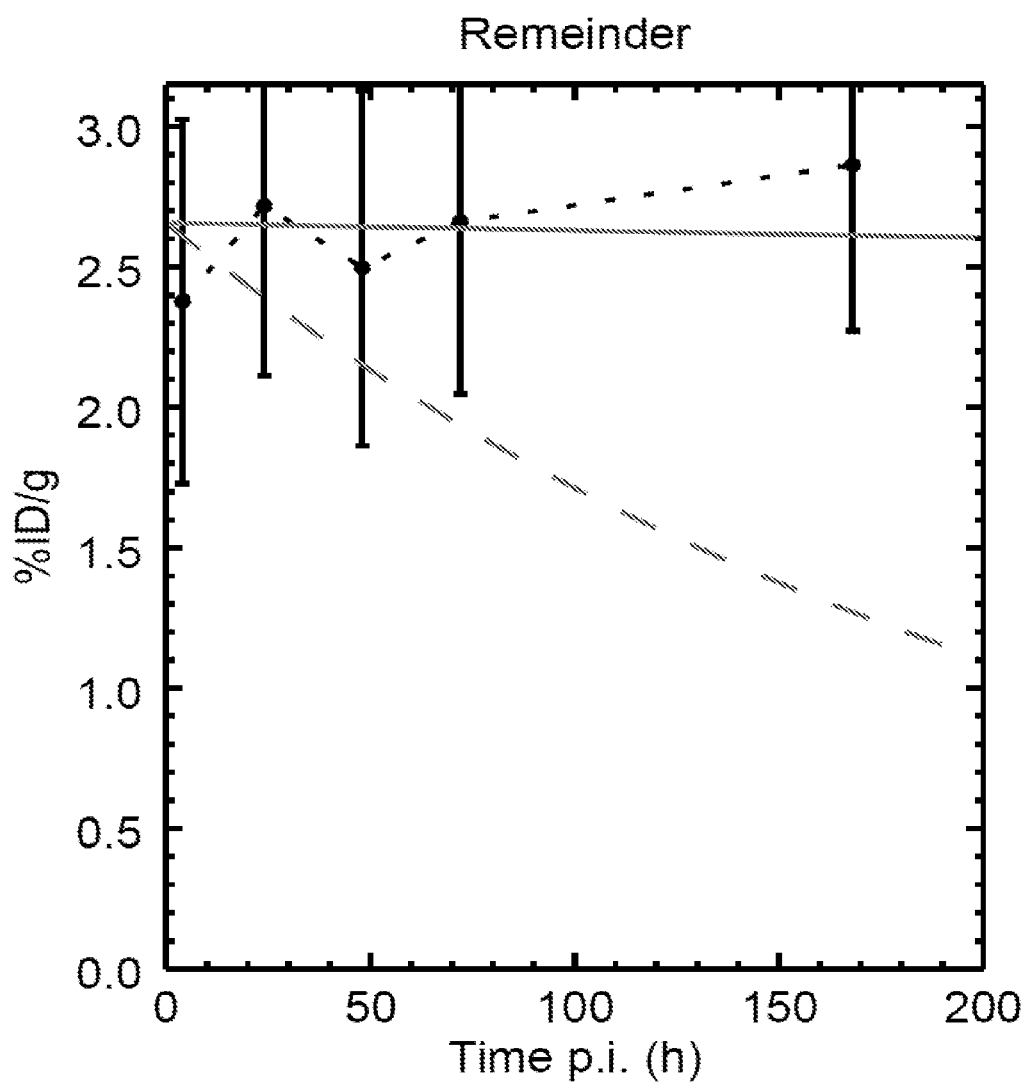
Figure 21:
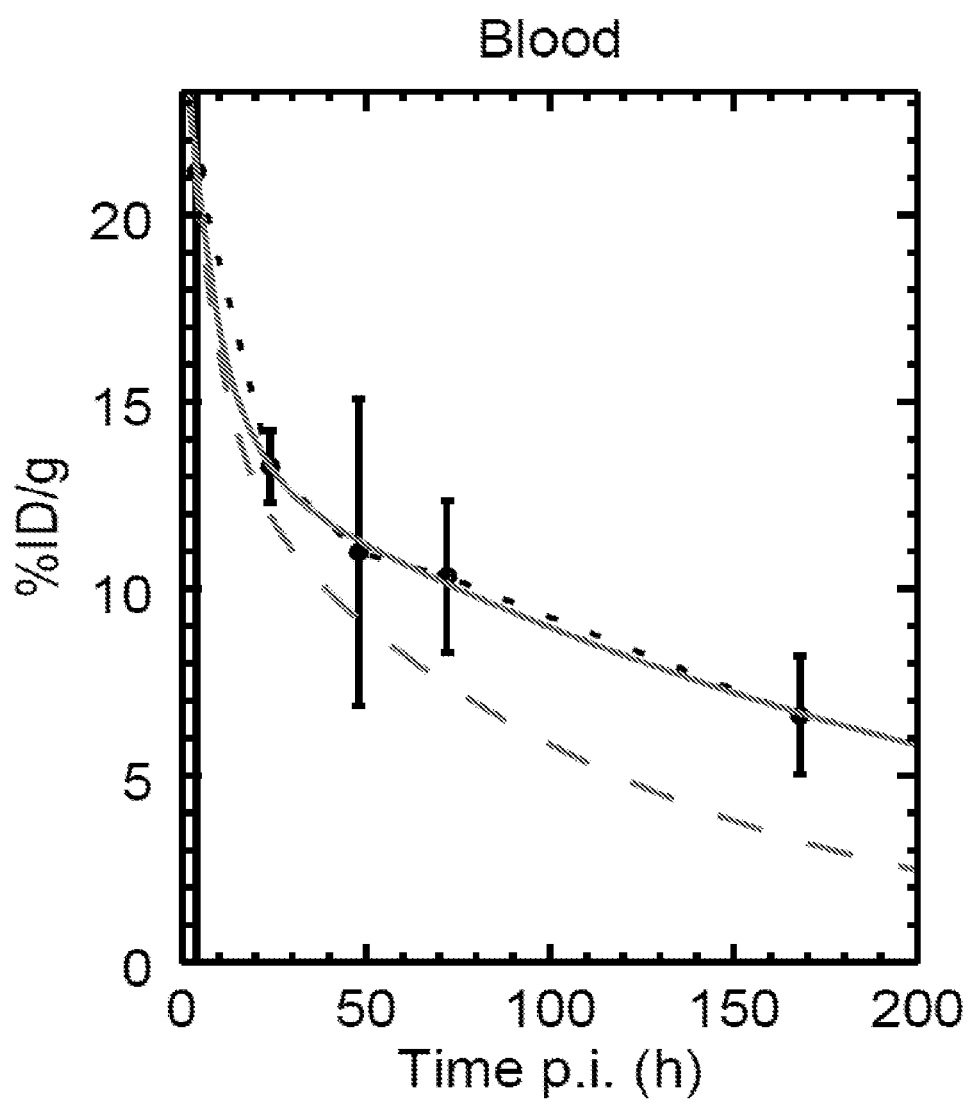
Figure 21:
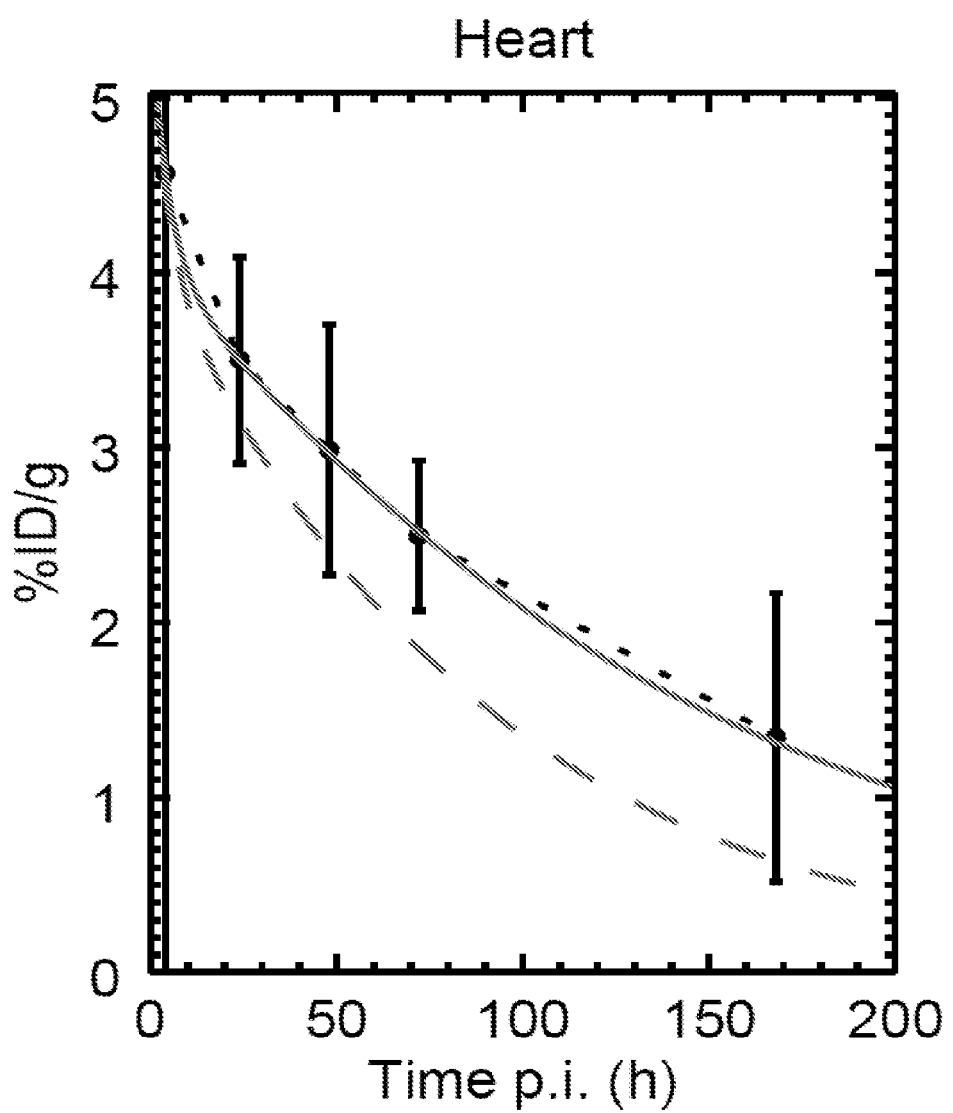
Figure 21:
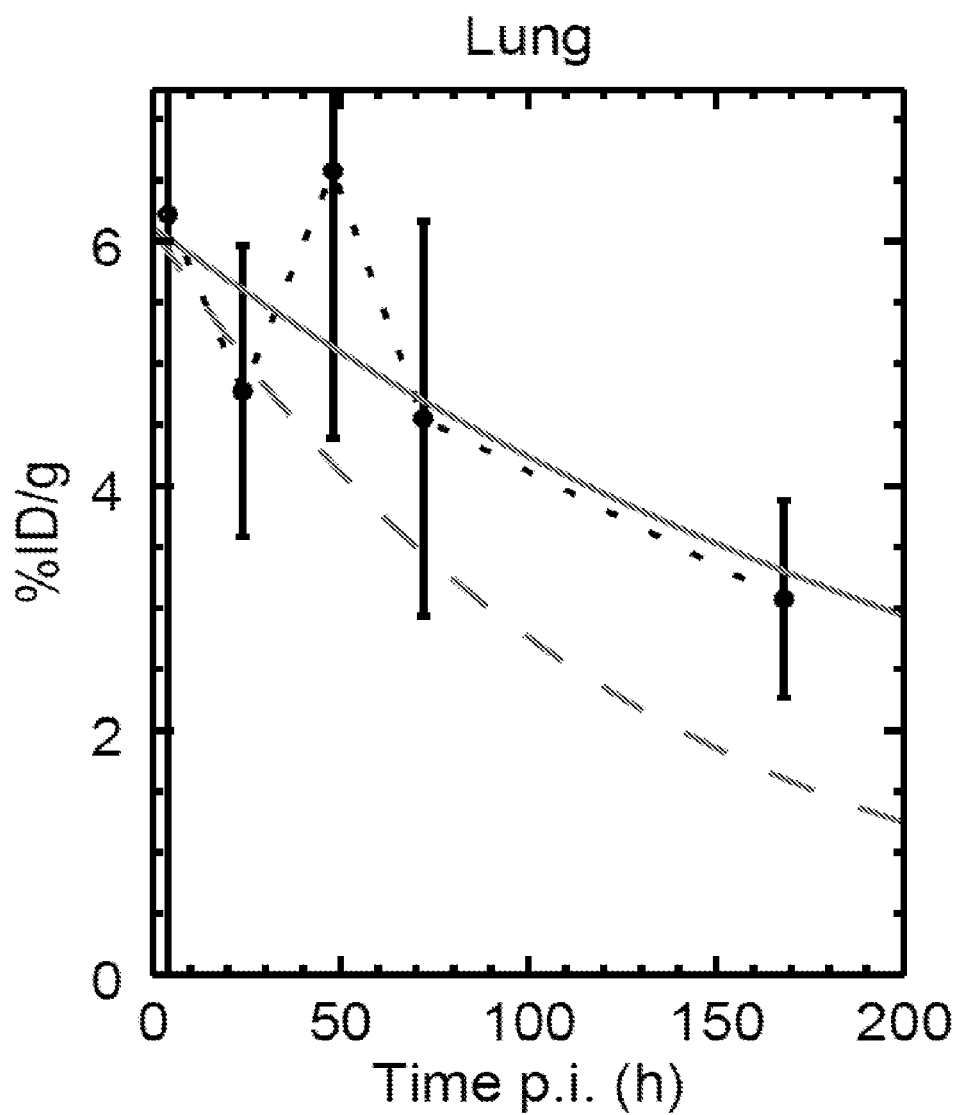
Figure 21:
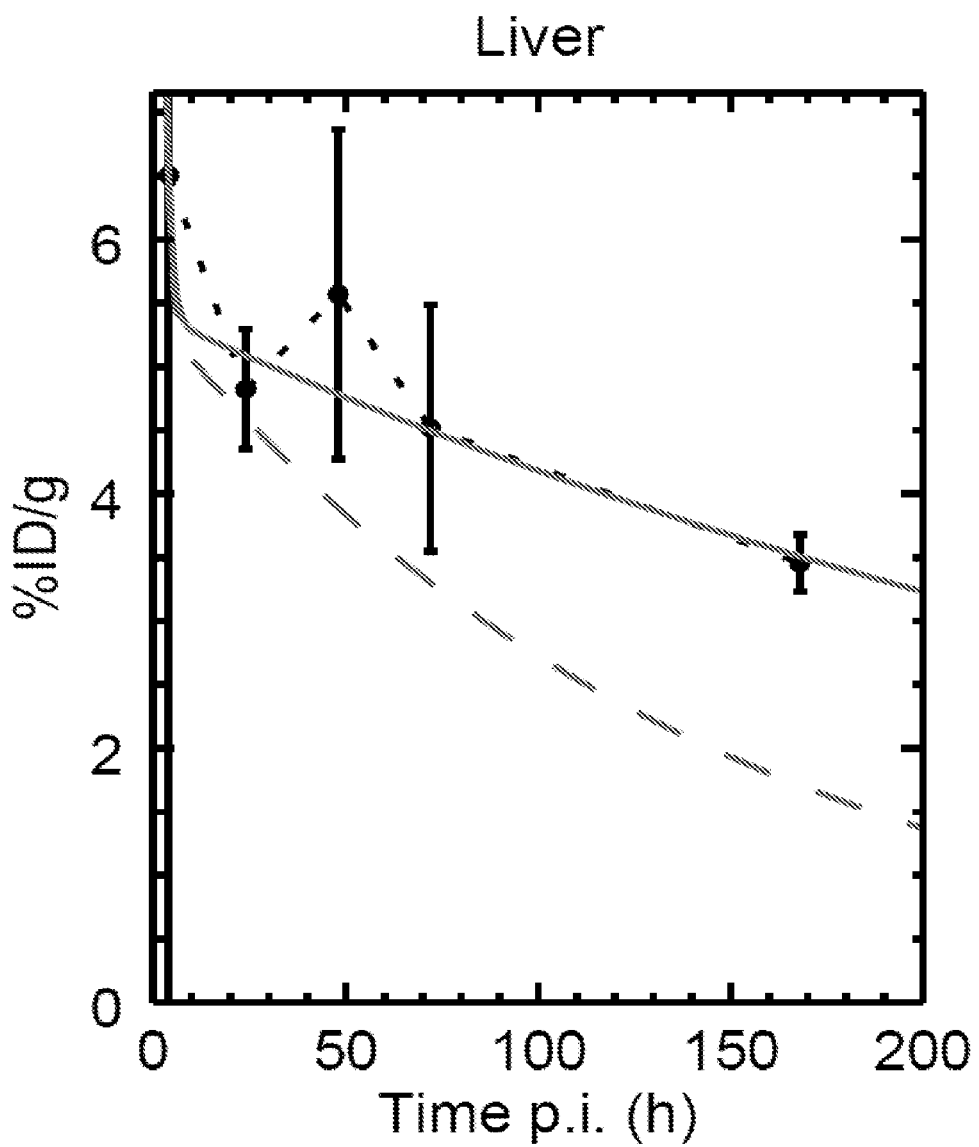
Figure 21:
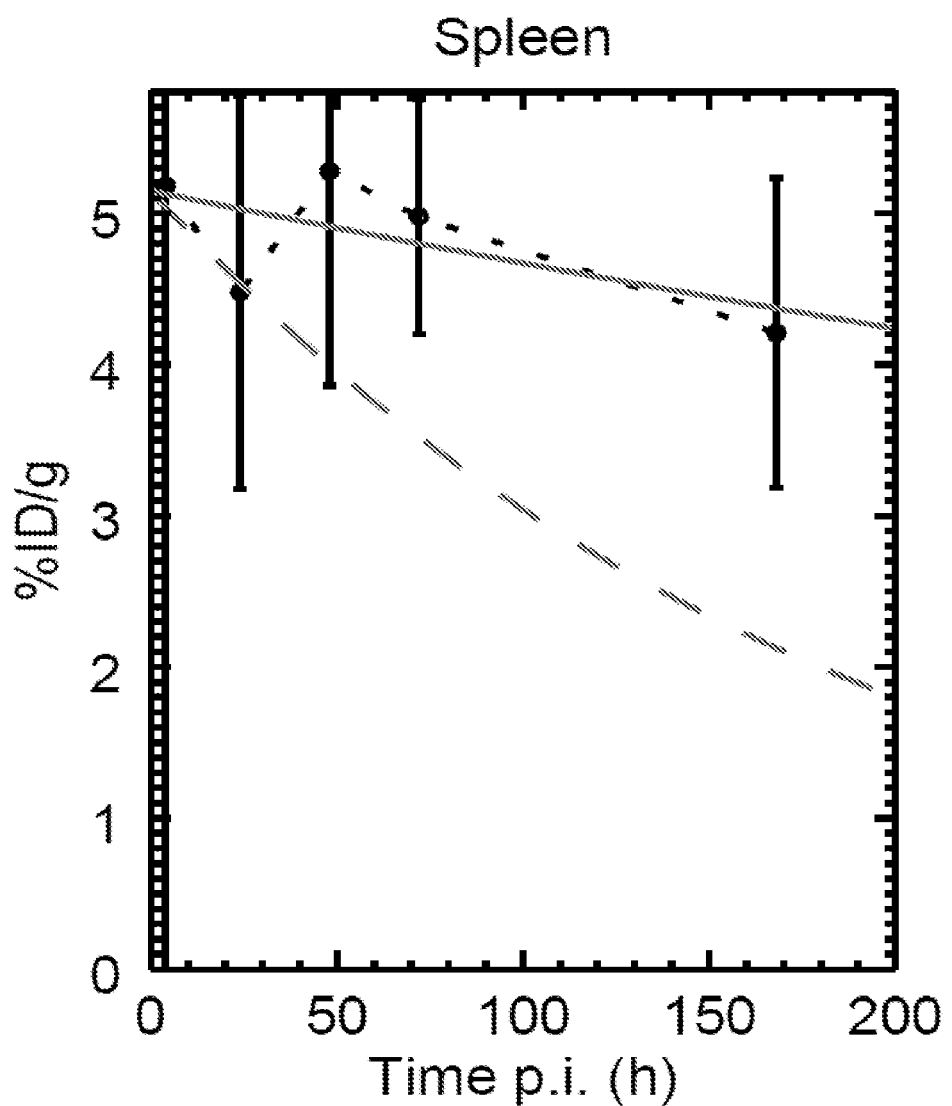
Figure 21:
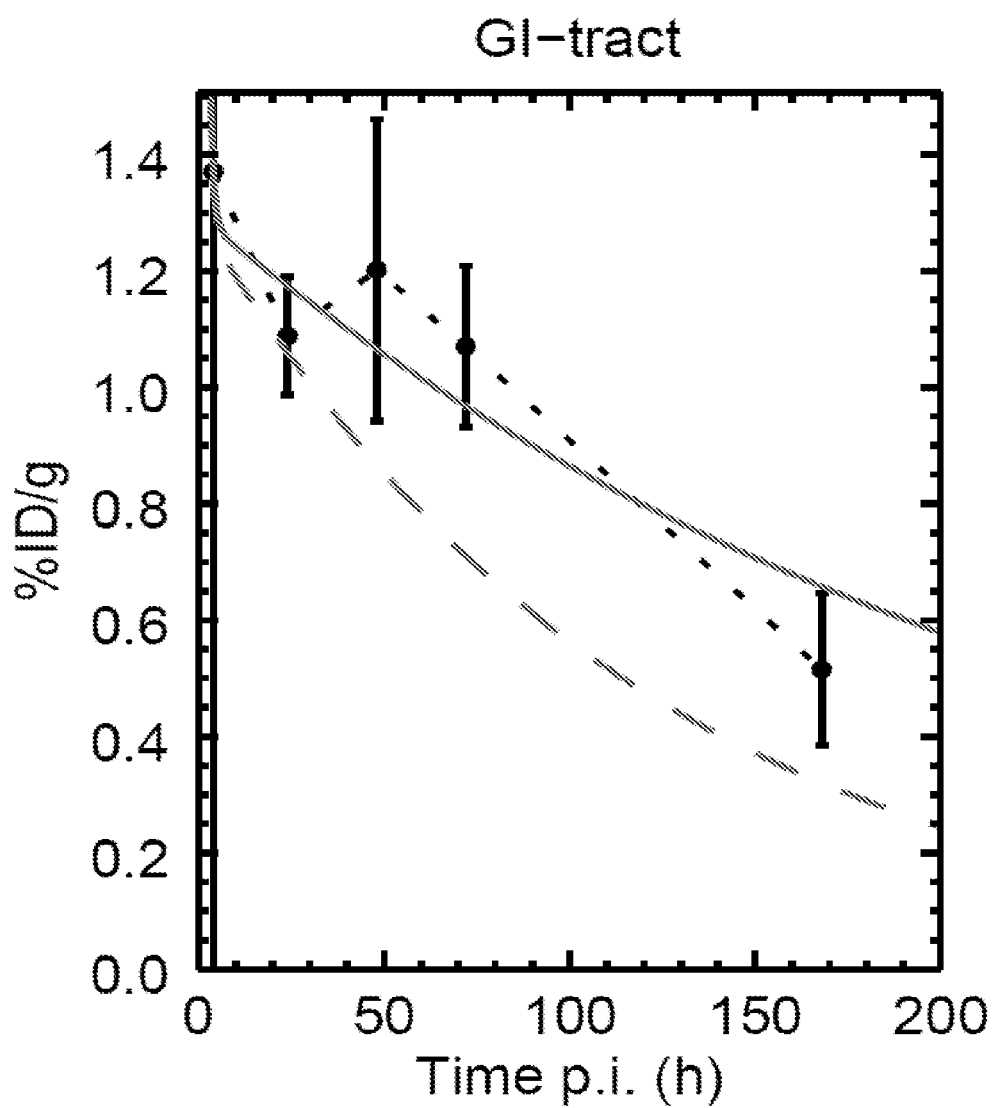
Figure 21:
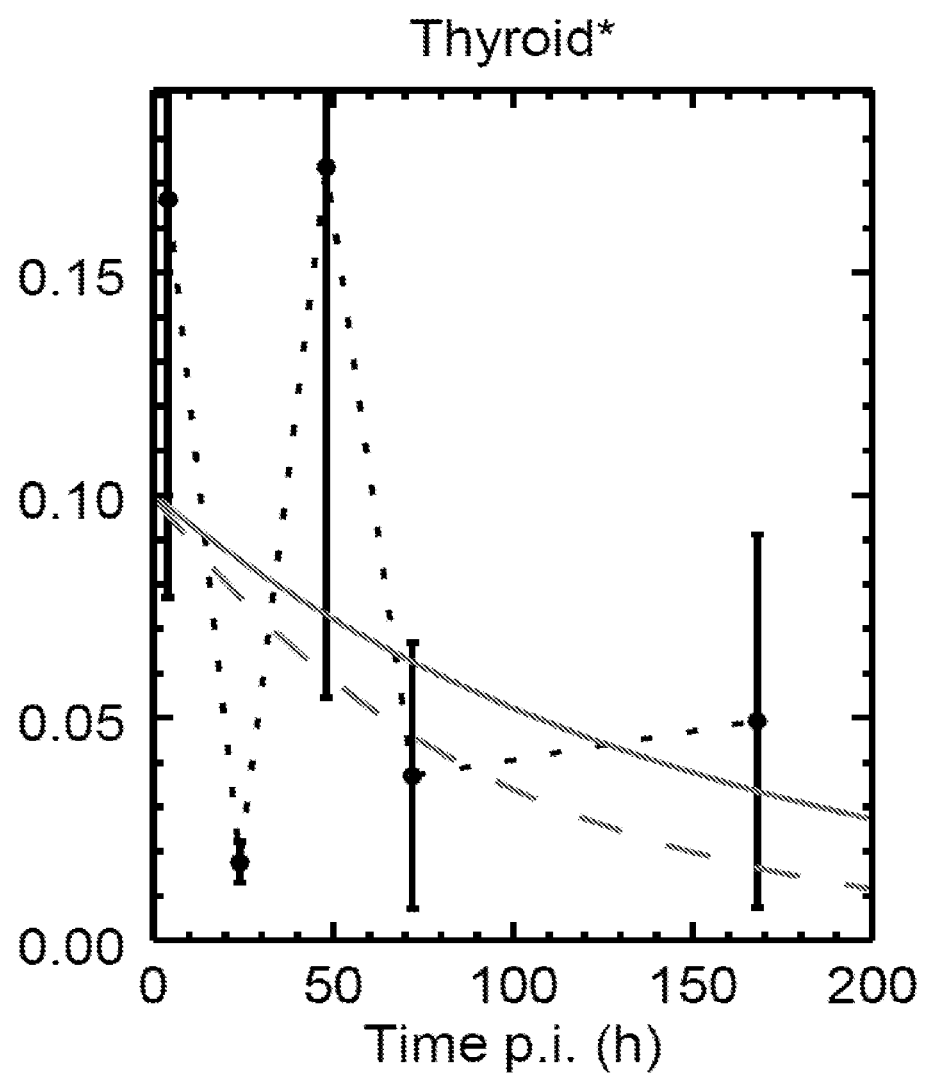
Figure 21:
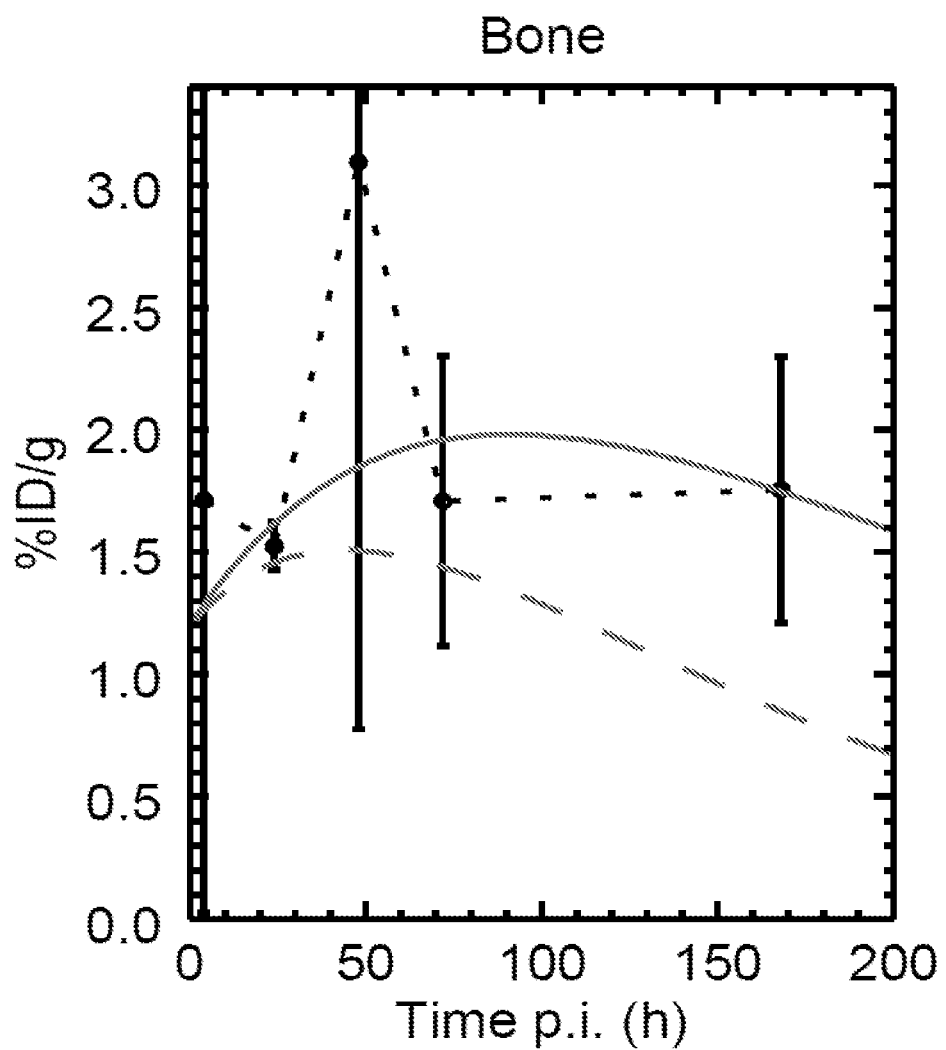
Figure 21:
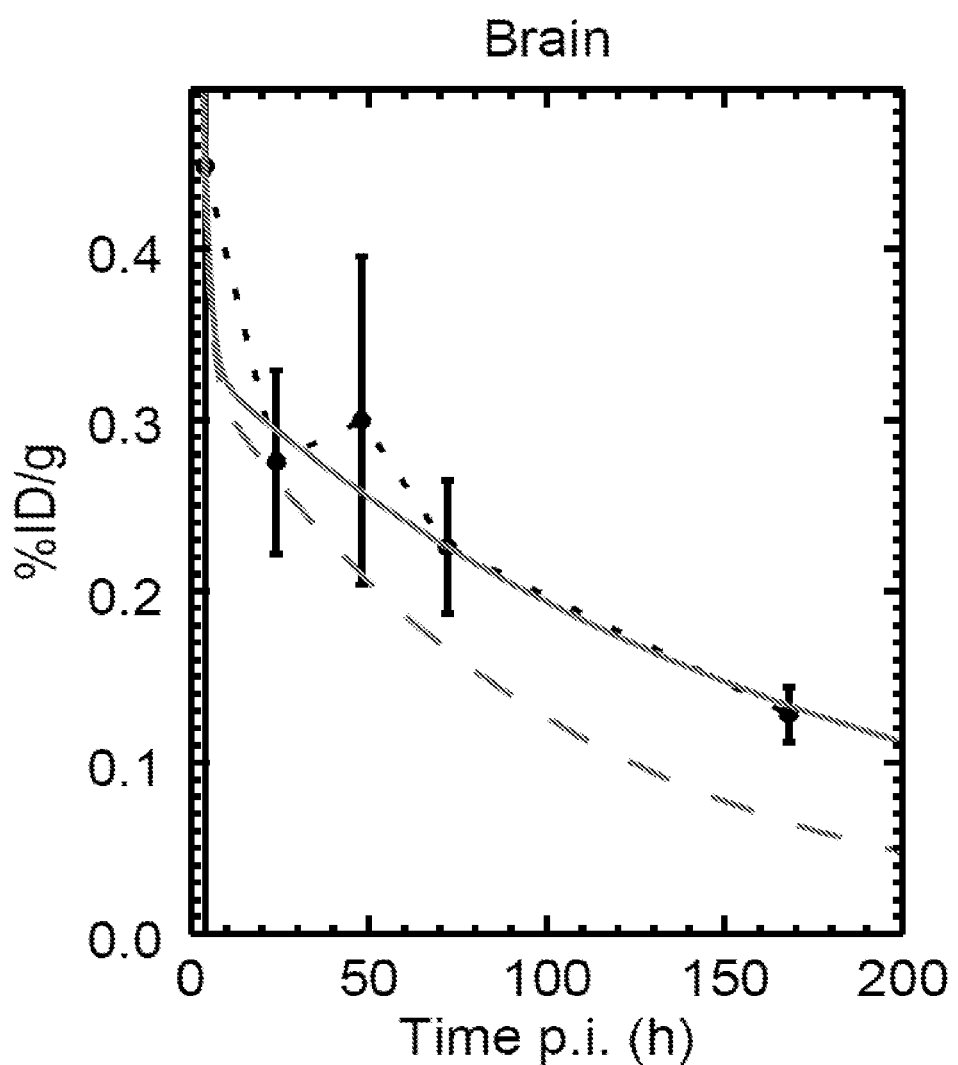
Figure 21:
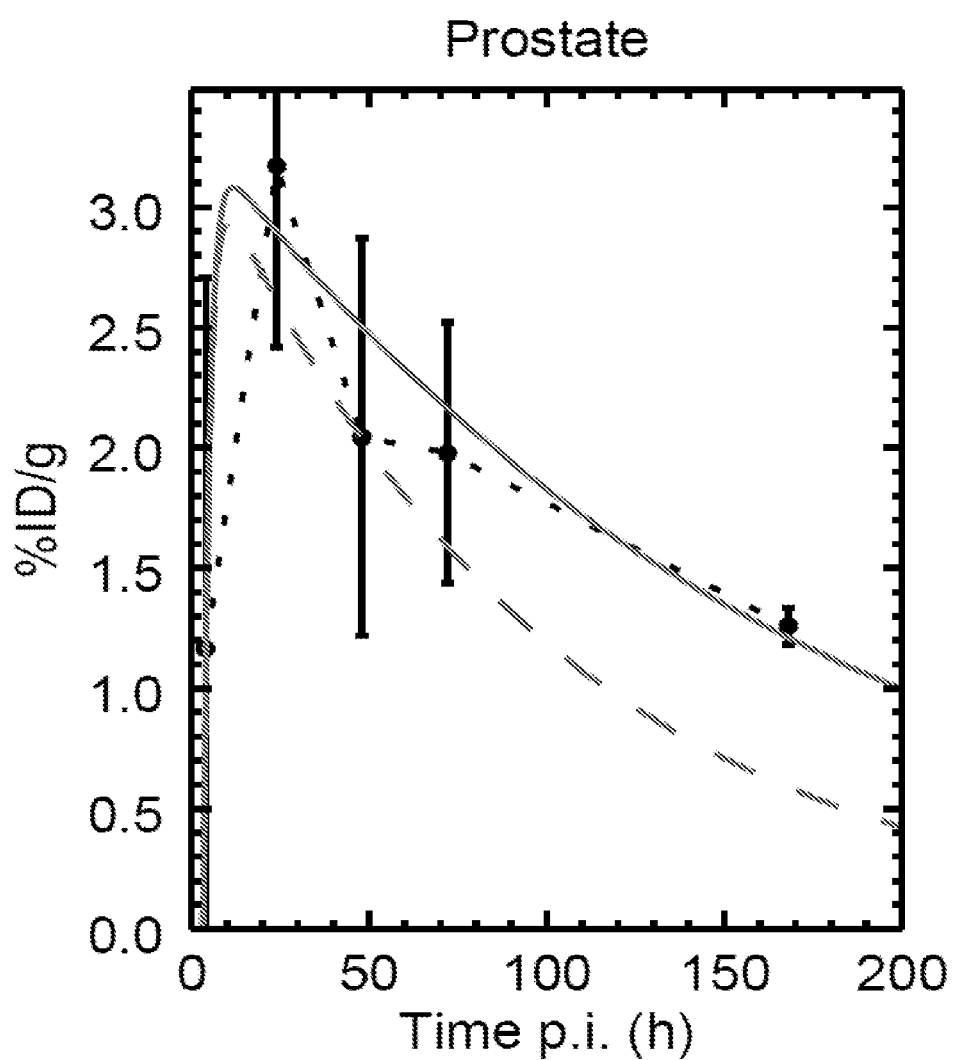
Figure 21:
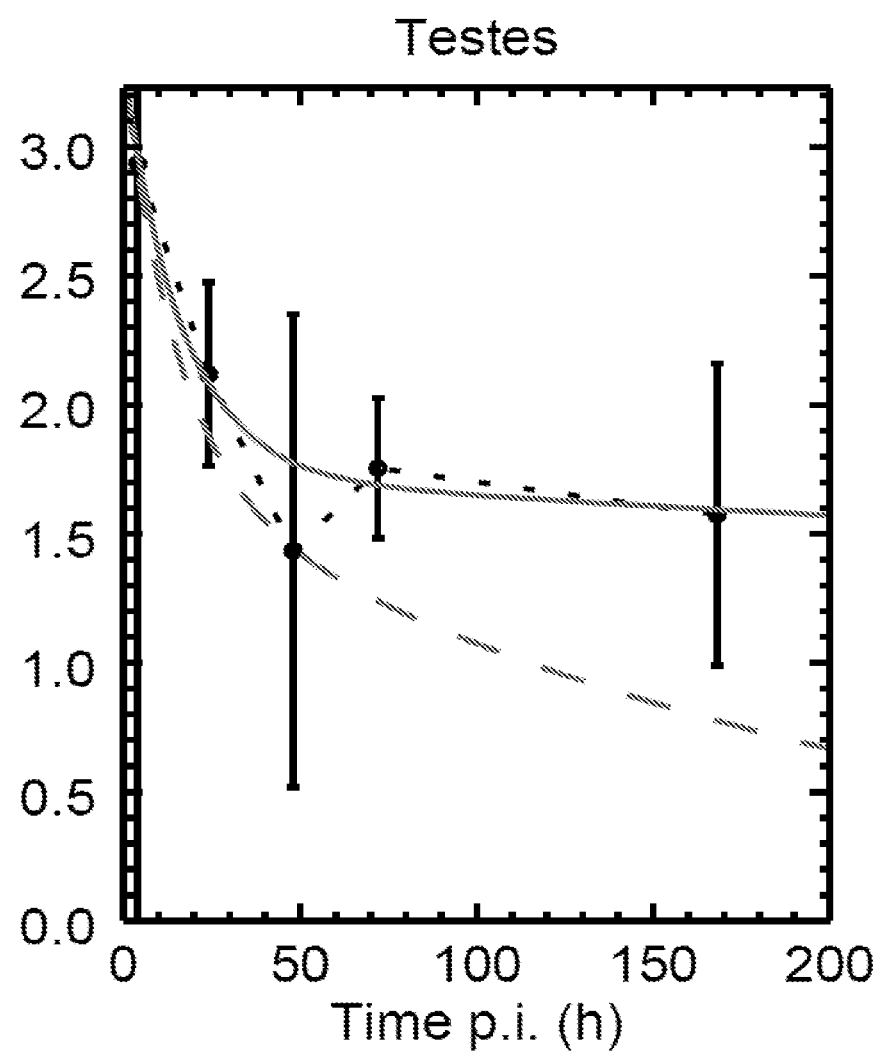
Figure 21:
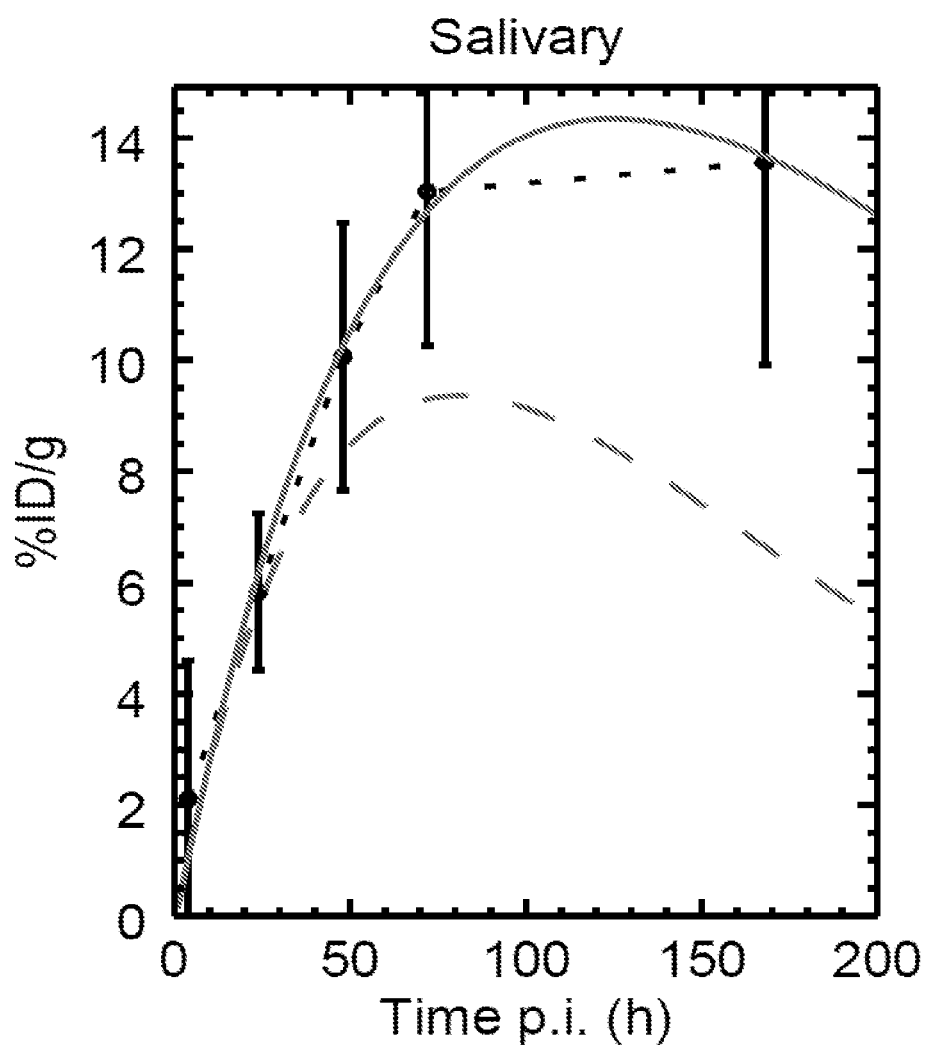
Figure 21:
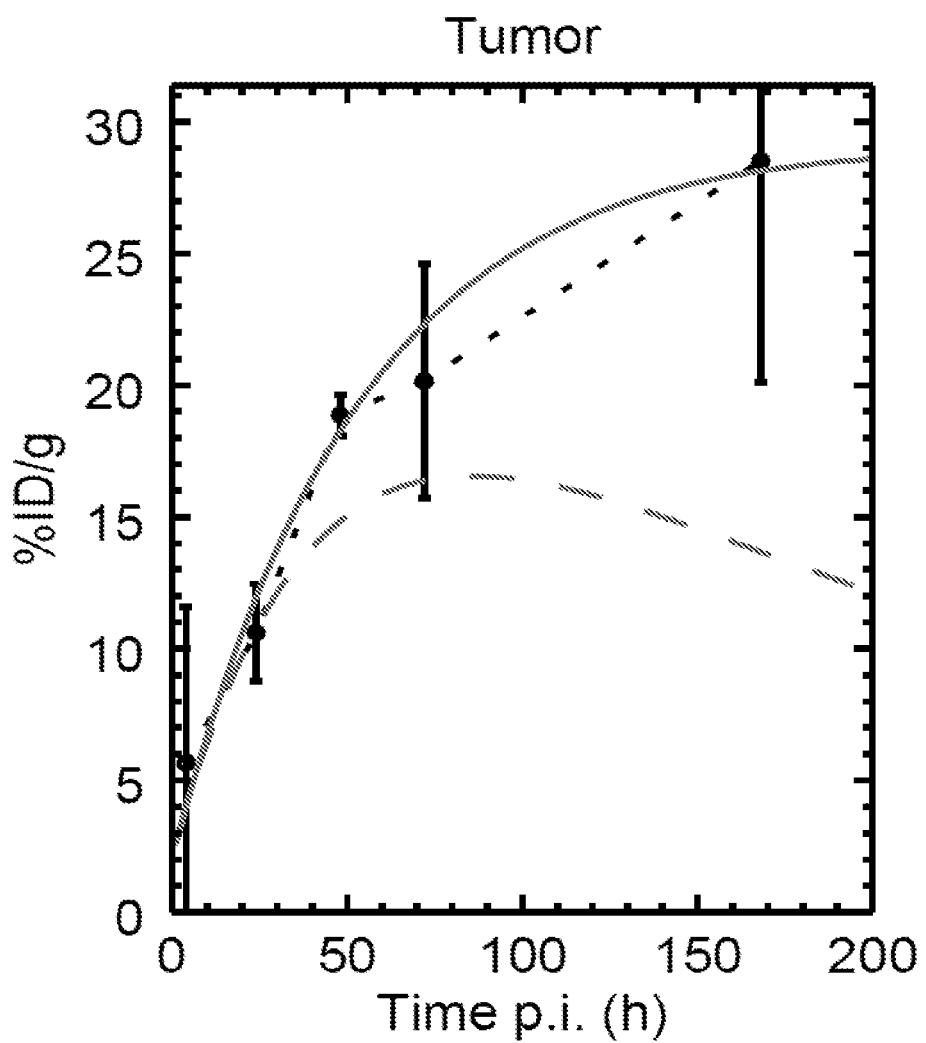
Figure 21:
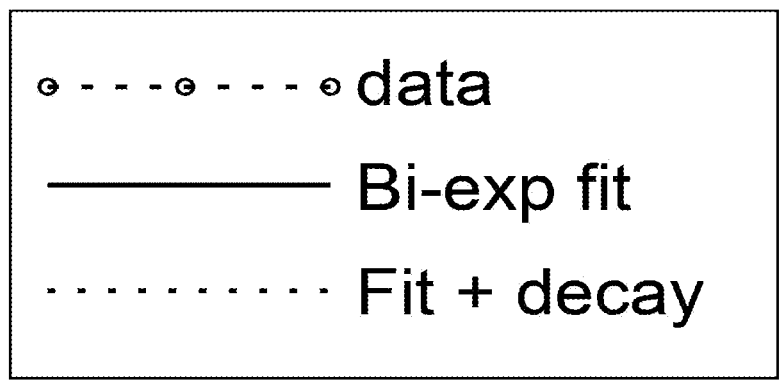

FIG. 20 shows the detailed biodistribution at 72 h pi of $^{111}$Lu-11 B6 in LnCAP xenografts FIG. 21 shows the in vivo biokinetics of $^{177}$Lu-11B6 in LnCAP xenografts.

Figure 22:

FIG. 22 shows representative photographs of tumour size before (left image) and after (right image) treatment with $^{177}$Lu-11B6.

Figure 23A:
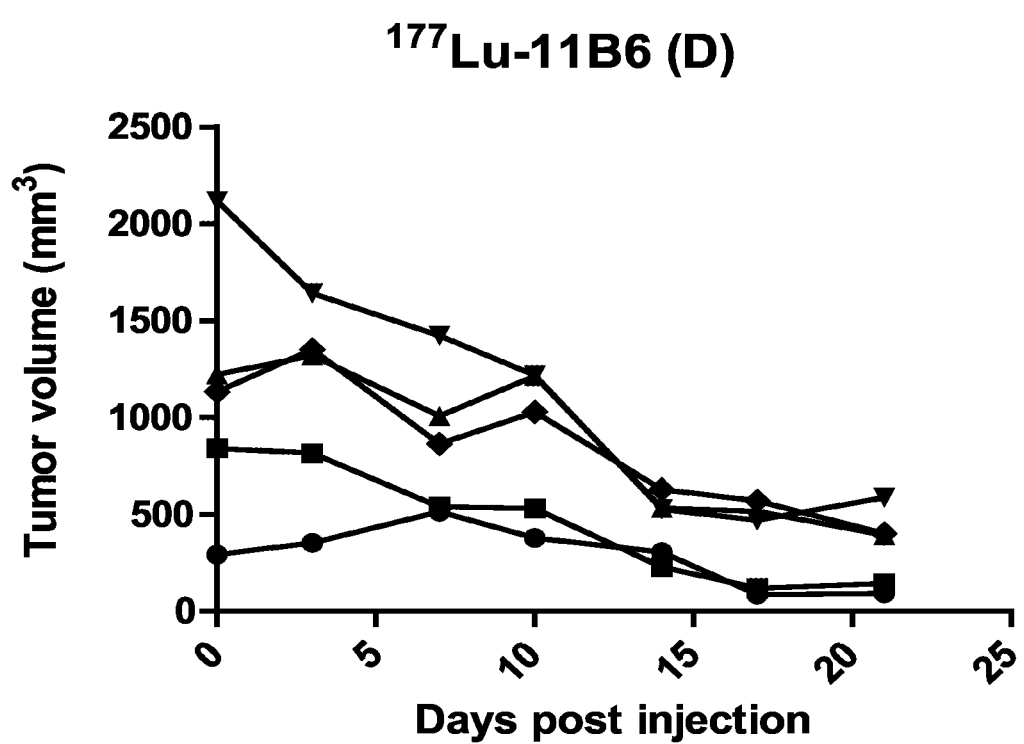
Figure 23B:
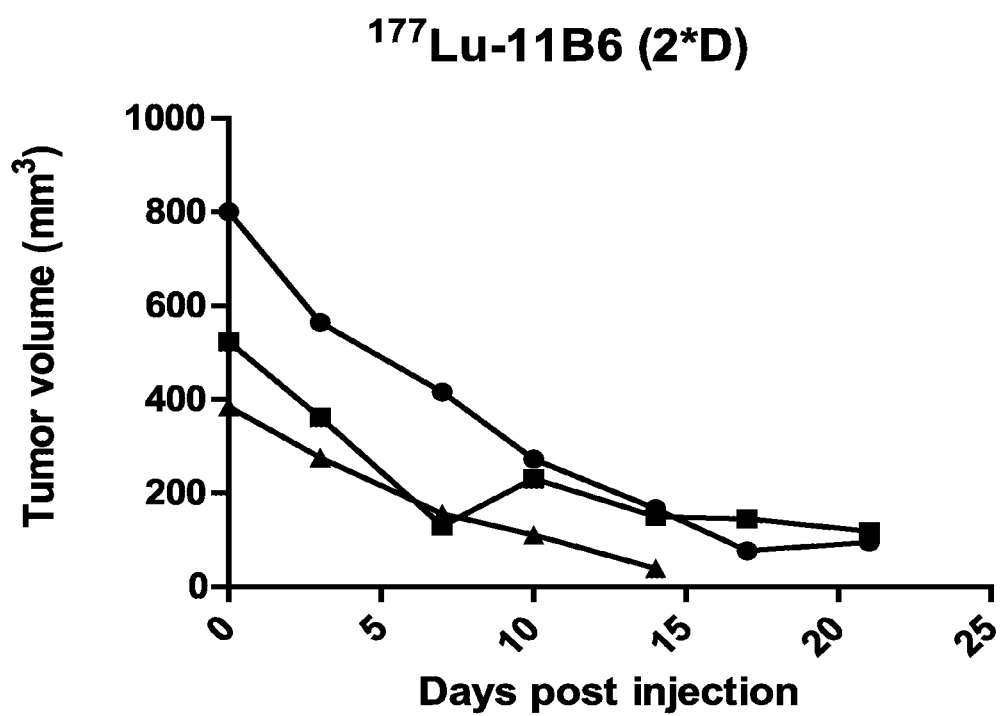
Figure 23C:
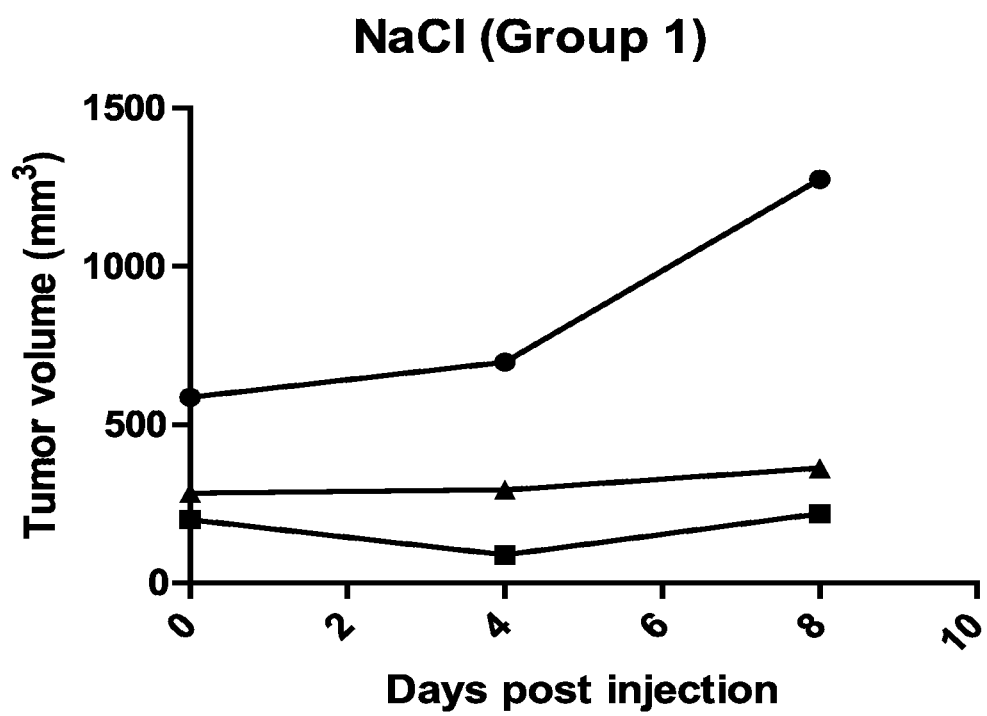

FIGS. 23A-23C show a summary of the effect of (FIG. 23A) single dose $^{177}$Lu-11B6, (FIG. 23B) double dose $^{177}$Lu-11B6 and (FIG. 23C) control treatment on tumour size in LnCAP xenografts.

Figure 24A:
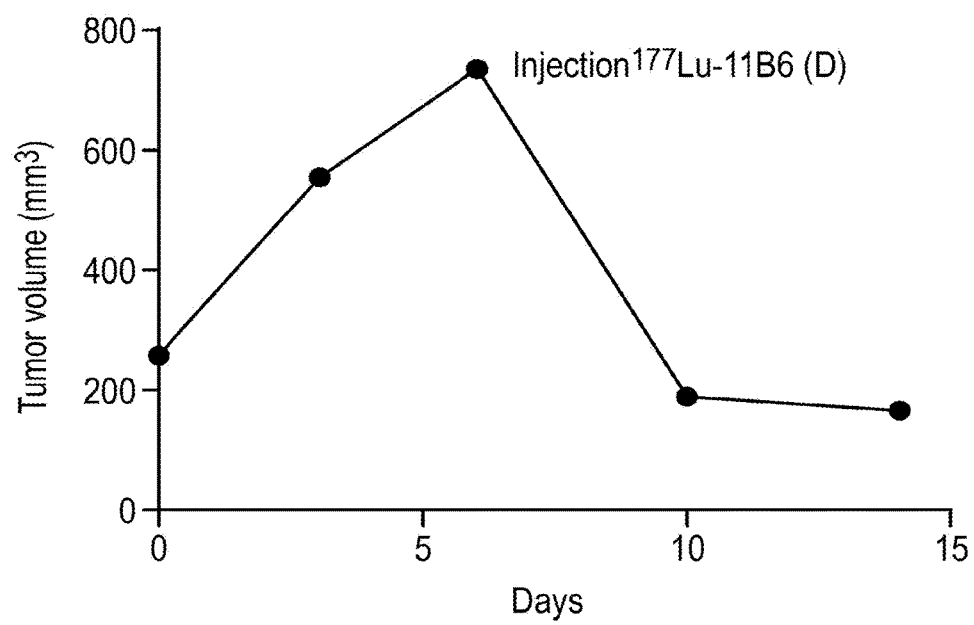
Figure 24B:
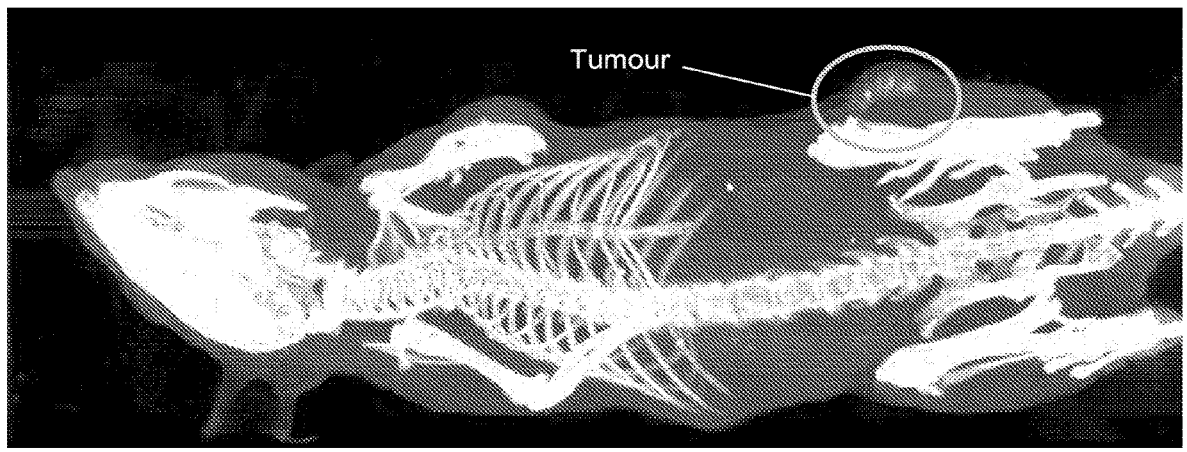

FIGS. 24A-24B shows (FIG. 24A) tumour growth data and (FIG. 24B) a SPECT image for one LnCAP xenografts mouse treated with a single dose $^{177}$Lu-11B6

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1—BIODISTRIBUTION OF $^{125}$I-PSA30 and $^{125}$I-11B6

Material and Method: The PSA30 and 11B6 antibody were labeled with $^{125}$I (PerkinElmer, USA), using the Iodogen method. Briefly, a coated test tube with 150 μg 1,3,4,6-tetrachloro-3α,6α-diphenyl glycoluril was used for labeling of 200 μg PSA30. After the mixture had been incubated for 15 min at room temperature, low molecular weight components were removed by gel filtration (PD-10 column, GE Healthcare, UK). The radiochemical purity was 95% after gel filtration.

Figure 1:
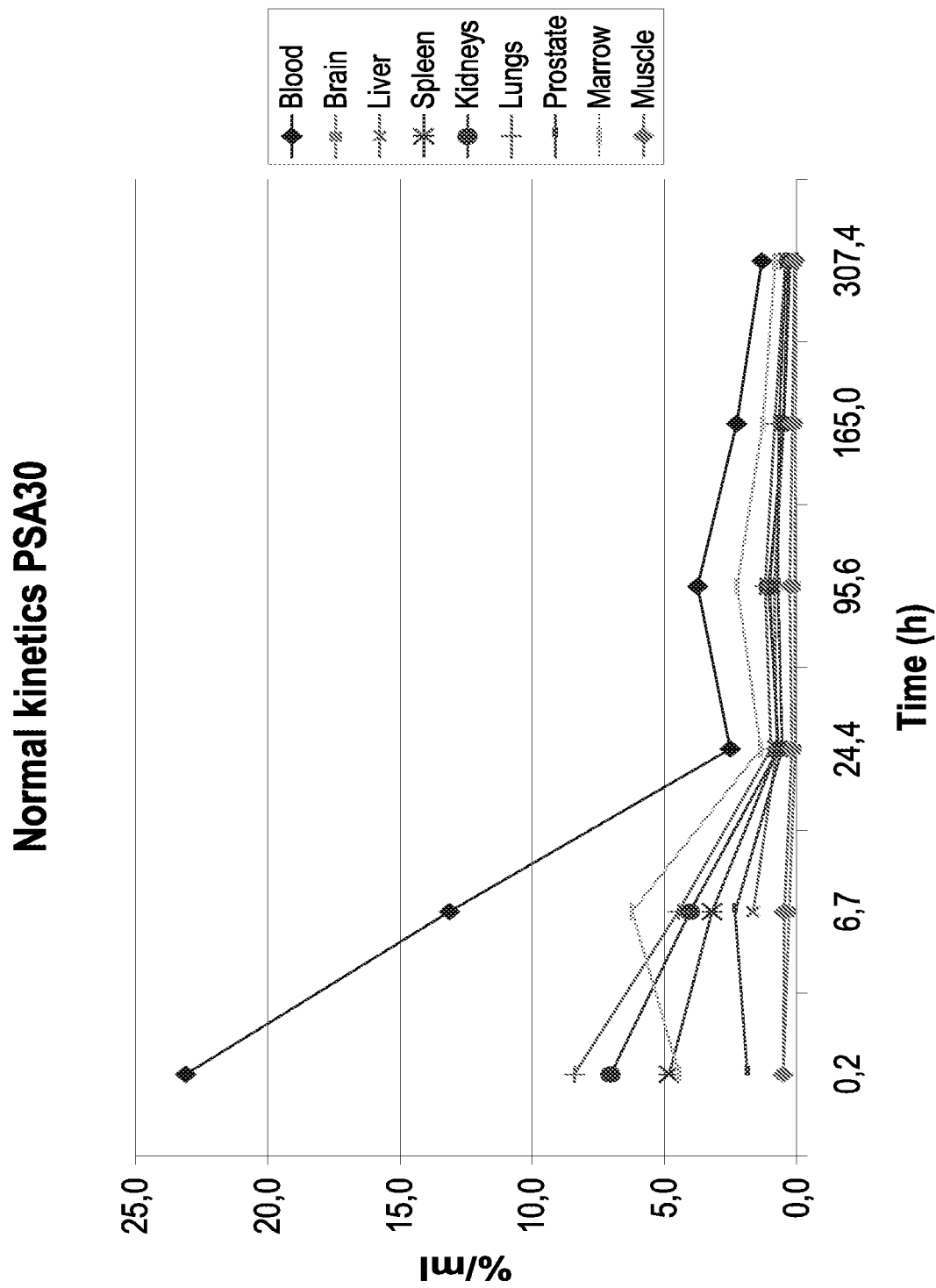
FIG. 1 shows the kinetics of $^{125}$I-labelled PSA30 antibody in various tissues following intravenous administration in normal mice.
Figure 2:
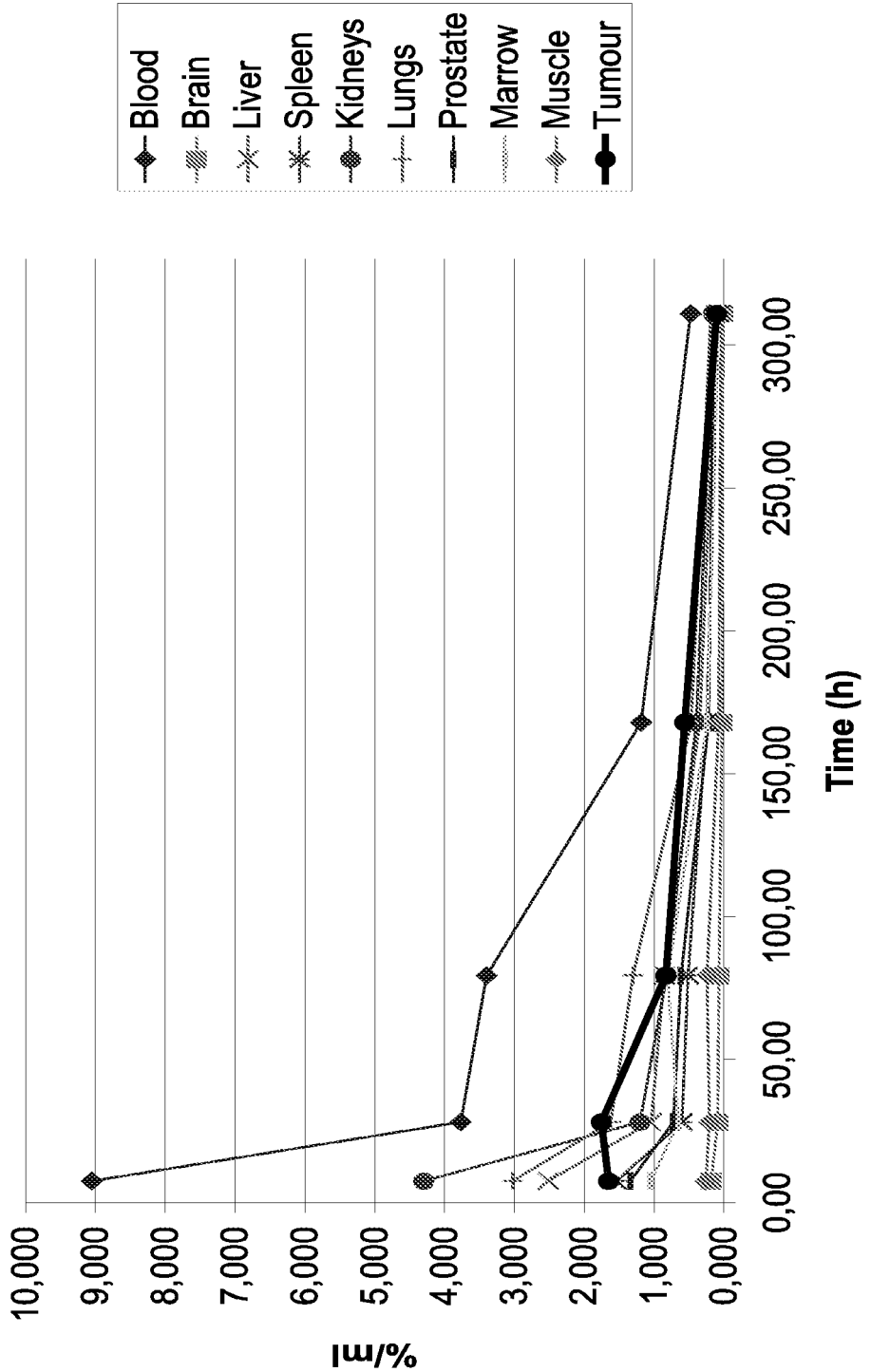
FIG. 2 shows the kinetics of $^{125}$I-labelled PSA30 antibody in various tissues following intravenous administration in mice implanted with xenograft of metastatic prostate tumour cells, and this shows that metastatic prostate tumour cells show a strong take up the PSA30 antibody.
Figures 4A, 4B:
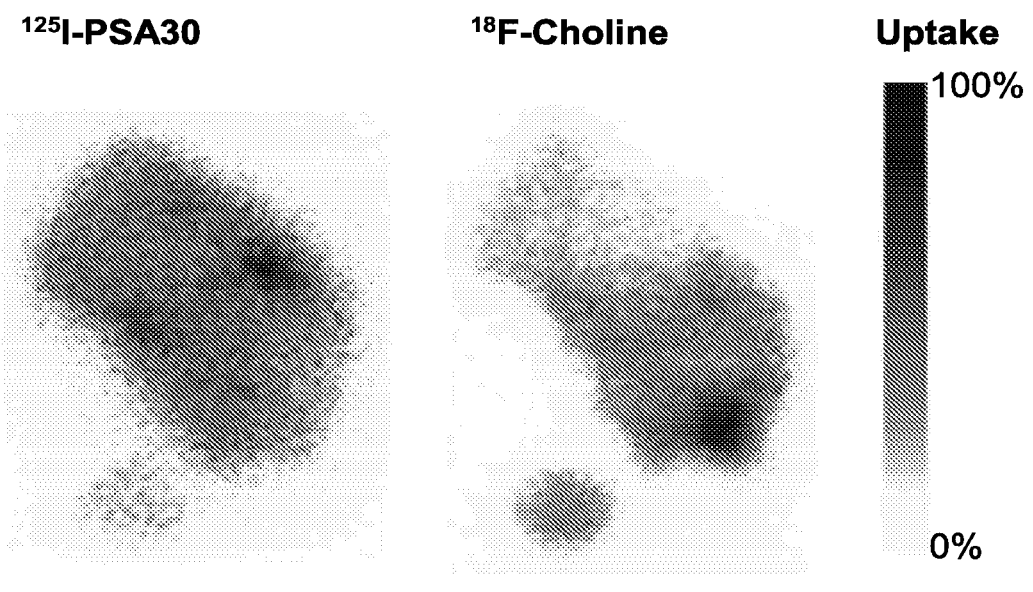
Figure 4C:
Figure 4D:
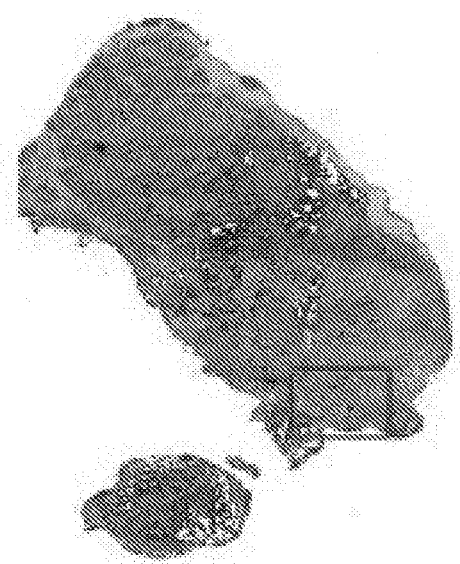
Figure 4E:
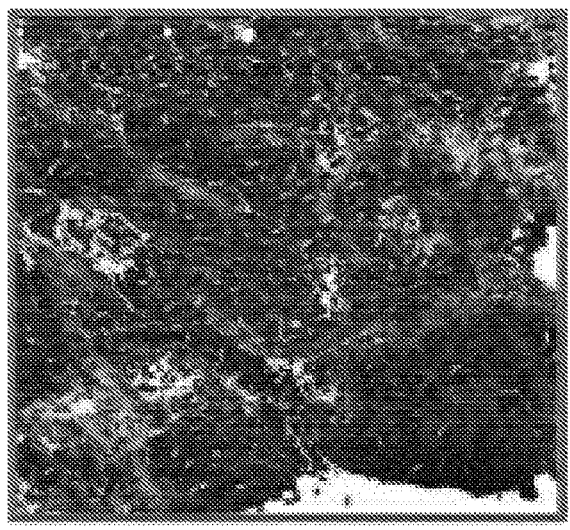
Figure 4F:
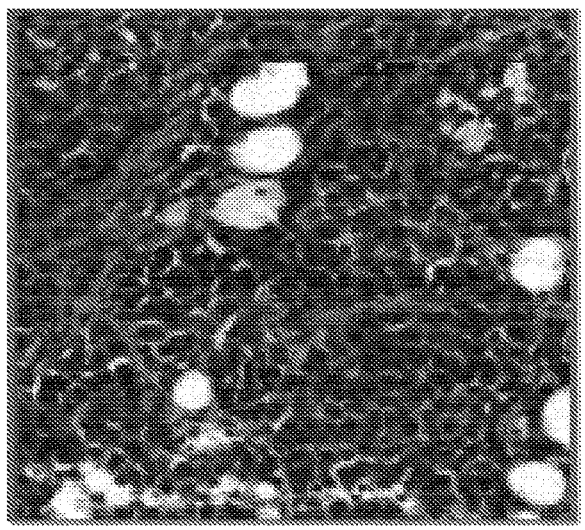
Figure 4G:
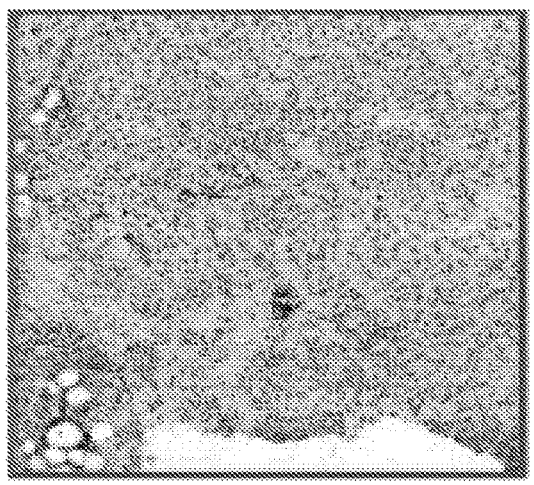
Figure 4H:
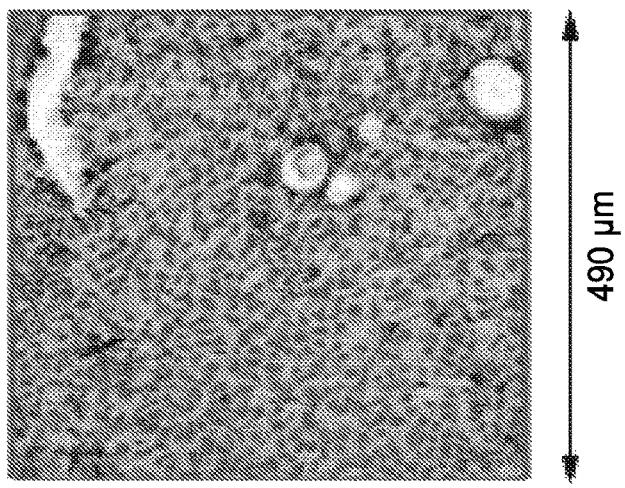

Results and discussion: See FIGS. 2 and 3. LNCaP tumors had higher uptake compared to other investigated organs at most time-points and peaked (4.32% IA/g) at 24 h after intravenous injection of $^{126}$I-PSA30 formulations. By contrast to all other organs showing a decrease of activity, LNCaP tumors showed a marked increase of activity (by 32%) during the first 24 hours after injection In comparison to non-tumor bearing mice, thyroid accumulation was greatly augmented. $^{126}$I-PSA30 mAb uptake in LNCaP tumors peaks at 24 h post injection, with a subsequent sharp decrease in tumor uptake noted by 72 h post injection. Importantly, at this same time point, there is a sharp increase in thyroid uptake. This inverse correlation is a likely indicator that a dehalogenation effect has occurred. In conclusion, $^{126}$I-PSA30 can effectively target fPSA in LNCaP-based xenograft mice.

EXAMPLE 2—BIODISTRIBUTION OF $^{111}$In-DTPA-11B6

Material and Method: The animal experiments were performed in accordance with national legislation on laboratory animals' protection. The animal study has been approved by the local Ethics Committee for Animal Research. Male immunodeficient nude mice (6-8 wk old) purchased from Taconic Europe (Bomholt, Denmark) were used for this study. Xenografts of hK2-expressing LnCAP prostate carcinoma cells were subcutaneously implanted in the right flank. For xenografting, LNCaP cells, 5.2×10$^6$ cells/mouse in 100 μL cell medium and 100 μL Matrigel (BD Sciences, Bedford, USA). DU145 cells (a hK2-negative cell line), 1-2×10$^6$, were sc implanted in the right flank to serve as a negative control. Three-six weeks post injection of LNCaP cells, 5 groups of mice (4-5 animals/group) carrying LNCaP xenografts and 1 group (3 animals/group) carrying DU145 xenografts were each iv. injected with 100 μl $^{111}$In-DTPA-11B6 (-200 kBq in 100 μl and 22.5 μg protein). Animals were sacked at a different time point, 4 h, 24 h, 48 h, 72 h or 168 h p.i. and the control group at 48 h p.i. Organs of interest (see table) were placed in 20 ml vials for scintillation counting (Zinsser Analytic, Frankfurt, Germany) weighed and measured in an Automated gamma-counter with 3-inch NaI(TI) detector (1480 Wizard OY, Wallac, Turku, Finland). All organs were measured twice after dissection and after the last time point. Measurement of radioactivity was performed as a standard protocol below.

Measurement of Radioactivity: A standard protocol for measurement of a radionuclide was used. Counts per minute corrected with background level were used for the evaluation. The tissue uptake value, expressed as percent injected dose per gram tissue (% ID/g), was calculated as:

% ID/g=(tissue radioactivity/injected radioactivity)/organ weight×100 wherein for iv injections:

Injected radioactivity=Average radioactivity in control syringes−radioactivity in used syringe−radioactivity in tail Results and discussion: See FIGS. 8, 12 and 13. Preliminary results showed that $^{111}$In-11B6 was effectively accumulation in the tumor over time, peaking at 48 hpi with 16.4±1.92% IA/g (percent injected activity per gram). Radioactivity uptake in normal organs (liver, spleen, kidneys, bone, prostate, testes) are at a lower level. Somewhat elevated uptake was observed in the salivary glands, likely due to a certain normal expression of hK2 expression (FIG. 8). This will be further investigated in future studies. Further, the $^{111}$In-DTPA-11B6 was hK2-specific since it was significantly lower uptake in the negative control xenografts DU145 (FIG. 13). The tumor/blood ratio was increasing over time, indicating that more and more of $^{111}$In-DTPA-11B6 taken up in the tumor (FIG. 12). In conclusion, the biodistribution data of $^{111}$In-11B6 shows promising tumor-targeting properties in prostate cancer, indicating potential for therapy of prostate carcinoma using other radionuclides.

EXAMPLE 3—DIGITAL AUTORADIOGRAPHY IMAGING

Materials and methods: DAR was performed on animals injected with $^{125}$I-PSA and $^{18}$F-choline. Animals were euthanized one hour post injection of metabolic probes and tumors were immediately removed, secured in Cryomount (HistoLab products AB, Sweden), quickly frozen in liquid nitrogen and cut into 100 μm sections for DAR or 20 μm sections for histopathology and immunohistochemistry (IHC) analysis. A silicon strip detector based system, (Biomolex 700 Imager; Bimolex AS, Oslo) was used to image the distribution of radioactivity within the thicker sections. Differences in both emission spectra and rate of decay were used to produce separate images of each radionuclide in animals injected with more than one radionuclide, in this case, $^{125}$I and $^{18}$F.

Results and discussion: See results in FIGS. 4A-H. Based on these data, we demonstrate that the PSA30 mAb uptake in excised tumors peaked at 24 hours post intravenous injection, and is retained in tumor as compared to normal tissues. The relatively low T/O ratios (see Table in FIG. 3) can be attributed to factors; such as: a binding site barrier, seen when a low antibody dose is saturated by the fPSA antigens in the perivascular space thus preventing deeper penetration into the solid tumor; insufficient vascular permeability inside of the tumor; or deiodination of the antibody (as suggested by the high iodine accumulation in the thyroid). Two ways to improve the T/O ratios would be to increase the antibody dose and test different radiolabels. Despite this drawback, we found an accumulation of $^{125}$I-PSA30 activity in tumor tissue.

Immunohistochemistry and histopathology (see results in FIGS. 4A-H). To study PSA, 20 μm tumor cryosections (frozen and secured as described above) were examined using IHC. The immunoreactivity against PSA or hK2 was visualized by use of the DAKO EnVision Flex/HRP system kit (Dako Corporation). Adjacent tumor sections were also stained with hematoxylin (nuclei stain) and eosin (cytoplasmic stain) (H&E) and the general morphology analyzed under a standard transillumination microscope. With H&E staining, viable regions of the tumor sections and necrotic areas were stained. As a positive control, LNCaP tumor sections were incubated with PSA mAb 2E9 at a dilution of 1:1000 and visualized as described above. As a negative control, tumor section from a mouse that received an intravenous injection of PSA30 was visualized without incubation of a secondary antibody, but including all other steps of IHC. The stained sections were scanned using a Carl Zeiss MIRAX Scan microscope scanner and viewed with the MIRAX Viewer software (Carl Zeiss Imaging Solutions GmbH, Germany).

EXAMPLE 4—RADIOLABELING

Direct iodination ($^{251}$I/$^{124}$I/$^{131}$I/): Proteins (10 μl, 1 mg/ml in PBS) were mixed with $^{125}$I as NaI solution (4 MBq) using the Chloramine-T (CAT, Sigma St. Louis, MO, USA) method. The reaction was initiated by adding CAT in PBS (10 μl, 2 mg/ml) and incubated for 1 min during vigorous shaking and then terminated by adding sodium metabisulfite (20 μl, 2 mg/ml). Labeled proteins were separated from non-reacted $^{125}$I and low-molecular-weight reaction components by size-exclusion chromatography on a NAP-5 column (Sephadex G-25, GE Healthcare) pre-equilibrated with PBS.

Indirect iodination ($^{125}$I/$^{124}$I/$^{131}$I/$^{211}$At): Labeling precursor, N-succinimidyl p-(trimethylstannyl)benzoate (SPMB), was prepared according to Orlova et al in Nucl Med Biol 27:827-835 (2000), and 5 μg of SPMB was added to 5 MBq of $^{125}$I or $^{211}$At in a 5% solution of acetic acid. To start the reaction, 40 μg of chloramine-T (Sigma, St. Louis, Mo.) in aqueous solution was added. The reaction mixture was agitated for 5 min, and 80 μg of sodium-meta-bisulphate (Aldrich, Steinheim, Germany) in aqueous solution was added to stop the reaction. The radiolabeled precursor was added to 40 μg of protein solution in 0.07 M borate buffer, pH 9.2. The coupling reaction was performed at room temperature for 45 min with continuous shaking. Labeled protein variants were separated from low molecular weight products using a NAP™-5 size exclusion column (GE, Healthcare) equilibrated with PBS. The radiolabeled protein variants were then analyzed an IRMA test (according to Evans et al, submitted to CBR) to verify that the labeling procedure had not affected the binding affinity towards its target.

Radiolabeling with $^{177}$Lu: Conjugation of isothiocyanate-benzyl-CHX-A"-DTPA (130 nM) to protein (60 nM) was performed in 220 uL 0.7 M borate buffer pH 9.2 overnight in a 37° C. water bath. The conjugated CHX-protein was purified on a NAP-5 size exclusion column (GE Healthcare, Uppsala, Sweden), using 0.2 M sodium acetate buffer pH 5.5 as eluent, and then split into ten batches which were later used for chelation. Chelation time was optimised by sampling an ongoing chelation process and checking the purity of the chelate on instant thin-layer chromatography (ITLC) SG plates (Biodex) with 0.2 M citrate running buffer. The plates were analysed on a Cyclone Phosphorimager (Perkin Elmer, Wellesley, MA, USA). Chelation was found to be complete after 30 min at room temperature. The amount of radioactive lutetium was varied depending on the needs of individual experiments.

To test for presence of weakly chelated $^{177}$Lu, EDTA challenges were performed. Triplicate samples of the chelated product were challenged with 200:1 or 1,000:1 molar excess of EDTA versus chelator in a 37° C. overnight incubation. The EDTA concentration was calculated on the assumption that the conjugation was quantitative, thus yielding a mean value of two CHX-A-DTPA molecules per antibody. Samples of the solutions were then analysed by ITLC as above. As a control, triplicate samples of [$^{111}$Lu]-protein were also kept in PBS at 37° C. or 4° C. overnight.

EXAMPLE 5—IN VIVO STABILITY

To analyse the in vivo stability of the radiolabeled conjugates, normal mice are i.v. injected with radiolabels and euthanized after different timepoints. Blood is then collected, centrifuged at 5,000 g. Samples of blood are then separated on NAP-5 columns (cutoff, 5 kDa) equilibrated with PBS, and the relative amount of radioactivity present the high-molecular-fraction is determined.

EXAMPLE 6—CELL SURVIVAL FOR MONITORING THERAPY EFFECTS

Cells are seeded in Petri dishes (diameter 6 cm, approximately $2\times10^5$ cells/dish). After 48 hours, radiolabelled proteins (57 ng/dish, or 287 ng/dish, corresponding to approximately 1:1 and 5:1 antibodies per antigen) are added to the cells. In order to determine the effect of $^{125/131}$I/$^{177}$LU in the media, some of the dishes are preincubated with an excess amount of unlabeled protein (29 µg/dish). Extra dishes are used for estimation of number of decays per cell (DPC). In these dishes, the cellular uptake of radiolabelled protein is measured at six time points during the 24-hours incubation. The cells are then washed six times with cold serum-free medium, and the incubation is continued in fresh culture medium. Cells are counted approximately once a week, and are reseeded every 2 weeks. The DPC are estimated by calculating the area under the uptake curve for the two antibody concentrations, as well as for the blocked dishes. For the lowest radiolabelled protein concentration, the cells receive approximately 56 DPC, and for the highest approximately 150 DPC, whereas the blocked cells receive about 2 DPC. The results obtained are analyzed by nonlinear regression (exponential growth), using 1/Y2 as the weighting factor

EXAMPLE 7—IN VIVO STUDIES

The following xenograft models are used: LnCAP, DU145, PC-3 tumor models. PSA is expressed by all three cell lines while hK2 is expressed by LnCAP and not expressed in DU145 or PC-3.

For xenografting, LNCaP, DU145 or PC-3 cells (2-10 million cells), harvested in 0.02% trypsin/PBS were resuspended in media and injected sc into the right flank with 200 µL of cell suspension containing an equal amount of Matrigen (BD Biosciences, Bedford, MA). Tumor formation was monitored visually or by palpation.

Blocking Experiment: The blocking experiment in Biodistribution Experiment I was performed in order to establish whether uptake of radiolabelled proteins in tumors was hK2-specific or not. Before the major iv injection of radiolabelled protein, 0.8-3.0 mg of unlabeled protein was iv injected in the blocked mouse group. Uptake of radioactivity at 24-72 h post injection between the unblocked and blocked groups were compared.

Optimization of specific activity: This experiment is conducted to determine the influence of specific activity (i.e., the injected protein dose of the radiolabelled conjugate) on the tumor uptake. A series of $^{177}$Lu-labelled protein with various predetermined specific activities are prepared. An aliquot of $^{177}$Lu-labelled protein is diluted with a stock solution of unlabeled protein to provide injection doses varying from 10 µg to 500 µg per LnCAP-bearing mouse. Two-three days after injection, the animals are euthanized. Organs and tumors are excised and measured for radioactivity uptake. The specific activity providing the most optimal tumor uptake is further considered for dosimetry Example of dosimetry determination: LnCAP-bearing mice (4 mice/groups) are injected with $^{177}$Lu-labelled protein. The animals are euthanized 4 hpi-2 weeks post-injections. Absorbed dose to different organs is calculated using MIRD scheme. Time-activity curves will be obtained for all organs tissues of interest in the body (animal). The studies will be based on quantitative imaging from SPECT and/or PET. Integration of the curves will give cumulated activity. Using the MIRD formalism of based on own calculated (based on specific geometries and Monte Carlo techniques for absorbed fractions) S values will be used to convert cumulated activity to absorbed dose. In many cases the cross dose has to be carefully calculated meaning that Monte Carlo based dosimetry calculations will be done (Hindorf, et al. (2004) *J. Nuc. Med.*, 45:1960-1965; Larsson, et al. (2007) *Cancer Biotherapy & Radiopharmaceuticals*, 22:438-442; Larsson, et al. (2011) *Acta Oncol.*, 50:973-980).

Example of SPECT and PET imaging: PET-CT and SPECT-CT imaging is an integral part of radionuclide therapy. It gives an idea of the extent to which the radioactive material accumulates in the tissues and helps to provide an estimate of the required therapeutic dose and its effects. For good treatment results, a sufficient dose of radiation must be delivered to the tumor. This is confirmed by imaging, as discussed in the references mentioned above in respect of dose planning, the contents of which are incorporated herein by reference.

Radiobiology: The specific dosimetry methods based on individual patient/laboratory animal geometries will be used for a proper dosimetry and can be related to biological effects and give the possibility of correlation with radiobiological effects and for optimized therapy of individual patients.

EXAMPLE 8—DETERMINATION OF BINDING AFFINITY SCATCHARD'S METHOD

The binding affinity (Kd) of the produced antibody variants were determined to by using a Scatchard's method according to Scatchard, *Ann N Y Acad Sci* 51:660-72 (1949).

In brief, a fixed concentration of antibody (or, in this case, a Fab antibody fragment) and varying concentrations of $Eu^{3+}$-labelled PSA tracers were used.

Surface Plasmon Resonance

The binding kinetics and affinity of the antibody variants may also be determined by real-time biospecific interaction analysis on a Biacore instrument. In brief, PSA or hK2 is immobilized on a CM5 sensor chip by amine coupling and the immobilization levels reached 1000-2000 response units. The different anti-PSA or anti-hK2 antibody derivatives (both mAb and Fab) are diluted in concentrations ranging from 0.1-10 nM in HBS-EP buffer. The binding kinetics are studied in a 5 m in association phase and a 30 min dissociation phase with a flow rate of 50 µL/min, followed by regeneration. Kinetic constants are calculated using a 1:1 Langmuir binding model with correction for mass transfer.

EXAMPLE 9—IMMUNORADIOMETRIC ASSAYS (IRMA)

Monoclonal antibody-based immunoradiometric assays (IRMA) for radiolabelled mAb or Fab's binding quality were conducted in triplicate as a four-step sandwich assay with wash steps between incubations (washing buffer: 10 mM Tris-HCL pH 8.0, 0.15 M NaCl, 0.05% Tween 20). The assay was constructed and optimized according to established recommendations. Breakapart microtiter plates were coated with H117 (0.2 µg/well), a monoclonal antibody recognizing free or total PSA and human kallikrein 2 (hK2) with the same affinity, 30 diluted in coating buffer (75 mM sodium carbonate pH 9.6) and incubated overnight at 4° C. The wells were then incubated with 0.2 µg/well quenching buffer (3% fish gelatin in washing buffer) for two hours at room temperature. Next, the wells were coated with 200 µl plasma (female) containing 3 ng/µL fPSA and incubated for two hours at room temperature. Radiolabeled and unlabeled PSA30 were then mixed together in assay buffer (50 mM Tris-HCl pH 7.5, 0.1 M NaCl, 5 mM EDTA, 0.25% BSA and 0.05% Tween 20) at descending concentrations and added to the wells (total volume: 50 µL/well). The percentage of labeled antibody per well was as followed: 100, 92, 84, 68, 50, 30 and 0 percent. The plates were incubated for two hours at room temperature, washed and measured in a NaI(TI)-well counter (1282 Compugamma CS; LKB Wallac, Turku, Finland). A difference in detection capacity of <25% in relation to theoretical deviance was accepted for further application. The estimations of detection quality post labeling showed that radiolabeled antibody maintained 70-90% of the affinity/binding capacity of the unlabeled antibody.

EXAMPLE 10—RADIOIMMUNOTHERAPY WITH 177Lu-m11B6 IN A PROSTATE CANCER MOUSE MODEL

Prostate cancer is the most commonly diagnosed cancer among men in the Western world, accounting for 25% of all new cases of cancer and for 14% of deaths from cancer (22700443). Current curative treatment strategies (surgery and irradiation) are only successful when the malignancy is localized to the prostate gland. The therapeutic strategy in the case of disseminated disease is limited to castration, which often only suppresses growth for 12-18 months before becoming refractory, despite the hormone-deprived milieu (Scher H I et al, Cancer of the prostate. In: DeVita V T Jr, Hellman S, Rosenberg S A, eds. 7th ed. Philadelphia, PA: Lippincott Williams & Wilkins; 2005). Because of the lack of therapies that have been proven to have an effect beyond a transient response, novel molecularly targeted therapies are urgently needed. Because prostate cancer is radiosensitive, it presents an ideal target for radioimmunotherapy. Also, radioimmunotherapy typically delivers high levels of circulating antibodies to bone marrow and lymph nodes, sites to which the cancer typically spreads. Additionally, radioimmunotherapy employs a "cross-fire effect", which, depending on the emitted particle range of the chosen radioisotope, may kill surrounding antigen-negative bystander cells without direct binding of the antibody (16029058).

Human kallikrein 2 (hK2) is an androgen driven enzyme that is solely expressed, at very high concentrations, in healthy and malignant prostatic tissue. Since hK2 has been shown to cleave the zymogen form of Prostate Specific Antigen (PSA), it is believed that one of its physiological functions is to act as a regulator of that enzyme. Taken together, these biological features make hK2 an optimal target in a theragnostic system (therapy and diagnosis).

The aim of this study was to confirm the utility of 11B6, a mAb that specifically targets an epitope inside the catalytic cleft of hK2, as a vehicle to deliver highly toxic radionuclides specifically to the sites of prostate cancer growth. In this proof of concept study, we chose to label the mAb with 177Lu, a low energy beta particle that also employs gamma emission, enabling SPECT-imaging to be performed.

Materials & Methods
Materials $^{177}$Lu was purchased from Mallinkrodt Medical BV, Petten, Holland. The Cyclone™ Storage Phosphor System and the OptiQuant™ image analysis software (Perkin Elmer, Wellesley, MA, USA) was used to measure the radioactivity on the ITLC (instant thin layer chromatography) strips (Biodex, US) for determining labeling kinetics and radiochemical purity. All chemicals were obtained from Sigma Alchrich and the buffers were in-house prepared using analytical grade water if not otherwise noted. The mAb 11B6 is an antibody specific for the human kallikrein 2 with an affinity for this antigen of about 1.2 nM; see SEQ ID NOs: 4 and 5 above (obtained from the University of Turku, Finland). For the in vivo studies, the prostate carcinoma cell lines LNCaP expressing hK2 (ATCC, Manassas, VA, USA) were used. Cells were cultured in RPMI 1640 medium supplemented with 10% fetal bovine serum and PEST (penicillin 100 IU/ml and 100 µg/ml streptomycin). The cells were maintained at 37° C. in a humidified incubator with 5% $CO_2$ and were detached with trypsin-EDTA solution (0.25% trypsin, 0.02% EDTA in buffer, Thermo Scientific).

Conjugation and Radiolabeling

Conjugation of CHX-A"-DTPA with 11B6: A solution of the mAb 11B6 in PBS was adjusted to pH 9.2 using 0.07 M sodium borate buffer. The sample was concentrated on an Amicon Ultra-2 centrifugal filter (2 ml, 100 K). The protein solution was conjugated with the chelator CHX-A"-DTPA (Macrocyclics, USA) in a molar ratio of 3:1 chelator to antibody at 40° C. The reaction was terminated after 4 h and CHX-A"-DTPA-11B6, from now on called DTPA-11B6, was separated from free chelate by size-exclusion chromatography on a NAP-5 column (GE Healthcare) equilibrated with 20 ml 0.2 M ammonium acetate buffer, pH 5.5. Conjugated 11B6 and 5A10 was eluted with 1 ml ammonium acetate buffer.

Radiolabeling of DTPA-11B6: DTPA-11B6 in ammonium acetate buffer pH 5.5 was mixed with a predetermined amount of $^{177}$LuCl$_3$. After incubation at room temperature for 2 h, the labeling was terminated and purified on a NAP-5 column, equilibrated with PBS. Labeling efficiency and labeling kinetics were monitored with ITLC strips, eluted with 0.2 M citric acid. In this system, the radiolabelled conjugate remains at the origin line, while free Lu-177 migrates with the front of the solvent. The radioactivity distribution was determined with a PhosphorImager system (Perkin Elmer, Wellesley, MA, USA) using the Optiquant as quantification software (Perkin Elmer, Wellesley, MA, USA).

Surface Plasmon Resonance

The protein hk2 (Department of Biotechnology, Turku, Finland) in 10 mM NaAc-buffer, pH 4.0, was immobilized on a CM4 research grade chip purchased from Biacore by amino coupling using N-Hydroxysuccinimide (NHS), 1-Ethyl-3-(3-dimethylaminopropyl) carbodiimide hydrochloride (EDC) and 1 M Ethanolamine hydrochloride-NaOH pH 8.5 in a Biacore 2000 system. The mAb 11B6, its conjugate DTPA-11B6 and Herceptin as a nonspecific reference mAb, all in Biacore buffer was flown over two flow cells in five different concentrations (0.5 nM, 5 nm, 10 nM, 50 nM and 100 nM) to detect eventual binding. One of the two flow cells contained immobilized hK2 and the other was a blank reference. The chip was regenerated using 25 mM Glycin buffer, pH 2.7.

In Vitro Stability Studies

Stability of the labeled conjugates was tested in PBS and in an excess of EDTA, 500× more EDTA then DTPA conjugated on m11B6, incubated at 4° for 1 week and 2 weeks and were analyzed using ITLC strips, see above.

Animal Studies

All animal experiments were performed in accordance with national legislation on laboratory animals' protection. The animal study has been approved by the local Ethics Committee for Animal Research. Male immunodeficient nude mice, NMRI, (6-8 wk old) purchased from Taconic Europe (Bomholt, Denmark) were used for this study.

Xenografts of hK2-expressing LnCAP prostate carcinoma cells were subcutaneously implanted in the right flank and/or left flank at about $10*10^6$ cells per injection.

Animals that developed LNCaP tumors were divided into groups and injected with either the therapeutic agent 177Lu-DTP-11B6 or with a control, see Table 1 below:

TABLE 1

| Animals | Group nr | Treatment |
|---|---|---|
| 5 animals/group | 1 | NaCl (control) |
| 11 groups | 2 | Unspecific Ab labeled with 177Lu-low absorbed dose |
| Total = 55 animals | 3 | Unspecific ab labeled with 177Lu-high absorbed dose |
| | 4 | Only 177Lu-low absorbed dose |
| | 5 | Only 177Lu-high absorbed dose |
| | 6 | 177Lu-DTPA-m11B6: A/4 |
| | 7 | 177Lu-DTPA-m11B6: A/2 |
| | 8 | 177Lu-DTPA-m11B6: A |
| | 9 | 177Lu-DTPA-m11B6: 2*A |
| | 10 | 177Lu-DTPA-m11B6: 3*A |
| | 11 | Only m11B6 |
| | | A = 26.7 MBq |

All animals included were continuously measured and weighed within an interval of 3-4 days.

Initially some animals got a lower activity (8MBq) of $^{177}$Lu-DTPA-11B6 for investigation of the localization of the therapeutic agent using SPECT. One mouse from group 8 was also studied with SPECT. These animals had their organs removed and an automated NaI(TI) well-counter with a 3-inch NaI (TI) detector (1480 WIZARD, Wallac Oy, Turku, Finland) was used to quantify radioactivity in these tissue samples.

To study the effect on the bone marrow blood samples (10 µL) were taken regularly. Blood samples were collected twice a week for 8 weeks postinjection and WBC counts, RBC counts, and platelet counts were analyzed in a Medonic Cell Analyzer-Vet CA530 Vet (Boule Medical, Stockholm, Sweden). At the time of blood sampling, the weight and physical condition of the animals were monitored. Toxicity was evaluated by monitoring animals for loss of body weight, decline in general condition, and hematologic toxicity.

Tumor volume was measured with a caliper. The length l, with w and thickness t were measured and the volume was calculated.

Pharmacokinetics

For the biokinetic study of 111In-m11B6, mice were injected in a tail vein with radionuclide labeled to 25 µg m11B6 antibody. Animals were sacrificed at regular time intervals.

In brief, the mouse mAb 11B6 was conjugated with CHX-A"-DTPA and labeled with $^{111}$In forming $^{111}$In-CHX-A"-DTPA-11B6 ($^{111}$In-DTPA-11B6). Biodistribution studies were performed in an hK2- and AR-positive (LNCaP) PCa xenograft model. DU-145 xenografts (hK2 and AR negative) were used as a control. Animals, NMRI nude, were euthanized at designated time intervals, dissected and had organs removed for activity measurement. Micro-SPECT imaging was performed. Tumours were sectioned, stained and autoradiography was performed. Some animals were injected with cold mouse mAb 11B6 prior to injection of $^{111}$In-DTPA-11B6 to block the uptake of radiolabelled 11B6.

The biokinetics of 177Lu-m11B6 was obtained in the same way as for the 111In-m11B6 study.

Data Acquisition and Dosimetry

To determine the absorbed dose to the different target organs, the MIRD-scheme (1) was applied together with mouse-specific S-factors. The number of disintegrations (cumulated activity) was derived from the kinetic data with $^{111}$In-m11B6. Bi-exponential functions were fitted to the data points by a least-square algorithm, and the numbers of disintegrations were calculated as the integral of these expressions multiplied with the decay-factor. The cumulated activity for the bone marrow was based on the blood method (2), where the activity concentration in red marrow is supposed to be proportional to the activity concentration in blood. This red marrow to blood ratio (RMBLR) has been suggested to be 0.36 (2), which was also used in this study.

To determine the mouse-specific S-factors, a version of the MOBY (3) phantom was used in which the organ sizes could be specified. The average weight of the dissected organs from the kinetic-study was specified together with the average total weight. The rendering of the flexible NURBS surfaces then generates a strain-specific phantom. The phantom is voxelized in 160*160*400 voxels. A subcutaneous tumor were added on the left flank, by the representation of a sphere outside the normal skin-contour, but as an ellipsoid with a short axis half to the sphere radius perpendicular to the skin-contour, and the long axis being as the sphere radius. The salivary gland and the prostate gland were manually added to the phantom and represented as spheres with radius correlated to the average weights of the organs.

The phantom then acted as input for Monte Carlo simulations of S-factors for $^{177}$Lu and $^{111}$In with the MCNPX 2.6 code as described in earlier work (4).

Therapy Planning

Based on the relationship between absorbed dose and biological effect on the bone marrow in rats undergoing Radioimmunotherapy with 90Y and 177Lu (Larsson et al., 2012, *Med. Phys.* 39(7):4434-43) it could be estimated that the LD50 for bone marrow would be in the order of 12 Gy. In the literature LD50 for acute irradiation of rats and mice are the same, about 9 Gy (for example, see *Radiobiology for the radiologist*, Hall & Giacca (Eds), 2006, 6$^{th}$ edition).

The therapies were then designed from the assumption of a tolerable absorbed dose of 12 Gy to bone marrow. Then from the dosimetry calculations the activity corresponding to this absorbed dose was calculated. The therapy groups were then designed as giving them A/4, A/2, A, 2×A and 3×A. Corresponding activities were used for the controls.

Results

Radiolabelling of $^{177}$Lu-DTPA-m11B6

The labeling kinetics results in FIG. 16 show that the labeling efficiency is very high, reaching 90% after 2 hours incubation. This ensures a likelihood of excellent therapy efficacy with minor effects of unconjugated 177Lu.

The in vitro stability results in PBS and EDTA show good stability over time with almost no change with time within two weeks (see FIG. 17). Also, no difference can be seen between PBS and EDTA incubation, indicating a very good conjugation chemistry ensuring stability in vivo with long retention and circulation times.

Imaging

The SPECT images in FIG. 18 show the distribution of $^{177}$Lu-DTPA-m11B6 in xenografted nude mice, (8MBq injected).

The different images of FIG. 18 are as explained in Table 2.

TABLE 2

| Column 1 | Column 2 | Column 3 | Column 4 |
|---|---|---|---|
| S1: 48 h | | | |
| S1: 72 h | S2: 72 h | S3: 72 h | S11: 72 h DU 145 |
| S1: 168 h | S2: 168 h | S8: 168 h Blocked | S9: 168 h Blocked |

The first column for mouse S1 shows the excellent uptake in the tumor in mouse S1 with an increased uptake with time 48, 72 and 168 h pi. The second column shows mouse S2 at 72 and 168 h with same high tumor uptake. Column 3, row 2 shows mouse S3 at 72 h pi with similar high tumor uptake. Row 3, column 3 shows mouse S8 at 168 h pi with no tumor uptake after blocking with cold antibodies showing the specificity of m11B6 for tumor targeting. Similar results for mouse S9 in column 4, row 3. Finally mouse S11 in column 4, row 2 shows no uptake in tumor of cell line DU 145 not specific for the m11B6 antibody.

These results demonstrate the high specificity of m11B6 resulting in high tumor accumulation.

Biodistribution

The results of the biokinetic study of the 111In-m11B6 are discussed in Example 2 above. An accumulation is seen in the tumor tissue with a maximum of 16% IA/g at 48 hours; all other organs show a decline of activity except the salivary glands (see FIG. 8). Thus, a high tumor to normal organ ratio is obtained, which is a prerequisite for high therapy efficacy.

Biodistribution data for 177Lu-m11B6 (at 72 h and 168 h) is shown in FIG. 19. Here, a much higher accumulation of activity can be seen compared to $^{111}$In-m11B6, with almost 30% IA/g at 168 h. This further underlines the feasibility of high therapeutic efficacy with radiolabelled 11B6 antibody.

The detailed results at 72 h pi of blocking together with using tumor cell line DU-145 is shown in FIG. 20. Here, the distribution of the $^{177}$Lu-DTPA-m11B6 from the SPECT study shown above in mice with LnCaP or DU-145 and blocking the hK2 Ag with preinjection of non-conjugated 11B6 are given. As seen in detail the blocking and the tumor cell line DU-145 result in no uptake in the tumors showing the high specificity of m11B6.

Dosimetry

FIG. 21 shows the results of the biokinetic study of 111In-m11B6 used for the dosimetry calculations. In each graph within the composite figure, the upper dotted line represents the results of the kinetic study with one standard deviation, the solid curve is an adapted bi-exponential function and the lower dotted curve is when the decay of 111In is considered. The area under the lower dotted curve is the cumulated activity used in the dosimetry calculations.

Based on the biokinetics as shown in FIG. 21, the cumulated activities were calculated. Using the 111In S values, the absorbed dose per activity unit (Gy/MBq) were then calculated. In Table 3 below are given the results for 111In.

Based on the assumption that the same biokinetics can be used for 177Lu-m11B6, the corresponding cumulated activities were calculated with its physical half time. When using the S-values for 177Lu, the absorbed dose per activity unit was calculated. The assumption of similar biokinetics is justified by the results of the uptake of 177Lu-m11B6 showing similar uptake values as for 111In-m11B6 (see FIGS. 8 and 19).

TABLE 3

Absorbed dose (Gy/MBq) from therapy with $^{111}$In- and $^{177}$Lu-11B6

| | $^{111}$In | | $^{177}$Lu | |
|---|---|---|---|---|
| Organ | Self-dose | Total-dose | Self-dose | Total-dose |
| Remainder | 0.072 | 0.081 | 0.504 | 0.516 |
| Blood | 0.195 | 0.235 | 1.207 | 1.283 |
| Heart | 0.076 | 0.133 | 0.442 | 0.622 |
| Lung | 0.059 | 0.106 | 0.396 | 0.532 |
| Liver | 0.102 | 0.130 | 0.636 | 0.666 |
| Spleen | 0.082 | 0.115 | 0.670 | 0.716 |
| GI-tract | 0.041 | 0.073 | 0.246 | 0.298 |
| Kidney | 0.088 | 0.122 | 0.491 | 0.525 |
| Thyroid | 0.001 | 0.041 | 0.006 | 0.094 |
| Bone | 0.020 | 0.086 | 0.131 | 0.267 |
| Brain | 0.003 | 0.025 | 0.017 | 0.039 |
| Prostate | 0.036 | 0.075 | 0.236 | 0.295 |
| Testes | 0.031 | 0.061 | 0.246 | 0.294 |
| Salivary glands | 0.223 | 0.249 | 1.885 | 1.926 |
| Tumor | 0.294 | 0.312 | 2.236 | 2.252 |
| Bone Marrow | 0.063 | 0.092 | 0.386 | 0.452 |

Based on an LD50 value of 12 Gy of bone marrow, a dose of 26.7 MBq can be injected. This means an absorbed dose for the tumor of 60 Gy.

Recalculating the tumor absorbed dose (assuming that the 111-In-m11B6 kinetics is the same as for 177Lu-m11B6) and changing uptake values at 72 h pi (16% IA/g till 20% IA/g) and at 168 h pi (15% IA/g to 28% IA/g) results in the absorbed doses as given in Table 4 below. It can then be seen that the absorbed dose to tumor will increase from 60 Gy to 120 Gy

TABLE 4

| Organ | Self-dose | Total absorbed dose |
|---|---|---|
| Remainder | 0.494456 | 0.507415 |
| Blood | 1.20655 | 1.28288 |
| Heart | 0.441901 | 0.621222 |
| Lung | 0.396110 | 0.530831 |
| Liver | 0.636344 | 0.665149 |
| Spleen | 0.669825 | 0.715375 |
| GI-tract | 0.245824 | 0.297540 |
| Kidney | 0.490722 | 0.524355 |
| Thyroid | 0.00649596 | 0.0923319 |
| Bone | 0.131186 | 0.266107 |
| Brain | 0.0170275 | 0.0386855 |
| Prostate | 0.236380 | 0.293902 |
| Testes | 0.246161 | 0.293579 |
| Saliva | 1.88491 | 1.92563 |
| Tumor | 4.48777 | 4.50278 |
| Bone marrow | 0.386496 | 0.451228 |

The above dosimetry calculations are based on a proper dosimetry model; the biokinetics reveal that a therapeutic absorbed dose can be delivered to the tumors within safe limits for bone marrow toxicity.

Animal Tumor Shrinkage

FIG. 22 shows how the tumor in one of the mice (visible on the animal's flank, under the skin) decreases in volume following treatment.

Radioimmunotherapy Results

FIG. 23 shows the results for the study groups with administered activities (a) D, (b) 2×D and (c) a control group (where D=26.7 MBq).

There is a clear trend of decrease of tumor volume in both treatment groups. The onset of tumor shrinkage is seen already a few days after injection of 177Lu-m11B6. In the control group there is an increase of tumor volume after the injection of NaI solution.

FIG. 24 (*a*) shows the results for one of the mice in the group injected with activity A. Here, the tumor grows steadily from day one until day six when activity A of 177Lu-m11B6 is administered. Following treatment, a rapid drop in tumor volume is observed.

In the SPECT study (8 d pi) the tumor volume is shown with still activity present; see FIG. 24(*b*).

CONCLUSION

The present study with exemplary antibody 177Lu-m11B6 clearly demonstrates a therapeutic efficacy against prostate cancer tumours in vivo.

Both theoretical calculations based on the special dosimetry model and the in vivo measured biokinetics show favorable dosimetry giving a high therapeutic ratio. This is then verified in the animal study with good therapy results showing rapid tumor volume shrinkage.

REFERENCES

1. Bolch W E, Eckerman K F, Sgouros G, Thomas S R. MIRD pamphlet No. 21: a generalized schema for radiopharmaceutical dosimetry—standardization of nomenclature. J Nucl Med. 2009; 50:477-484.
2. Sgouros G. Bone marrow dosimetry for radioimmunotherapy: theoretical considerations. J Nucl Med. 1993; 34:689-694.
3. Segars W P, Tsui B M, Frey E C, Johnson G A, Berr S S. Development of a 4-D digital mouse phantom for molecular imaging research. Mol Imaging Biol. 2004; 6:149-159.
4. Larsson E, Strand S E, Ljungberg M, Jonsson B A. Mouse S-factors based on Monte Carlo simulations in the anatomical realistic Moby phantom for internal dosimetry. Cancer Biother Radiopharm. 2007; 22:438-442.
5. Erik Larsson, Michael Ljungberg, Linda Martensson, Rune Nilsson, and Jan Tennvall, Sven-Erik Strand and Bo-Anders Jonsson Use of Monte Carlo simulations with a realistic rat phantom for examining the correlation between hematopoietic system response and red marrow absorbed dose in Brown Norway rats undergoing radionuclide therapy with 177Lu- and 90Y-BR96 mAbs Medical
6. Linda Martensson, Zhongmin Wang, Rune Nilsson, Tomas Ohlsson, Peter Senter, Hans-Olov Sjögren, Sven-Erik Strand, Jan Tennvall, Determining Maximal Tolerable Dose of the Monoclonal Antibody BR96 Labeled with 90Y or 177Lu in Rats: Establishment of a Syngeneic Tumor Model to Evaluate Means to Improve Radio immunotherapy *Clin Cancer Res* 2005; 11:7104s-7108s. 2005.

The invention claimed is:

1. A method for the treatment of castration-resistant prostate cancer (CRPC) in a patient, the method comprising administering a therapeutically effective amount of an agent comprising
   (a) an antibody or antigen-binding fragment thereof with specificity for human glandular kallikrein (hK2) and
   (b) a cytotoxic moiety comprising $^{225}$Ac,
   wherein the antibody or antigen-binding fragment thereof with specificity for hK2 comprises the six complementarity determining regions (CDRs) of antibody 11B6, wherein the heavy chain of the 11B6 antibody comprises SEQ ID NO: 4 and the light chain of the 11B6 antibody comprises SEQ ID NO: 5.

2. The method of claim 1, wherein the antibody or antigen-binding fragment thereof with specificity for hK2 is selected from the group consisting of 11B6 and antigen-binding fragments thereof, wherein the heavy chain of the 11B6 antibody comprises SEQ ID NO: 4 and the light chain of the 11B6 antibody comprises SEQ ID NO: 5.

3. The method of claim 1, wherein the antibody or the antigen-binding fragment thereof comprises human framework residues.

4. The method of claim 1, wherein the antibody or antigen-binding fragment thereof with specificity for hK2 comprises at least a portion of an antibody constant region derived from a human antibody.

5. The method of claim 1, wherein the antibody or antigen-binding fragment thereof with specificity for hK2 is linked indirectly to the cytotoxic moiety.

6. The method of claim 1, wherein the antibody or antigen-binding fragment thereof with specificity for hK2 is linked directly to the cytotoxic moiety.

7. The method of claim 1, wherein the agent displays tumor uptake characteristics substantially equivalent to the tumor uptake characteristics of the antibody or antigen-binding fragment thereof with specificity for hK2 alone.

8. The method of claim 1, wherein the prostate cancer is metastatic CRPC.

9. The method of claim 1, wherein the patient has prostate cancer and is less than 70 years old at the time of diagnosis of prostate cancer and/or at the time of treatment.

10. The method of claim 1, wherein the patient is characterized in that a family member has been previously diagnosed with prostate cancer.

11. The method of claim 1, wherein the patient has previously been treated with one or more prostate cancer therapies.

12. The method of claim 1, wherein the cytotoxic moiety is linked to the antibody or antigen-binding fragment thereof via a non-phenolic linker.

13. The method of claim 1, wherein the cytotoxic moiety is linked to the antibody or antigen-binding fragment thereof via a chelating moiety.

14. The method of claim 13, wherein the chelating moiety comprises a derivatives of 1,4,7,10-tetraazacyclododecane-1,4,7,10, tetraacetic acid (DOTA), a derivative of diethylenetriaminepentaacetic acid (DTPA), a derivative of S-2-(4-isothiocyanatobenzyl)-1,4,7-triazacyclononane-1,4,7-triacetic acid (NOTA), or a derivatives of 1,4,8,11-tetraazacyclodocedan-1,4,8,11-tetraacetic acid (TETA).

15. The method of claim 13, wherein the chelating moiety comprises 1,4,7,10-tetraazacyclododecane-1,4,7,10, tetraacetic acid (DOTA).

16. The method of claim 1, wherein the method reduces the rate of growth of prostatic cancer cells in the patient by at least 10% compared to the observed rate of growth of prostatic cancer cells in the patient prior to the treatment.

17. The method of claim 1, wherein the method reduces the rate growth of prostatic cancer cells in the patient by at least 20%, 30%, 40%, 50%, 60%, 70%, 80% or 90% compared to the observed rate of growth of prostatic cancer cells in the patient prior to the treatment.

18. The method of claim 1, wherein the agent is administered at a dose of about 1 mg/kg.

* * * * *